United States Patent
Zhang et al.

(10) Patent No.: US 6,747,048 B2
(45) Date of Patent: Jun. 8, 2004

(54) PYRIDINE-BASED THYROID RECEPTOR LIGANDS

(75) Inventors: Minsheng Zhang, Warren, NJ (US); Jon Hangeland, Morrisville, PA (US); Yolanda Caringal, Lawrenceville, NJ (US); Todd Friends, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/431,269

(22) Filed: May 7, 2003

(65) Prior Publication Data

US 2004/0039028 A1 Feb. 26, 2004

Related U.S. Application Data

(60) Provisional application No. 60/378,497, filed on May 8, 2002.

(51) Int. Cl.⁷ ................. C07D 213/02; A61K 31/44
(52) U.S. Cl. ................. 514/349; 514/345; 514/348; 514/352; 546/296; 546/297; 546/307; 546/312; 546/339; 546/343; 546/344
(58) Field of Search ................. 546/296, 297, 546/307, 312, 339, 343, 344; 514/345, 348, 349, 352

(56) References Cited

U.S. PATENT DOCUMENTS

| | | |
|---|---|---|
| 3,239,345 A | 3/1966 | Hodge et al. |
| 3,983,140 A | 9/1976 | Endo et al. |
| 4,027,009 A | 5/1977 | Grier et al. |
| 4,036,979 A | 7/1977 | Asato |
| 4,231,938 A | 11/1980 | Monaghan et al. |
| 4,346,227 A | 8/1982 | Terahara et al. |
| 4,411,890 A | 10/1983 | Momany |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,177,080 A | 1/1993 | Angerbauer et al. |
| 5,273,995 A | 12/1993 | Roth |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,541,204 A | 7/1996 | Sher et al. |
| 5,595,872 A | 1/1997 | Wetterau, II et al. |
| 5,686,104 A | 11/1997 | Mills et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,184,231 B1 | 2/2001 | Hewawasam et al. |

FOREIGN PATENT DOCUMENTS

| | | |
|---|---|---|
| EP | 0142146 | 5/1985 |
| EP | 0221025 | 5/1987 |
| FR | 2596393 | 10/1987 |
| WO | WO 86/03488 | 6/1986 |
| WO | WO 86/07054 | 12/1986 |
| WO | WO 89/07110 | 8/1989 |
| WO | WO 89/07111 | 8/1989 |
| WO | WO 93/04081 | 3/1993 |
| WO | WO 97/21993 | 6/1997 |
| WO | WO 99/00353 | 1/1999 |

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869–1871 (1988).

Biller, S.A. et al., "Squalene Synthase Inhibitors", Current Pharmaceutical Design, vol. 2, pp. 1–40 (1996).

Bundagaard, H., Design of Prodrugs, Elsevier Science Publishers B.V. (1985) (table of contents).

Bundgaard, H., "Design and Application of Prodrugs", A Textbook of Drug Design and Development, Harwood Academic Publishers, Krogsgaard–Larsen, P. and Bundgaard, T., eds., pp. 113–191 (1991).

(List continued on next page.)

Primary Examiner—Zinna Northington Davis
(74) Attorney, Agent, or Firm—Maureen P. O'Brien

(57) ABSTRACT

Novel pyridine-based thyroid receptor ligands are provided which have the general formula I

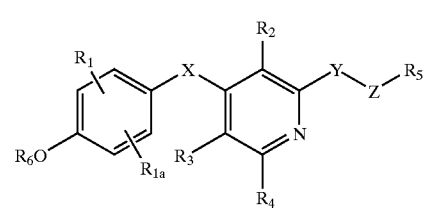

wherein:
X is oxygen (—O—), sulfur (—S—), sulfoxide (—S(O)—), sulfonyl (—SO$_2$—), CR$_8$R$_8$ or NR$_8$;
Y is —NR$_8$, oxygen (—O—), —CH$_2$— or sulfur (—S—);
Z is a bond or substituted or unsubstituted C$_{1-4}$ alkyl; and wherein the substituents are as described herein.

In addition, a method is provided for preventing, inhibiting or treating diseases or disorders associated with metabolism dysfunction or which are dependent upon the expression of a T$_3$ regulated gene, wherein a compound as described above is administered in a therapeutically effective amount.

25 Claims, No Drawings

OTHER PUBLICATIONS

Capson, T.L., "Synthesis and Evaluation of Ammonium Analogs of Carbocationic Intermediates in Squalene Biosynthesis", dissertation, Department of Medicinal Chemistry, University of Utah, pp. iv–v, table of contents, 16–17, 40–43, 48–51 (Jun. 1987).

Corey, E.J. et al., "Application of Unreactive Analogs of Terpenoid Pyrophosphates to Studies of Multistep Biosynthesis. Demonstration That 'Presqualene Pyrophosphate' is an Essential Intermediate on the Path to Squalene", J. Am. Chem. Soc. vol. 98, No. 5, pp. 1291–1293 (1976).

Edwards, J.P. et al., "Nonsteroidal Androgen Receptor Agonists Based on 4–(trifluoromethyl)–2H–pyrano[3,2–g] quinolin–2–one", Bioorganic & Medicinal Chemistry Letters, vol. 9, pp. 1003–1008 (1999).

Evans, D.A. et al., "Synthesis of Diaryl Ethers through the Copper–Promoted Arylation of Phenols with Arylboronic Acids. An Expedient Synthesis of Thyroxine". Tetrahedron Letters, vol. 39, pp. 2937–2940 (1998).

Ghiselli, G., "The Pharmacological Profile of FCE 27677; A Novel ACAT Inhibitor with Potent Hypollipidemic Activity Mediated by Selective Suppression of the Hepatic Secretion of ApoB–100–Containing Lipoprotein", Cardiovascular Drug Reviews, vol. 16, No. 1, pp. 16–30 (1998).

Greene, T.W. et al., Protective Groups in Organic Synthesis, Third Edition, John Wiley & Sons, Inc. (1999) (table of contents).

Hara, S., "Ileal Naibile acid cotransporter inhibitors", Drugs of the Future, vol. 24, No. 4, pp. 425–430 (1999).

Hamann, L.G. et al., "Discovery of a Potent, Orally Active, Nonsteroidal Androgen Receptor Agonist: 4–Ethyl–1,2,3, 4–tetrahydro–6–(trifluoromethyl)–6–pyridono[5,6–g]– quinoline (LG121071)", J. Med. Chem., vol. 42, pp. 210–212 (1999).

Johannson, G. et al., "Growth Hormone Treatment of Abdominally Obese Men Reduces Abdominal Fat Mass, Improves Glucose and Lipoprotein Metabolism, and Reduces Diastolic Blood Pressure", J. Clin. Endocrinol. Metab., vol. 82, No. 3, pp. 727–734 (1997).

Krause, B.R. et al., "ACAT Inhibitors: Physiologic Mechanisms for Hypolipidermic and Anti–Atherosclerotic Activities in Experimental Animals", Inflammation: Mediators Pathways, CRC Press, Inc., Ruffolo, Jr., R.R. and Hollinger, M.A., eds., pp. 173–198 (1995).

McClard, R.W. et al., "Novel Phosphonylphosphinyl (P–C–P–C–) Analogues of Biochemically Interesting Diphosphates, Syntheses and Properties of P–C–P–C– Analogues of Isopentenyl Diphosphate and Dimethylallyl Diphosphate", J. Am. Chem. Soc., vol. 109, pp. 5544–5545 (1987).

Nicolosi, R.J. et al., "The ACAT Inhibitor, Cl–1011 is effective in the prevention and regression of aortic fatty streak area in hamsters", Atherosclerosis, vol. 137, pp. 77–85 (1998).

Ortiz de Montellano, P.R. et al., "Inhibition of Squalene Synthetase by Famesyl Pyrophosphate Analogues", Journal of Medicinal Chemistry, vol. 20, No. 2, pp. 243–249 (1977).

Salisbury, B.G. et al., "Hypocholesterolemic activity of a novel inhibitor of cholesterol absorption, SCH 48461", Atherosclerosis, vol. 115, pp. 45–63 (1995).

Shieh, W.–C. et al., "A Simple Asymmetric Synthesis of 4–Arylphenylalanines via Palladium–Catalyzed Cross–Coupling Reaction of Arylboronic Acids with Tyrosine Triflate", J. Org. Chem., vol. 57, pp. 379–381 (1992).

Sliskovic, D.R. et al., "ACAT Inhibitors: Potential Anti–atherosclerotic Agents", Current Medicinal Chemistry, vol. 1, pp. 204–225 (1994).

Smith, C. et al., "RP 73163: A Bioavailable Alkylsulphinyl–Diphenylimidazole ACAT Inhibitor", Bioorganic & Medicinal Chemistry Letters, vol. 6, No. 1, pp. 47–50 (1996).

Sobera, L.A. et al., "Avasimlbe: Treatment of Lipoprotein Disorders, ACAT Inhibitor", Drugs of Future, vol. 24, No. 1, pp. 9–15 (1999).

Stout, D.M., "Inhibitors of Acyl–CoA:Cholesterol O–Acyl Transferase (ACAT) as Hypocholesterolemic Agents. 6. The First Water–Soluble ACAT Inhibitor with Lipid–Regulating Activity, etc.", Chemtracts–Organic Chemistry, vol. 6, pp. 359–362 (1995).

Takeda, K, et al., "Recessive Inheritance of Thyroid Hormone Resistance Caused by Complete Deletion of the Protein–Coding Region of the Thyroid Hormone Receptor–$\beta$ Gene", Journal of Clinical Endocrinology and Metabolism, vol. 74, No. 1, pp. 49–55 (1992).

Wermuth, C.G. et al., "Designing Prodrugs and Bioprecursors I: Carrier Prodrugs", The Practice of Medicinal Chemistry, Academic Press, Wermuth, C.G., ed., pp. 671–696 (1996).

PYRIDINE-BASED THYROID RECEPTOR LIGANDS

CROSS-REFERENCE TO RELATED APPLICATION

This application claims the benefit of U.S. Provisional Application No. 60/378,497, filed May 8, 2002, which is incorporated herein by reference in its entirety.

FIELD OF THE INVENTION

This invention relates to novel pyridine-based compounds which are thyroid receptor ligands and are preferably selective for the thyroid hormone receptor β. Further, the present invention relates to methods for using such compounds and to pharmaceutical compositions containing such compounds.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, metabolic rate, body temperature and mood, and influence blood levels of serum low density lipoprotein (LDL). Thus, in hypothyroidism there is weight gain, high levels of LDL cholesterol, and depression. In hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, may be restricted by certain detrimental effects from thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor ligands, particularly agonists of the thyroid hormone receptor could lead to specific therapies for these common disorders, while avoiding the cardiovascular and other toxicity of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. Whereas many mutations in the TRβ gene have been found and lead to the syndrome of generalized resistance to thyroid hormone, mutations leading to impaired TRα function have not been found.

A growing body of data suggests that many or most effects of thyroid hormones on the heart, and in particular, on the heart rate and rhythm, are mediated through the α-form of the $TR\alpha_1$ isoform, whereas most actions of the hormone such as on the liver, muscle and other tissues, are mediated more through the β-forms of the receptor. Thus, a TRβ-selective agonist might not elicit the cardiac rhythm and rate influences of the hormones, but would elicit many other actions of the hormones. Applicants believe that the α-form of the receptor is primarily associated with heart rate function for the following reasons:

1) tachycardia is very common in the syndrome of generalized resistance to thyroid hormone in which there are defective TRβ-forms, and high circulating levels of $T_4$ and $T_3$;
2) there was a tachycardia in the only described patient with a double deletion of the TRβ gene (Takeda et al, J. Clin. Endrocrinol. & Metab. 1992, Vol. 74, p. 49);
3) a double knockout TRα gene (but not β-gene) in mice resulted in a slower mouse heart rate, as compared to control mice; and
4) western blot analysis of human myocardial TRs show presence of the $TR\alpha_1$, $TR\alpha_2$ and $TR\beta_2$ proteins, but not $TR\beta_1$.

If these indications are correct, then it may be possible that a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and (6) osteoporosis in combination with a bone resorption inhibitor.

SUMMARY OF THE INVENTION

In accordance with the illustrative embodiments and demonstrating features of the present invention, compounds are provided which are thyroid receptor ligands, and have the general formula I

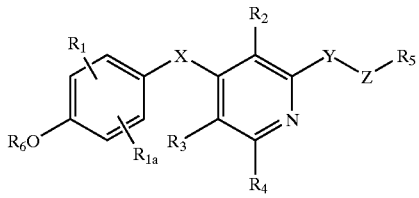

wherein
X is oxygen (—O—), sulfur (—S—), sulfoxide (—S(O)—), sulfonyl (—SO$_2$—), CR$_8$R$_8$' or NR$_8$;

Y is oxygen (—O—), —NR$_8$, —CH$_2$— or sulfur (—S—);

Z is a bond or substituted or unsubstituted C$_{1-4}$ alkyl;

R$_1$ is halogen, trifluoromethyl, substituted or unsubstituted C$_{1-6}$ alkyl, substituted or unsubstituted aryl, substituted or unsubstituted heteroaryl, substituted amide, sulfone, sulfonamide, aryloxy or C$_{3-7}$ cycloalkyl, wherein said aryl, heteroaryl or cycloalkyl ring(s) are attached or fused to the aromatic ring;

R$_{1a}$ is hydrogen, halogen, substituted or unsubstituted C$_{1-6}$ alkyl, substituted or unsubstituted aryl, or substituted or unsubstituted heteroaryl;

R$_2$ and R$_3$ are each independently hydrogen, halogen, substituted or unsubstituted C$_{1-4}$ alkyl or substituted or unsubstituted C$_{3-5}$ cycloalkyl, wherein at least one of R$_2$ and R$_3$ being other than hydrogen;

R$_4$ is hydrogen, halogen, amino, O—R$_7$, S—R$_7$ or C$_{1-4}$ alkyl;

R$_5$ is hydroxyl (—OH), carboxylic acid (—COOH), sulfonic acid (—SO$_2$OH) or phosphonic acid (—PO$_3$H$_2$);

R$_6$ is hydrogen, alkyl, alkanoyl or aroyl (such as acetyl or benzoyl);

R$_7$ is hydrogen or C$_{1-4}$ alkyl;

R$_8$ for each occurrence is independently hydrogen, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy or hydroxyl; and R$_8$' is hydrogen, a bond, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy or hydroxyl, or R$_8$ and R$_8$' together form a carbonyl (—CO—).

The definition of formula I above includes all prodrug-esters, stereoisomers and pharmaceutically acceptable salts of formula I.

The compounds of formula I are thyroid hormone receptor ligands and include compounds which are, for example, selective agonists, partial agonists, antagonists or partial antagonists of the thyroid receptor. Preferably, the compounds of formula I possess activity as agonists of the thyroid receptor, preferably selective agonists of the thyroid receptor-beta, and may be used in the treatment of diseases or disorders associated with thyroid receptor activity. In particular, the compounds of formula I may be used in the treatment of diseases or disorders associated with metabolism dysfunction or which are dependent upon the expression of a T$_3$ regulated gene, such as obesity, hypercholesterolemia, atherosclerosis, cardiac arrhythmias, depression, osteoporosis, hypothyroidism, goiter, thyroid cancer, glaucoma, skin disorders or diseases and congestive heart failure.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the thyroid receptor, particularly, the thyroid receptor-beta, such as the diseases or disorders defined above and hereinafter, wherein a therapeutically effective amount of a compound of formula I is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

Preferably, compounds of this invention include embodiments of formula I wherein X is oxygen, sulfur, sulfoxide, sulfonyl, —CH$_2$— or —NH—;

Y is oxygen or —NH—;

R$_1$ is halogen, substituted or unsubstituted C$_{1-6}$ alkyl, C$_{3-7}$ cycloalkyl, substituted aryl, aryloxy, substituted amide, sulfone or sulfonamide, wherein R$_1$ is attached ortho to the R$_6$O— group;

R$_2$ and R$_3$ are each independently iodo, bromo, chloro or fluoro;

R$_4$ is hydrogen, fluoro, chloro, amino, —OCH$_3$, hydroxyl (—OH) or methyl;

R$_5$ is carboxylic acid; and

R$_6$ is hydrogen.

Other preferred embodiments of the invention include compounds of formula I wherein X is carbonyl, CHR$_8$ or NR$_8$;

Y is oxygen or —NH—;

R$_1$ is halogen, substituted or unsubstituted C$_{1-6}$ alkyl, substituted aryl, substituted amide, sulfone, sulfonamide or C$_{3-7}$ cycloalkyl;

R$_2$ and R$_3$ are independently bromo, chloro or methyl;

R$_4$ is hydrogen, fluoro, chloro, hydroxyl, amino, methoxy or methyl;

R$_5$ is a carboxylic acid; and

R$_6$ is hydrogen.

Further preferred embodiments of the invention include compounds of formula I having the structure:

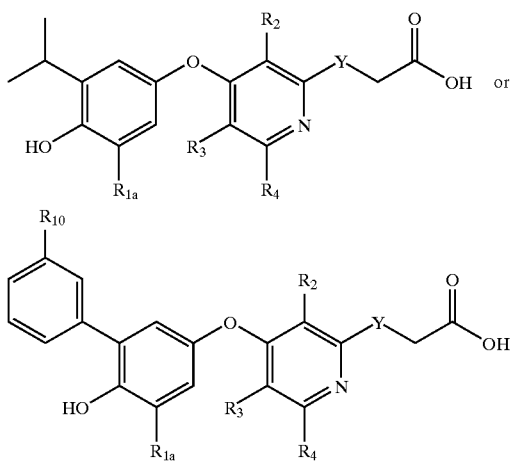

wherein

Y is oxygen or —NH—.

$R_{1a}$ is hydrogen, methyl or ethyl;

$R_2$ and $R_3$ are halogen;

$R_4$ is hydrogen, halogen, amino, —OCH$_3$ or hydroxyl; and $R_{10}$ is hydrogen, halogen or substituted or unsubstituted $C_{1-4}$ alkyl.

DETAILED DESCRIPTION OF THE INVENTION

The following abbreviations have the indicated meanings:
Ar=aryl
Bn=benzyl
DMF=N,N-dimethylformamide
DMSO=dimethyl sulfoxide
Et=ethyl
EtOAc=ethyl acetate
g=gram(s)
h or hr=hour(s)
Me=methyl
M+H=parent plus a proton
min=minute(s)
mL=milliliter
mg=milligram(s)
mol=moles
mmol=millimole(s)
M=molar
Ph=phenyl
RT=room temperature
HPLC=high performance liquid chromatography
NMR=nuclear magnetic resonance
THF=tetrahydrofuran
TFA=trifluoroacetic acid
μL=microliter The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "alkyld" as employed herein alone or as part of another group includes both straight and branched chain hydrocarbons, containing 1 to 12 carbons in the normal chain, preferably 1 to 4 carbons, such as methyl, ethyl, propyl, isopropyl, butyl, t-butyl, or isobutyl, pentyl, hexyl, isohexyl, heptyl; 4,4-dimethylpentyl, octyl, 2,2,4-trimethylpentyl, nonyl, decyl, undecyl, dodecyl. "Substituted alkyl" includes an alkyl group optionally substituted with one or more functional groups which are commonly attached to such chains, such as, alkyl, alkenyl, alkynyl, aryl, cycloalkyl, heteroaryl, hydroxy, cyano, nitro, amino, halo, carboxyl or alkyl ester thereof and/or carboxamide, substituted or unsubstituted.

Unless otherwise indicated, the term "alkoxy" refers to alkyl-O—. Examples of alkoxy groups include methoxy, ethoxy, propoxy, isopropoxy, cyclopropyloxy, cyclohexyloxy and the like.

The term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl). "Substituted aryl" includes an aryl group optionally substituted through available carbon atoms with one or more groups selected from hydrogen, halo, substituted or unsubstituted alkyl, haloalkyl, alkoxy, haloalkoxy, alkenyl, trifluoromethyl, trifluoromethoxy, alkynyl, hydroxy, amino, nitro, cyano and/or any of the alkyl substituents set out herein.

The term "alkanoyl" refers to alkyl-C(O)—.

The term "aroyl" refers to aryl-C(O)—.

Unless otherwise indicated, the term "aryloxy" as employed herein, alone or as part of another group, denotes —OR— wherein R is aryl as defined herein.

The term "heteroaryl" means a 5- or 6-membered aromatic heterocyclic ring which contains one or more heteroatoms selected from nitrogen, sulfur, oxygen and/or a SO or SO$_2$ group. Such rings may be fused to another aryl or heteroaryl ring and include possible N-oxides. "Substituted heteroaryl" includes a heteroaryl group optionally substituted with one or more substituents, such as those described for substituted alkyl and/or substituted aryl.

The term "amino" as used herein refers to —NR$_A$R$_B$ where R$_A$ and R$_B$ are independently hydrogen, or R$_A$ and/or R$_B$ may optionally be a substituent, such as aryl, alkyl, alkenyl, alkynyl, cycloalkyl, hydroxyl, cyano, nitro, carboxyl, halo, alkylthio, heteroaryl, heterocycle, heterocycle(aryl) carboalkyl and the like.

The term "substituted amide" as used herein refers to an amide linkage: —C(O)NR where R is hydrogen or may optionally be a substituent, such as aryl, alkyl, alkenyl, alkynyl, cycloalkyl, hydroxyl, cyano, nitro, amino, carboxyl, halo, alkylthio, heteroaryl, heterocycle carboalkyl and the like.

The term "sulfonamide" as used herein refers to a sulfonamide linkage: —SO$_2$NRR' where R and R' are independently hydrogen, or one or both of R and R' may optionally be substituents, such as any of the substituents described in the definition of substituted alkyl or substituted amino.

The term "sulfone" as used herein refers to a sulfone linkage: —SO$_2$R where R is hydrogen or may optionally be a substituent, such as aryl, alkyl, alkenyl, alkynyl, cycloalkyl, hydroxyl, cyano, nitro, amino, carboxyl, halo, alkylthio, heteroaryl, heterocycle carboalkyl and the like.

The term "heterocycle" or "heterocyclo" as used herein, represents a 5- to 7-membered monocyclic ring system which may be saturated or unsaturated, and which consists of carbon atoms and from one to four heteroatoms selected from N, O or S. Exemplary monocyclic heterocyclo groups include 2- and 3-thienyl, 2- and 3-furyl, 2-, 3-, and 4-pyridyl and imidazolyl. The term heterocycle or heterocyclic ring also includes bicyclic rings wherein the five- or six-membered ring containing oxygen and/or sulfur and/or nitrogen atoms as defined above is fused to a benzene ring and the bicyclic ring is attached by way of an available atom. Exemplary bicyclic heterocycle groups include 4-, 5-, 6- or 7-indolyl, 4-, 5-, 6-, or 7-isoindolyl, 5-, 6-, 7- or 8-quinolinyl, 5-, 6-, 7- or 8-isoquinolinyl and 4-, 5-, 6- or 7-benzothiazoyl. "Substituted heterocyclo" includes a heterocyclo group optionally substituted with one or more substituents, such as those described for substituted alkyl and/or substituted aryl.

Unless otherwise indicated, the term "alkenyl" as used herein refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as those described for substituted alkyl and/or substituted aryl.

The term "arylalkyl" refers to alkyl groups as described above having an aryl substituent. Representative examples of arylalkyl include, but are not limited to, benzyl, 2-phenylethyl, 3-phenylpropyl and the like. "Substituted arylalkyl" includes an arylalkyl group optionally substituted with one or more substituents, such as those described for substituted alkyl and/or substituted aryl.

The term "cycloalkyl" or "cycloalkenyl" as used herein includes saturated or partially saturated (containing one or more double bonds) cyclic hydrocarbon groups containing 3 to 7 carbon atoms, such as cyclopropyl, cyclobutyl, cyclopentyl, cyclohexyl. "Substituted cycloalkyl" or "substituted cycloalkenyl" include a cycloalkyl or cycloalkenyl group optionally substituted with one or more substituents, such as those described for substituted alkyl and/or substituted aryl.

The term "halogen" or "halo" as used herein alone or as part of another group-refers to chlorine, bromine, fluorine and iodine, with chlorine or bromine being preferred.

The $(CH_2)_n$ group is an alkyl group that includes 0 to 4 carbons in the normal chain which may include 1, 2, or 3 alkyl substituents.

The term "carbonyl", as used herein, refers to a —C(O)— group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolainine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The compounds of formula I may also have prodrug forms. Any compound that will be converted in vivo to provide the bioactive agent (i.e., the compound of formula I) is a prodrug within the scope and spirit of the invention.

Various forms of prodrugs are well known in the art. A comprehensive description of prodrugs and prodrug derivatives may be found in:
a.) *The Practice of Medicinal Chemistry*, Camille G. Wermuth et al., Ch 31, (Academic Press, 1996);
b.) *Design of Prodrugs*, edited by H. Bundgaard, (Elsevier, 1985); and
c.) *A Textbook of Drug Design and Development*, P. Krogsgaard-Larson and H. Bundgaard, eds. Ch 5, pgs 113–191 (Harwood Academic Publishers, 1991).
Said references are incorporated herein by reference.

Embodiments of prodrugs suitable for use in the present invention include lower alkyl esters, such as ethyl ester, or acyloxyalkyl esters such as pivaloyloxymethyl (POM).

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I of the invention can be prepared as shown in the following reaction schemes and description thereof, as well as by relevant published literature procedures that may be used by one skilled in the art. Exemplary reagents and procedures for these reactions appear hereinafter and in the working Examples. Protection and deprotection in the Schemes below may be carried out by procedures generally known in the art. For example, see T. W. Greene & P. G. M. Wuts, "Protecting Groups in Organic Synthesis", 3rd Edition, (Wiley, 1999), incorporated herein by reference.

tion of 5 and/or 6 would provide the desired compounds of formula I wherein $R_4$=F or H.

Poly-substituted prime rings may be prepared by using commerically available polysubstituted phenols as illustrated below in Scheme 1 b where X represents a halogen.

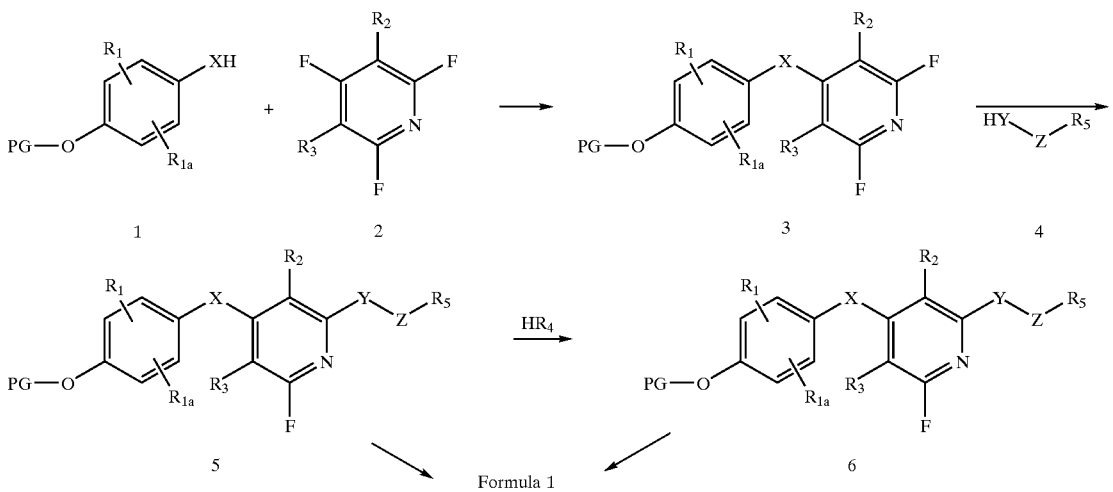

Scheme 1 depicts a general synthetic approach to compounds of formula I wherein X=O, S or $NR_8$, which utilizes the displacement reaction of an appropriately substituted phenol, thiophenol or aniline 1 such as 3-isopropyl-4-methoxyphenol or 4-methoxynaphthol with a pentasubstituted pyridine 2 such as 3,5-dichloro-2,4,6-trifluoropyridine or pentafluoro pyridine to provide intermediate 3. In structure 1 and all other applicable structures contained in further schemes described below, the term "PG" refers to a protecting group appropriate for the functional group indicated (in this instance, for a phenolic oxygen). Subsequent displacement of the 2-fluoro and 6-fluoro substituents on the pyridine 3 with nucleophiles 4 and reactant $HR_4$ sequentially provide intermediates 5 and 6 respectively. Examples of suitable nucleophiles 4 include, but are not limited to, glycine methyl ester and methyl glycolate. Examples of reactant $HR_4$ include, but are not limited to, alkylthiol, sodium alkoxide, alkylamine, or benzylamine. Compounds of formula I wherein X is sulfoxide or sulfonyl can be derived from intermediates 5 or 6 when X is S, via oxidation with an oxidating agent, for example mCPBA. Further protecting group and functional group manipulation of intermediates 5 or 6 will provide the compounds of formula I where X is O, S, $NR_8$, sulfoxide and sulfonyl.

For example, where intermediate 1 is 3-isopropyl-4-methoxy phenol (X is oxygen) and intermediate 2 is 3,5-dichloro-2,4,6-trifluoro pyridine ($R_2$ and $R_3$ are chlorine), the resulting intermediate 3 would be the corresponding diaryl ether where X=O and $R_2$=$R_3$=Cl. The 2-fluoro substituent of this intermediate can be readily displaced with nucleophile 4 where Y is O, $NR_8$, CH2 or sulfur, such as an amine or alkoxide, to form intermediate 5. The 6-fluoro substituent of the resulting amino or alkoxypyridine 5 can then be further displaced with a third nucleophile, such as ethylthiol in presence of potassium carbonate to provide the intermediate 6. Deprotection or Raney-Nickel desulfurization

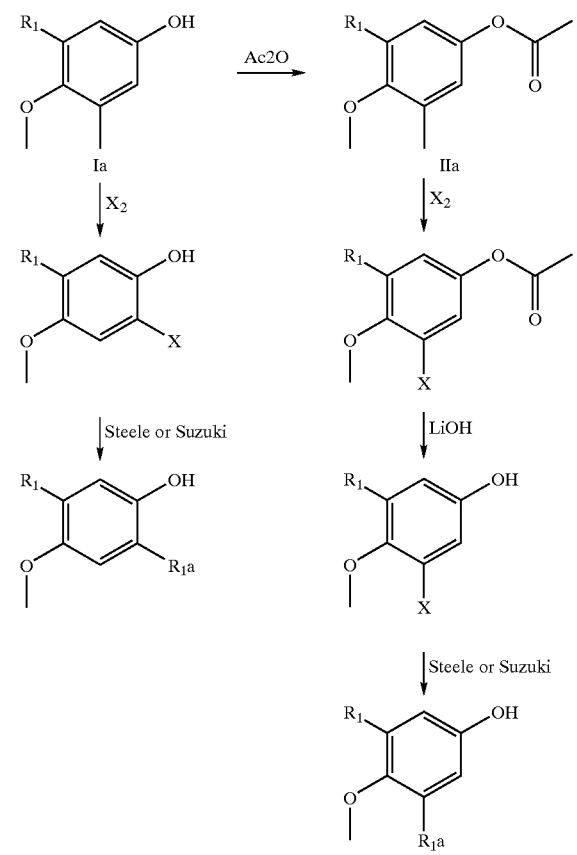

Alternatively, poly-substitutions can be achieved by halogenation of intermediate Ia or its acyl derivative, intermediate IIa, followed by hydrolysis. Conversion of the halogens (X) to an alkyl, aryl or heteroaryl may be achieved by subsequent Steele or Suzuki coupling reactions with tetraalkyltin or aryl boronic acid reagents.

of CHO to COOH and to N-substituted amide may be carried out by methods well known in the art, such as oxidation of the formyl group of intermediate 9 to form intermediate 10. Carbodiimide promoted coupling of an

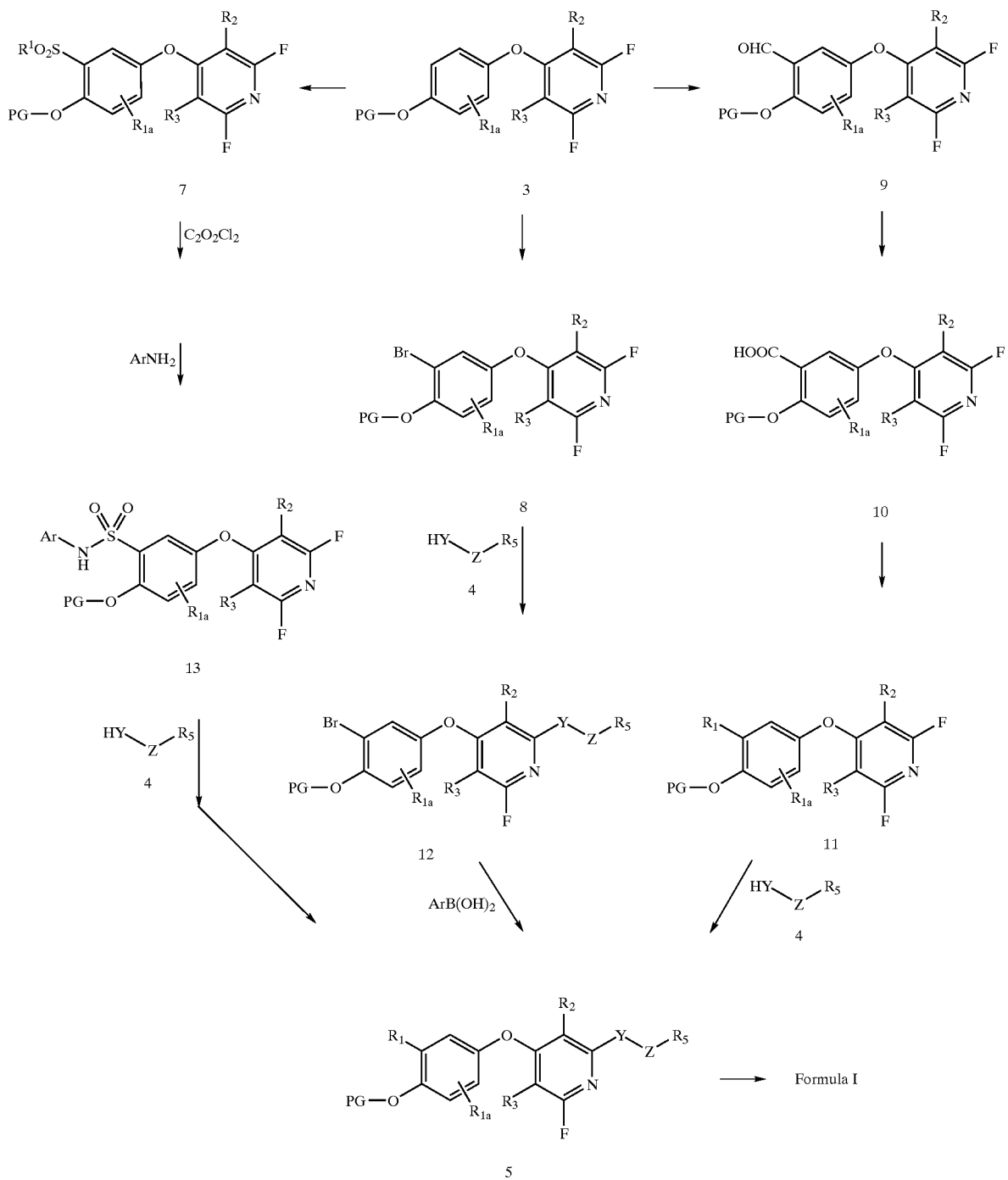

Scheme 2 depicts another general synthetic approach to produce the compounds of formula I wherein X=O in which the position adjacent (ortho) to O—PG ($R_1$=H) can be functionalized via sulfonation/sulfonylation, brominalion or formylation to provide intermediate 7, 8 and 9. Conversion amine with the resulting carboxylic acid of intermediate 10 provides intermediate 11 wherein $R_1$=an amide. Subsequent displacement of the 2-fluoro substituent of 11 with an amine or alkoxide 4, where Y=NH or O, as described in the description of Scheme 1, provides intermediate 5. Displacement of the 2-fluoro substituent of 8 with 4 provides 12.

Subsequent Suzuki coupling of the aryl bromide 12 with substituted phenylboronic acid provides 5 wherein $R_1$=Aryl.

Chloronation of the aryl sulfonic acid 7 wherein $R^1$=OH, followed by addition of an amine or aniline provides the aryl sulfonamide intermediate 13. Displacement of the 2 fluoro substituent of 13 or 7 wherein $R^1$=Ar, with 4 provides 5 wherein $R_1$=sulfonamide or sulfone.

SCHEME 2b

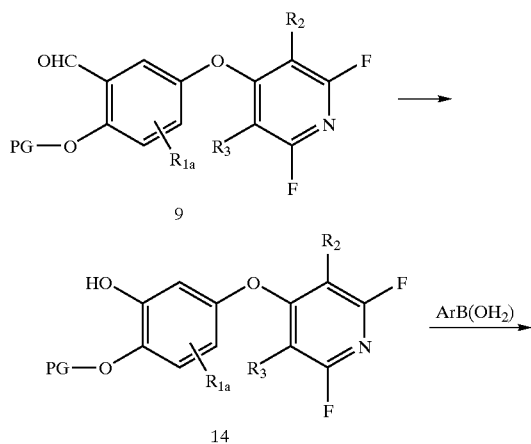

9

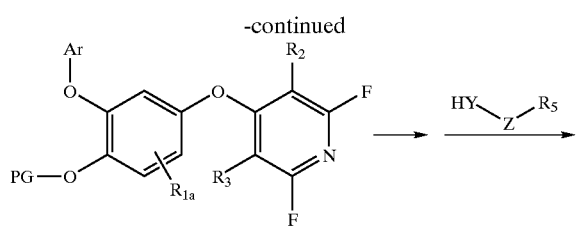

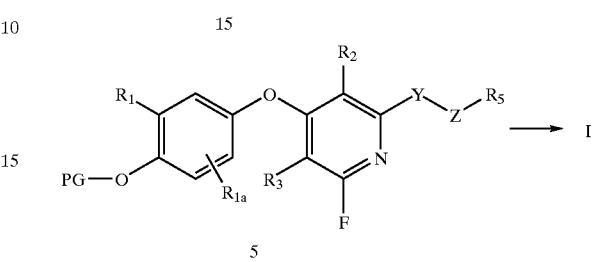

5

Scheme 2b depicts Baeyer-Villiger oxidation of the intermediate 9 followed by hydrolysis provides 14. Treatment of 14 with aryl boronic acids under Evan's conditions (see D. A. Evans et al., Tetrahedron Lett., 39, 2937–2940, 1998) provides intermediate 15. Subsequent displacement of the 2-fluoro substituent of 15 with 4 provides 5 wherein $R_1$=aryloxy. Further protecting group and functional group manipulation of the intermediate 5 will provide the desired compounds of formula I where X is oxygen.

SCHEME 3

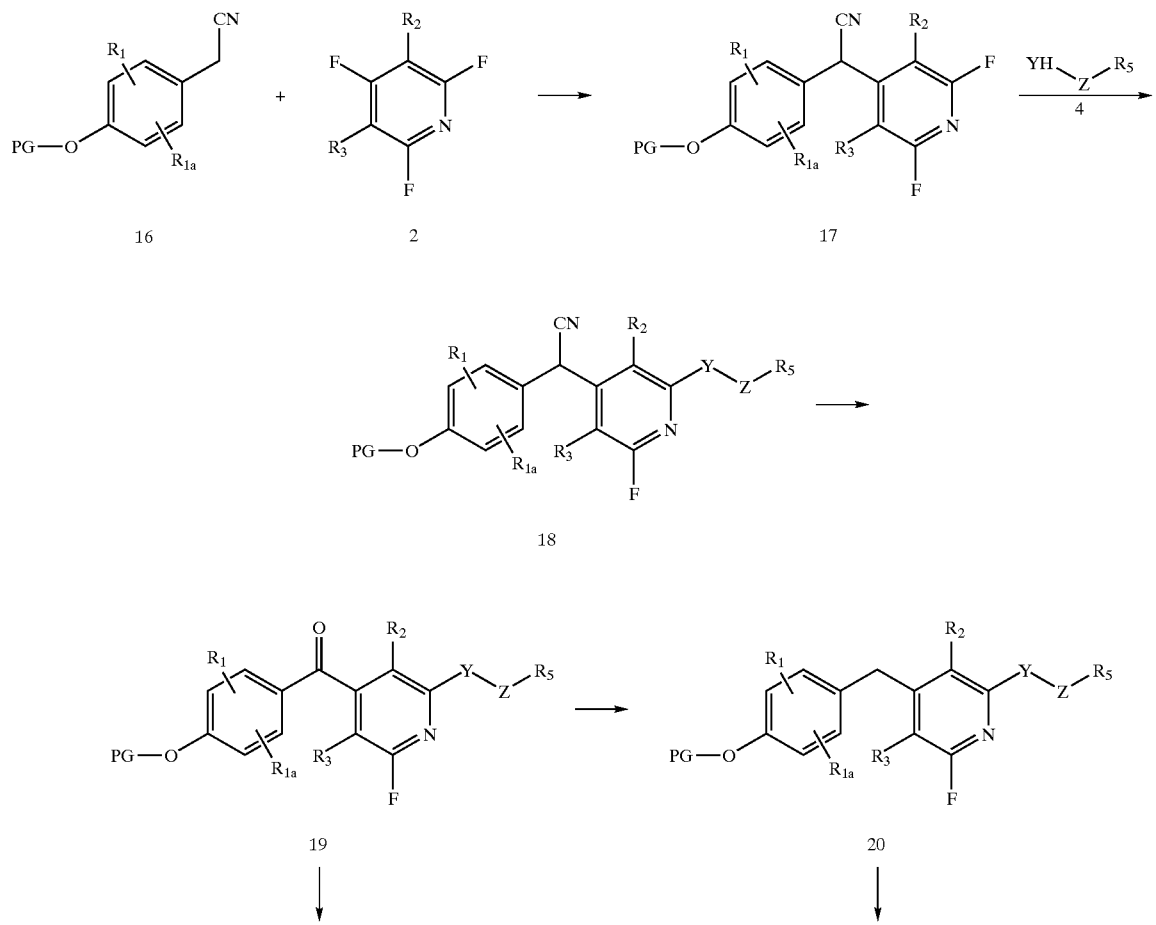

-continued

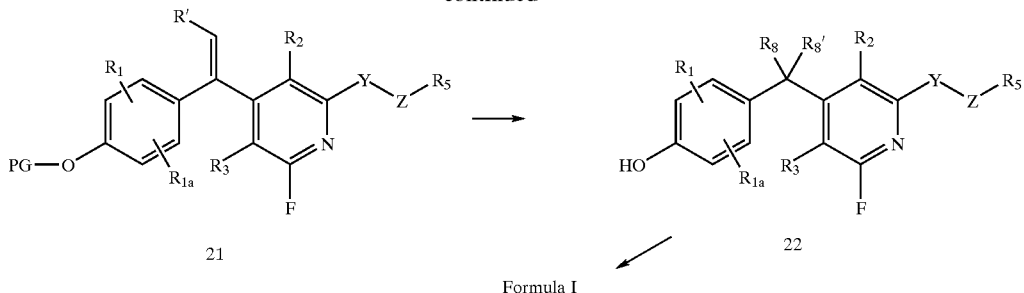

Formula I

Alternatively, compounds of formula I in which X is $CR_8R_8'$ or CO may be prepared as shown in Scheme 3. Conversion of 2 to 18 may be achieved via displacement of the 4-fluoro substituent of 2 with 16 followed by displacement of the 2-fluoro substituent of 17 with nucleophile 4. Oxidation of 18 provides 19. Deprotection and functional group manipulation of 19 provides compounds of formula I wherein X is CO. Alternatively, reductive deoxygenation of 19 affords 20. Deprotection of 20 provides intermediate 22. Alternatively, Wittig olefination of 19 provides intermediate 21. Hydrogenation, deprotection and functional group manipulation of 21 provides intermediate 22. Deprotection and functional group manipulation of 22 provides compounds of formula I where X is $CR_8R_8'$.

Further methods applicable to the synthesis of compounds of formula I in which X=O and $R_2$ and $R_3$ are independently varied as hydrogen, halogen and alkyl are described in Li et al., WO 99/00353.

All stereoisomers of the compounds of the instant invention are contemplated, either in admixture or in pure or substantially pure form. The compounds of the present invention can have asymmetric centers at any of the carbon atoms including any one of the R substitutents. Consequently, compounds of formula I can exist in enantiomeric or diasteromeric forms or in mixtures thereof. The processes for preparation can utilize racemates, enantiomers or diastereomers as starting materials. When diastereomeric or enantiomeric products are prepared, they can be separated by conventional methods. For example, chromatographic or fractional crystallization.

Utilities & Combinations

A. Utilities

The compounds of the present invention are thyroid receptor ligands, and include compounds which are, for example, selective agonists, partial agonists, antagonists or partial antagonists of the thyroid receptor. Preferably compounds of the present invention possess activity as agonists of the thyroid receptor, preferably selective agonists of the thyroid receptor-beta, and may be used in the treatment of diseases or disorders associated with thyroid receptor activity. In particular, compounds of the present invention may be used in the treatment of diseases or disorders associated with metabolism dysfunction or which are dependent upon the expression of a $T_3$ regulated gene.

Accordingly, the compounds of the present invention can be administered to mammals, preferably humans, for the treatment of a variety of conditions and disorders, including, but not limited to hypothyroidism; subclinical hyperthyroidism; non-toxic goiter; atherosclerosis; thyroid hormone replacement therapy (e.g., in the elderly); malignant tumor cells containing the thyroid receptor; papillary or follicular cancer; maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); accelerating healing of complicated fractures, e.g. distraction osteogenesis; in joint replacement; eating disorders (e.g., anorexia); treatment of obesity and growth retardation associated with obesity; treatment of depression, nervousness, irritability and stress; treatment of reduced mental energy and low selfesteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of hyperinsulinemia; stimulation of osteoblasts, bone remodeling and cartilage growth; regulation of food intake; treatment of insulin resistance, including NIDDM, in mammals (e.g., humans); treatment of insulin resistance in the heart; treatment of congestive heart failure; treatment of musculoskeletal impairment (e.g., in the elderly); improvement of the overall pulmonary function; skin disorders or diseases, such as glucocorticoid induced dermal atrophy, including restoration of dermal atrophy induced by topical glucocorticoids, and the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocdrticoids, restoration/prevention of atrophy in the respiratory system induced by local treatment with glucocorticoids, UV-induced dermal atrophy, dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other modulators and/or ligands of the thyroid receptor or other suitable therapeutic agents useful in the treatment of the aforementioned disorders including: anti-diabetic agents; anti-osteoporosis agents; anti-obesity agents; growth promoting agents (including growth hormone secretagogues); anti-inflammatory agents; anti-anxiety agents; anti-depressants; anti-hypertensive agents; cardiac glycosides; cholesterol/lipid lowering agents; appetite suppressants; bone resorption inhibitors; thyroid mimetics (including other thyroid receptor agonists); anabolic agents; and anti-tumor agents.

Examples of suitable anti-diabetic agents for use in combination with the compounds of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1–34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

A further use of the compounds of this invention is in combination with sterioidal or non-steroidal progesterone receptor agonists ("PRA"), such as levonorgestrel, medroxyprogesterone acetate (MPA).

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

For the treatment of skin disorders or diseases as described above, the compounds of the present invention may be used alone or optionally in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable cardiac glycosides for use in combination with the compounds of the present invention include digitalis and ouabain.

Examples of suitable cholesterol/lipid lowering agents for use in combination with the compounds of the present invention include HMG-COA reductase inhibitors, squalene synthetase inhibitors, fibrates, bile acid sequestrants, ACAT inhibitors, MTP inhibitors, lipooxygenase inhibitors, an ileal $Na^+$/bile acid cotransporter inhibitor, cholesterol absorption inhibitors, and cholesterol ester transfer protein inhibitors (e.g., CP-529414).

MTP inhibitors which may be employed herein in combination with one or more compounds of formula I include MTP inhibitors as disclosed in U.S. Pat. Nos. 5,595,872, 5,739,135, 5,712,279, 5,760,246, 5,827,875, 5,885,983 and 5,962,440 all incorporated herein by reference.

A preferred MTP inhibitor is 9-[4-[4-[[2-(2,2,2-Trifluoroethoxy)benzoyl]amino]-1-piperidinyl]butyl]-N-(2, 2,2-trifluoroethyl)-9H-fluorene-9-carboxamide

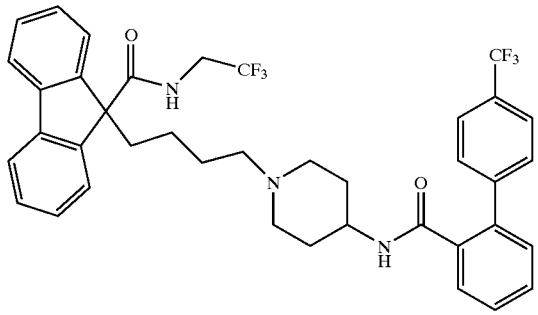

The HMG CoA reductase inhibitors which may be employed in combination with one or more compounds of formula I include mevastatin and related compounds as disclosed in U.S. Pat. No. 3,983,140, lovastatin (mevinolin) and related compounds as disclosed in U.S. Pat. No. 4,231, 938, pravastatin and related compounds such as disclosed in U.S. Pat. No. 4,346,227, simvastatin and related compounds as disclosed in U.S. Pat. Nos. 4,448,784 and 4,450,171. Further HMG CoA reductase inhibitors which may be employed herein include fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Pat. No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0,142,146 A2, as well as other known HMG CoA reductase inhibitors.

The squalene synthetase inhibitors which may be used in combination with the compounds of the present invention include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinylmethyl) phosphonates, terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J. A. C. S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, as well as other squalene synthetase inhibitors as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

Bile acid sequestrants which may be used in combination with the compounds of the present invention include cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

ACAT inhibitors suitable for use in combination with compounds of the invention include ACAT inhibitors as described in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

The aforementioned patents and patent applications are incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a hypolypidemic agent, an antidepressant, a bone resorption inhibitor and/or an appetite suppressant, the compounds of formula I may be employed in a weight ratio to the additional agent within the range from about 500:1 to about 0.005:1, preferably from about 300:1 to about 0.01:1.

Where the antidiabetic agent is a biguanide, the compounds of formula I may be employed in a weight ratio to biguanide within the range from about 0.01:1 to about 100:1, preferably from about 0.5:1 to about 2:1.

The compounds of formula I may be employed in a weight ratio to a glucosidase inhibitor within the range from about 0.01:1 to about 100:1, preferably from about 0.5:1 to about 50:1.

The compounds of formula I may be employed in a weight ratio to a sulfonylurea in the range from about 0.01:1 to about 100:1, preferably from about 0.2:1 to about 10:1.

The compounds of formula I may be employed in a weight ratio to a thiazolidinedione in an amount within the range from about 0.01:1 to about 100:1, preferably from about 0.5:1 to about 5:1.

The thiazolidinedione may be employed in amounts within the range from about 0.01 to about 2000 mg/day, which may optionally be administered in single or divided doses of one to four times per day.

Further, where the sulfonylurea and thiazolidinedione are to be administered orally in an amount of less than about 150 mg, these additional agents may be incorporated into a combined single tablet with a therapeutically effective amount of the compounds of formula I.

Metformin, or salt thereof, may be employed with the compounds of formula I in amounts within the range from about 500 to about 2000 mg per day, which may be administered in single or divided doses one to four times daily.

The compounds of formula I may be employed in a weight ratio to a PPAR-alpha agonist, a PPAR-gamma agonist, a PPAR-alpha/gamma dual agonist, an SGLT2 inhibitor and/or an aP2 inhibitor within the range from about 0.01:1 to about 100:1, preferably from about 0.5:1 to about 5:1.

An MTP inhibitor may be administered orally with the compounds of formula I in an amount within the range of from about 0.01 mg/kg to about 100 mg/kg and preferably from about 0.1 mg/kg to about 75 mg/kg, one to four times daily.

A preferred oral dosage form, such as tablets or capsules, may contain the MTP inhibitor in an amount of from about 1 to about 500 mg, preferably from about 2 to about 400 mg, and more preferably from about 5 to about 250 mg; administered on a regimen of one to four times daily.

For parenteral administration, the MTP inhibitor may be employed in an amount within the range of from about 0.005 mg/kg to about 10 mg/kg and preferably from about 0.005 mg/kg to about 8 mg/kg, administered on a regimen of one to four times daily.

A HMG CoA reductase inhibitor may be administered orally with the compounds of formula I within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A squalene synthetase inhibitor may be administered with the compounds of formula I within the range of from about 10 mg to about 2000 mg and preferably from about 25 mg to about 200 mg.

A preferred oral dosage form, such as tablets or capsules, will contain the squalene synthetase inhibitor in an amount of from about 10 to about 500 mg, preferably from about 25 to about 200 mg.

The compounds of formula I of the invention can be administered orally or parenterally, such as subcutaneously or intravenously, as well as by nasal application, rectally or sublingually to various mammalian species known to be subject to such maladies, e.g., humans, in an effective amount within the dosage range of abut 0.01 $\mu$g/kg to about 1000 $\mu$g/kg, preferably about 0.1 $\mu$g/kg to 100 $\mu$g/kg, more preferably about 0.2 $\mu$g/kg to about 50 $\mu$g/kg (or form about 0.5 to 2500 mg, preferably from about 1 to 2000 mg) in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The following working examples serve to better illustrate, but not limit, some of the preferred embodiments of the present invention.

EXAMPLE 1

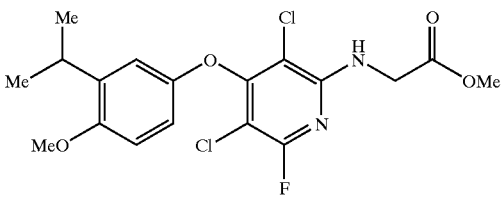

3,5-dichloro-2-fluoro-4-(3-isopropyl-4-methoxyphenoxy)-6-mathoxycarbonylmethylaminopyridine Compound 1a: 2-Isopropylanisole

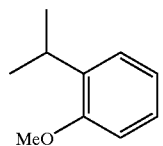

To a solution of 2-isopropylphenol (30 g, 220.3 mmol) in $CH_2Cl_2$ (300 mL) was added tetrabutylammonium hydrogen sulfate (7.5 g, 22.1 mmol). After the entire solid was dissolved, a solution of potassium hydroxide (61.8 g, 1.1 mol in 300 mL $H_2O$) was added to the previous mixture. After 15 minutes of stirring, methyl iodide (47 g, 20.6 mL, 331 mmol) was added. The mixture was left to stir overnight (ca. 15 hours). The organic layer was separated and then washed with brine (2×100 mL), dried ($Na_2SO_4$), filtered and concentrated in vacuo. The solid material in the concentrate was removed by filtration. The precipitate was washed with hexane (100 mL). The filtrate was concentrated in vacuo to give 32.15 g of yellow oil as a crude product. The crude product was filtered through a pad of silica gel (250 g) and washed with 5% EtOAc in hexane to give 30.7 g (93%) of compound 1a as a colorless oil.

$^1$H NMR (500 MHz, $CDCl_3$, δ) 7.21 (d, 1H, J=7.7 Hz), 7.16 (t, 1H, J=7.7 Hz), 6.92 (t, 1H, J=7.7 Hz), 6.84 (d, 1H, J=8.3 Hz), 3.82 (s, 3H), 3.27 (septet, 1H, 7 Hz), 1.205 (d, 6H, J=6.6 Hz).

Compound 1b: 3-Isopropyl-4-methoxybenzaldehyde

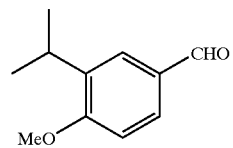

To a 3-necked flask containing 2-isopropylanisole (14 g, 93.2 mmol) was added phosphorus oxychloride (57.6 g, 35 mL, 375.5 mmol). The mixture was heated to 80° C. and maintained at this temperature while N,N-dimethylfromamide (27.4 g, 29 mL, 374.5 mmol) was slowly added using an addition funnel. After the DMF addition, the mixture was heated to 95° C. and maintained at this temperature overnight (ca. 19 h). After cooling to RT, the mixture was poured into a flask containing ice and $H_2O$ (200 mL) and stirred for ca. 15 min. The product was partitioned with EtOAc (300 mL) and brine (200 mL). The EtOAc extract was separated, washed with brine (2×150 mL), dried ($Na_2SO_4$), filtered and concentrated in vacuo. The crude product was purified by chromatography (250 g silica gel, 10% EtOAc in hexane) to afford 13 g (78%) of compound 1 b as a yellow oil.

¹H NMR (500 MHz, CDCl₃, δ) 9.87 (s, 1H), 7.755 (d, 1H, J=1.6 Hz), 7.695 (dd, 1H, J=8.8 Hz, 1.6 Hz ), 6.94 (d, 1H, J=8.3 Hz), 3.91 (s, 3H), 3.31 (septet, 1H, 7 Hz), 1.225 (d, 6H, J=7.1 Hz).

Compound 1c: 3-Isopropyl-4-methoxyphenol

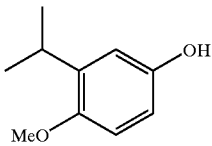

To a solution of 3-isopropyl-4-methoxybenzaldehyde (12.5 g, 70 mmol) in MeOH(140 mL) was added concentrated sulfuric acid (1.2 mL) followed by dropwise addition of 30% by wt aqueous hydrogen peroxide(6 g, 20 mL, 176 mmol). The mixture was left to stir at ambient room temperature. After 3 hours, the mixture was concentrated in vacuo to about ⅓ of the reaction volume. The concentrate was partitioned between EtOAc (100 mL) and brine (50 mL). The EtOAc extract was washed with brine (50 mL), dried (Na₂SO₄), filtered and concentrated in vacuo to give 13.5 g of dark oil as crude product. The crude product was purified by chromatography (250 g silica gel, 10% EtOAc in hexane) to afford 10.1 g (86%) of compound 1c as a thick oil that eventually solidified.

¹H NMR (500 MHz, CDCl₃, δ) 6.715 (d, 1H, J=2.8 Hz), 6.705 (d, 1H, J=3.3 Hz), 6.595 (dd, 1H, J=8.8 Hz, 3.3 Hz), 4.44 (s, 1H), 3.77 (s, 3H), 3.27 (septet, 1H, 7 Hz), 1.175 (d, 6H, J=7.2 Hz).

Compound 1d: 3,5-Dichloro-2,6-difluoro-4-(3-isopropyl-4-methoxyphenoxy)pyridine

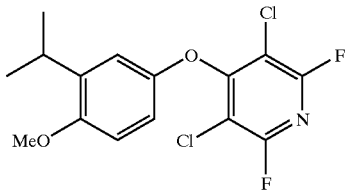

To a solution of 3-isopropyl-4-methoxyphenol (0.68 g) and 3,5-dichloro-2,4,6-trifluoropyridine (0.84 g) in DMF (4.0 mL) was added potassium carbonate powder (0.67 g) in one portion. The resulting mixture was stirred at ambient temperature for 1 h. The reaction mixture was diluted with brine, extracted with ethyl acetate (50 mL×3). The combined organic layers were washed with brine (100 mL×3), dried (Na₂SO₄), and concentrated in vacuo to afford compound 1d as an off-white solid (1.15 g, 80%).

¹H NMR (500 MHz, CDCl₃, δ) 6.87 (d, 1H,J=3.3 Hz), 6.73 (d, 1H, J=8.8 Hz), 6.55(dd,1H, J=8.8 Hz, 3.3 Hz), 3.80 (s, 3H), 3.29 (septet, 1H, 7 Hz), 1.18 (d, 6H, J=7.2 Hz).

Compound 1e: 3,5-Dichloro-2-fluoro-4-(3-isopropyl-4-methoxyphenoxy)-6-methoxycarbonylmethyl-aminopyridine

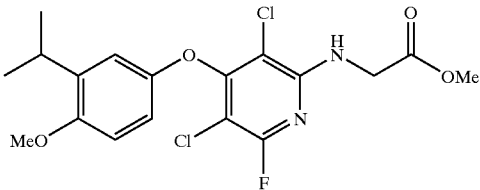

To a solution of 3,5-dichloro-2,6-difluoro-4-(3-isopropyl-4-methoxyphenoxy)pyridine. (584 mg) and glycine methyl ester hydrochloric acid (220 mg) in DMF (5.0 mL) was added potassium carbonate powder (500 mg) in one portion. The resulting mixture was stirred at ambient temperature for 20 hours. The reaction mixture was diluted with brine, extracted with ethyl acetate (50 mL×2). The combined organic layers were washed with brine (50 mL×3), dried (Na₂SO₄), and concentrated. Chromatography with ethyl acetate-hexanes (0–50% gradient elution) afforded the title compound as a colorless oil (434 mg, 62%).

¹H NMR (500 MHz, CDCl₃, δ) 6.89 (d, 1H, J=3.3 Hz), 6.71 (d, 1H, J=8.8 Hz), 6.54 (dd, 1H, J=8.8 Hz, 3.3 Hz), 5.70 (br. t, 1H, J=5 Hz), 4 21 (d, 2H, J=5 Hz), 3.80 (s, 3H), 3.78 (s, 3H), 3.28 (septet, 1H, 7 Hz), 1.18 (d, 6H, J=7.2 Hz).

EXAMPLE 2

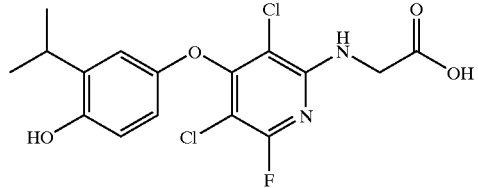

3,5-Dichloro-2-fluoro-4-(3-isopropyl-4-hydroxyphenoxy)-6-hydroxycarbonylmethylaminopyridine To a solution of 3,5-dichloro-2-fluoro-4-(3-isopropyl-4-methoxyphenoxy)-6-methoxycarbonyl-methyl-aminopyridine (100 mg) in CH₂Cl₂ was added a solution of BBr₃ in CH₂Cl₂ (1 mL, 1.0 M) at ambient temperature. The resulting mixture was stirred for 30 min., poured to stirring water (50 mL), extracted with CH₂Cl₂ (20 mL×3) from water, dried (Na₂SO₄) and concentrated to dryness under reduced pressure. The residue was dissolved in THF:MeOH:H₂O=3:1:1 (5 mL), treated with a solution of LiOH in water (1 mL, 1.0 M) and stirred at ambient temperature for 30 min. The reaction mixture was diluted with a 1.0 M solution of HCl (50 mL), extracted with ethyl acetate (50 mL×3), dried (Na₂SO₄) and concentrated under reduced pressure. Purification by HPLC provided the title compound as a white solid (80 mg).

¹H NMR (500 MHz, CDCl₃, δ) 6.85 (d, 1H, J=3.3 Hz), 6.64 (d, 1H, J=8.8 Hz), 6.47 (dd, 1H, J=8.8 Hz, 3.3 Hz), 5.63 (br. t, 1H, J=5 Hz), 4 29 (d, 2H,. J=5 Hz), 3.17 (septet, 1H, 7 Hz), 1.23 (d, 6H, J=7.2 Hz).

Examples 3–13 were prepared by a similar procedure as described in Example 1, but with the following variations:

EXAMPLE 3

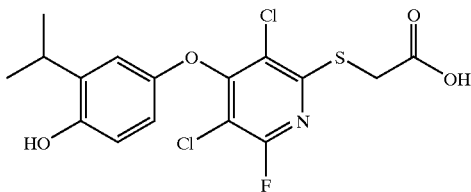

3,5-Dichloro-2-fluoro-4-(3-isopropyl-4-hydroxyphenoxy)-6-hydroxycarbonylmethylthiopyridine By use of methyl mercaptoacetate in place of glycine methyl ester for the preparation of Compound 1e followed by deprotection as described for example 2.

(M−H)⁻=403.87; molecular weight (MW)=406.26.

EXAMPLE 4

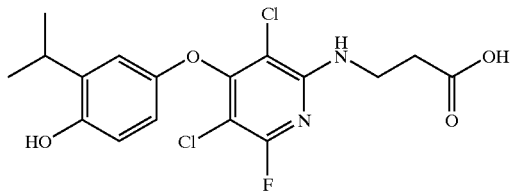

3,5-Dichloro-2-fluoro-4-(3-isopropyl-4-hydroxyphenoxy)-6-(2-hydroxycarbonylethylamino)pyridine By use of β-alanine methyl ester in place of glycine methyl ester for the preparation of Compound 1e followed by deprotection as described for example 2.

(M−H)⁻=400.9; MW=403.24.

EXAMPLE 5

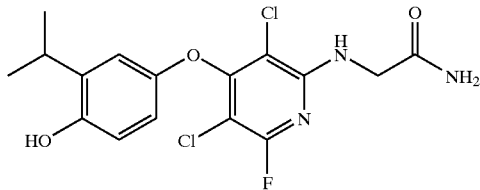

3,5-Dichloro-2-fluoro-4-(3-isopropyl-4-hydroxyphenoxy)-6-(2-aminocarbonylmethylamino)pyridine By use of glycinamide in place of glycine methyl ester for the preparation of Compound 1e followed by deprotection as described for example 2.

(M−H)⁻=386; MW=388.23.

EXAMPLE 6

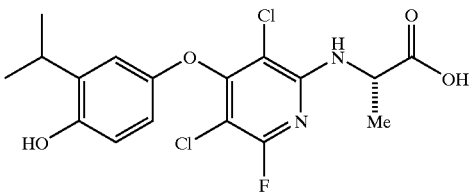

3,5-Dichloro-2-fluoro-4-(3-isopropyl-4-hydroxyphenoxy)-6-(1-methyl-1-hydroxycarbonyl)methylaminopyridine By use of 1-alanine methyl ester in place of glycine methyl ester ester for the preparation of Compound 1e followed by deprotection as described for example 2. Satisfactory ¹H-NMR and MS data were obtained.

(M−H)⁻=401; MW=403.24.

EXAMPLE 7

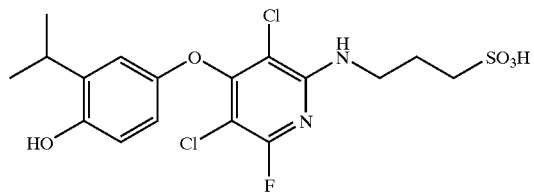

3,5-Dichloro-2-fluoro-4-(3-isopropyl-4-hydroxyphenoxy)-6-(3-hydroxysulfonylpropylamino)pyridine By use of 3-aminopropylsulfonic acid in place of glycine methyl ester ester for the preparation of Compound 1e followed by deprotection as described for example 2.

(M−H)⁻=451; MW=453.32.

EXAMPLE 8

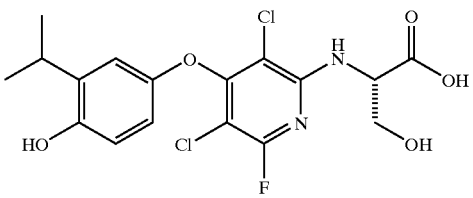

3,5-Dichloro-2-fluoro-4-(3-isopropyl-4-hydroxyphenoxy)-6-(1-hydroxycarbonyl-2-hydroxyethylamino)pyridine By use of 1-serine methyl ester in place of glycine methyl ester for the preparation of Compound 1e followed by deprotection as described for example 2.

(M+H)⁺=417; MW=419.24.

EXAMPLE 9

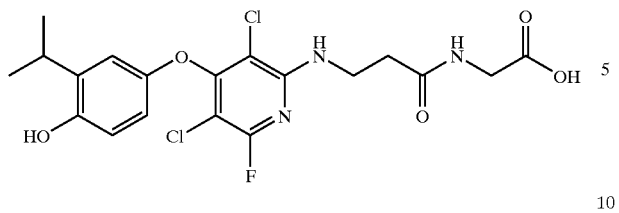

3,5-Dichloro-2-fluoro-4-(3-isopropyl-4-hydroxyphenoxy)-6-(3-hydroxycarbonylmethylamino-3-oxopropylanino)pyridine By use of β-alanyl-glycine in place of glycine methyl ester for the preparation of Compound 1e followed by deprotection as described for example 2.

(M−H)⁻=458; MW=460.29.

EXAMPLE 10

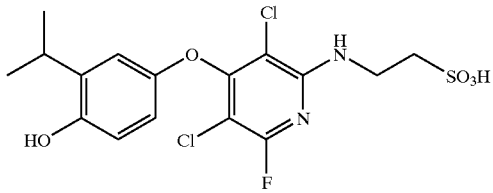

3,5-Dichloro-2-fluoro-4-(3-isopropyl-4-hydroxyphenoxy)-6-(2-hydroxysulfonylethylamino)pyridine By use of 2-aminoethylsulfonic acid in place of glycine methyl ester for the preparation of Compound 1e followed by deprotection as described for example 2.

(M−H)⁻=439.29; MW=437.

EXAMPLE 11

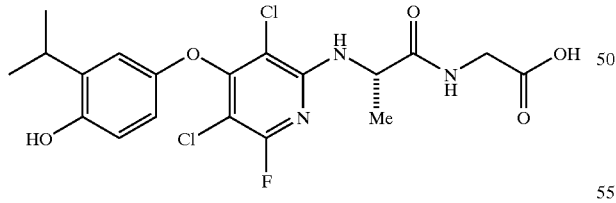

3,5-Dichloro-2-fluoro-4-(3-isopropyl-4-hydroxyphenoxy)-6-(2-hydroxycarbonylmethylamino-2-oxo-1-methylethylamino)-pyridine By use of 1-alanyl-glycine methyl ester in place of glycine methyl ester for the preparation of Compound 1e followed by deprotection as described for example 2.

(M−H)⁻=458; MW=560.29.

EXAMPLE 12

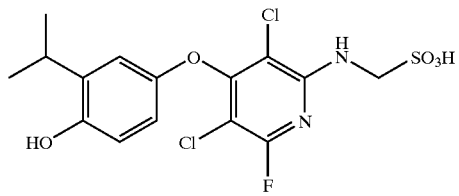

3,5-Dichloro-2-fluoro-4-(3-isopropyl-4-hydroxyphenoxy)-6-hydroxysulfonylmethylaminopyridine By use of aminomethanesulfonic acid in place of glycine methyl ester for the preparation of Compound 1e followed by deprotection as described for example 2.

(M−H)⁻=423; MW=425.27.

EXAMPLE 13

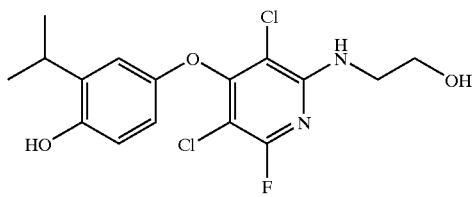

3,5-Dichloro-2-fluoro-4-(3-isopropyl-4-hydroxyphenoxy)-6-(2-hydroxyethylamino)pyridine By reduction of the methyl ester of 3,5-dichloro-2-fluoro-4-(3-isopropyl-4-hydroxyphenoxy)-6-hydroxycarbonyl-methylaminopyridine (example 2), with Dibal-H in THF.

(M−H)⁻=423; MW=425.27.

EXAMPLE 14

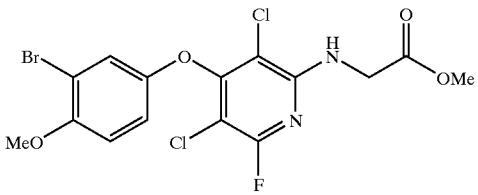

3,5-dichloro-2-fluoro-4-[3-brono-4-methoxy-phenoxy]-6-methoxycarbonylmethyl-aminopyridine
Compound 14a: 3-Ethylphenylboronic Acid

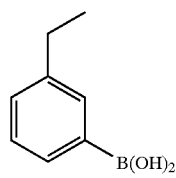

To a solution of 3-bromo-1-ethylbenzene (1.0 g) in THF (10 mL) at −78° C. under argon was added a solution of n-BuLi (2.5 M, 2.5 mL) in hexanes in dropwise fashion. The mixture was stirred at −78° C. for 10 min. and treated with 1.35 mL of tri-isopropylborate (neat) dropwise. The reaction mixture was allowed to warm up to 10° C. over a period of 3 hours while stirring. The mixture was then quenched carefully with 1 N HCl (100 mL) solution and extracted with ethyl acetate (100 mL×2). The combined organic layers were dried (Na$_2$SO$_4$) and concentrated under reduced pressure. Chromatography with ethyl acetate-hexanes (0–100% gradient elution) provided compound 14a as a white solid (0.4 g).

$^1$H NMR (500 MHz, CDCl$_3$, δ) 8.06 (m, 2H), 7.44 (m, 2H), 2.77 (q, 2H, J=7.0 Hz), 1.32 (t, 3H, J=7.0 Hz).

Compound 14b: 3,5-Dichloro-2,6-difluoro-4-(4-methoxy-phenoxy)pyridine

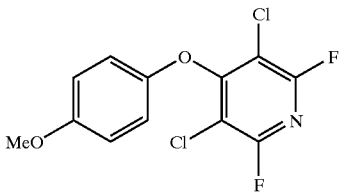

To a solution of 4-methoxyphenol (1.25 g) and 3,5-dichloro-2,4,6-trifluoropyridine (2.05 g) in DMF (10.0 mL) was added potassium carbonate powder (1.50 g) in one portion. The resulting mixture was stirred at ambient temperature for 3 hours. The reaction mixture was diluted with brine and extracted with ethyl acetate (100 mL×3). The combined organic layers were washed with brine (100 mL×3), dried (Na$_2$SO$_4$), and concentrated in vacuo to provide compound 14b as a white solid (3.0 g).

$^1$H NMR (500 MHz, CDCl$_3$, δ) 6.78 (m, 4H), 3.72 (s, 3H).

Compound 14c: 3,5-Dichloro-2,6-difluoro-4-(3-bromo-4-methoxy-phenoxy)pyridine

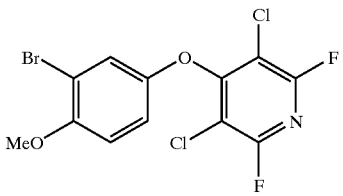

To a solution of 3,5-dichloro-2,6-difluoro-4-(4-methoxyphenoxy)pyridine (0.94 g) in CH$_2$Cl$_2$ (10 mL) was added neat bromine (1.0 g). The mixture was stirred at ambient temperature for 1 h. The solvent and excess bromine were removed under reduced pressure. Chromatography with ethyl acetate-hexanes (0–50% gradient elution) provides compound 14c (0.25 g).

$^1$H NMR (500 MHz, CDCl$_3$, δ) 7.14 (d, 1H, J 2.7 Hz), 6.82 (m, 2H), 3.87 (s, 3H).

Compound 14d: 3,5-Dichloro-2-fluoro-4-(3-bromo-4-methoxy-phenoxy)-6-methoxycarbonylmethylaminopyridine

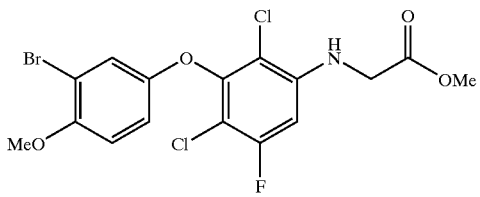

To a solution of 3,5-dichloro-2,6-difluoro-4-(3-bromo-4-methoxyphenoxy)pyridine (250 mg) and glycine methyl ester hydrochloric acid (150 mg) in DMF (2.0 mL) was added potassium carbonate powder (250 mg) in one portion. The resulting mixture was stirred at ambient temperature for 20 hours. The reaction mixture was diluted with brine and extracted with ethyl acetate (50 mL×2). The combined organic layers were washed with brine (50 mL×3), dried (Na$_2$SO$_4$) and concentrated. Chromatography with ethyl acetate-hexanes (0–50% gradient elution) provided the title compound as a white solid (253 mg).

$^1$H NMR (500 MHz, CDCl$_3$, δ) 7.13 (d, 1H, J 2.7 Hz), 6.82 (m, 2H), 5.70 (br. t, 1H, J=5.0 Hz), 4.24 (d, 2H, J=5 Hz), 3.87 (s, 3H), 3.81 (s, 3H).

EXAMPLE 15

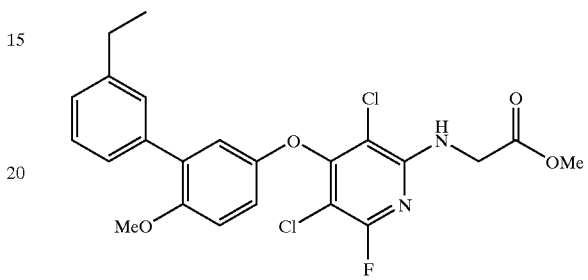

3,5-Dichloro-2-fluoro-4-[3-(3-ethylphenyl)-4-methoxy-phenoxy]-6-methoxycarbonylmethylaminopyridine To a solution of 3,5-dichloro-2,6-difluoro-4-(3-bromo-4-methoxyphenoxy)-6-methoxycarbonyl-methylaminopyridine (253 mg) and 3-ethylphenylboronic acid (100 mg) in THF (10.0 mL) was added a solution of sodium carbonate (2.0 M in water, 1.0 mL). The resulting mixture was degassed with argon, treated with tetrakis (triphenylphosphine) palladium (30 mg) and stirred at reflux in dark for 18 hours. Cooled reaction mixture was diluted with brine, neutrolized with 1 N HCl and extracted with ethyl acetate (50 mL×3). The combined organic layers were dried (Na$_2$SO$_4$) and concentrated. Chromatography with ethyl acetate-hexanes (0–50% gradient elution) afforded the title compound as a light yellow oil (180 mg).

$^1$H NMR (500 MHz, CDCl$_3$, δ) 7.32 (m, 3H), 7.19 (m, 1H), 6.90 (m, 2H), 6.82 (m, 1H), 5.69 (br. t, 1H, J=5 Hz), 4 21 (d, 2H, J=5 Hz), 3.80 (s, 3H), 3.78 (s, 3H), 2.69 (q, 2H, 7 Hz), 1.27 (t, 3H, J=7 Hz).

EXAMPLE 16

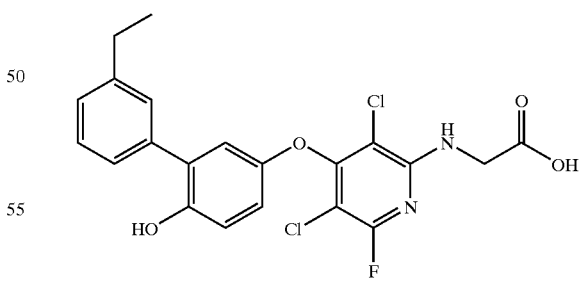

3,5-Dichloro-2-fluoro-4-[3-(3-ethylphenyl)-4-hydroxy-phenoxy]-6-hydroxycarbonylmethylaminopyridine To a solution of 3,5-dichloro-2-fluoro-4-[3-(3-ethylphenyl)-4-methoxyphenoxy]-6-methoxycarbonyl-methyl-aminopyridine (50 mg) in CH$_2$Cl$_2$ was added a solution of BBr$_3$ in CH$_2$Cl$_2$ (0.5 mL, 1.0 M) at ambient temperature. The resulting mixture was stirred for 30 min. The reaction mixture was diluted with a 1.0 M solution of HCl (50 mL), extracted with ethyl acetate (50 mL×3), dried (Na$_2$SO$_4$) and concentrated under reduced pressure. Purification by HPLC afforded the title compound as a yellow oil (32 mg).

$^1$H NMR (500 MHz, CDCl$_3$, δ) 7.41 (m, 1H), 7.26 (m, 3H), 6.92 (m, 1H), 6.80 (m, 2H), 5.63 (br. t, 1H, J=5 Hz), 5.18 (br. s, 2H), 4 29 (d, 2H, J=5 Hz), 2.70 (q, 2H, 7 Hz), 1.27 (t, 3H, J=7 Hz).

Examples 17–21 were prepared by a similar procedure as described in Examples 14 through 16, but with the following variations.

EXAMPLE 17

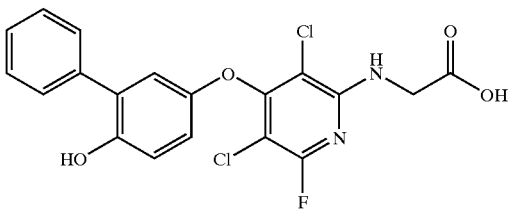

3,5-Dichloro-2-fluoro-4-(3-phenyl-4-hydroxyphenoxy)-6-hydroxycarbonylmethylaminopyridine By use of phenylboronic acid in place of 3-ethylphenylboronic acid in example 15 followed by deprotection as described for example 16.

(M–H)$^-$=421; MW=423.23.

EXAMPLE 18

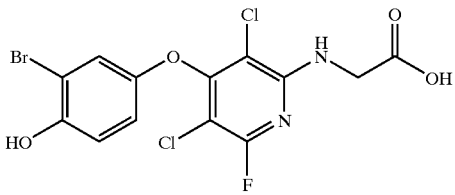

3,5-Dichloro-2-fluoro-4-[3-(3-bromo-4-hydroxyphenoxy]-6-hydroxycarbonylmethyl-aminopyridine By direct deprotection of 3,5-dichloro-2-fluoro-4-(3-bromo-4-methoxy-phenoxy)-6-methoxycarbonylmethylamino-pyridine using the procedure as described for example 16.

(M–H)$^-$=424.8; MW=426.03.

EXAMPLE 19

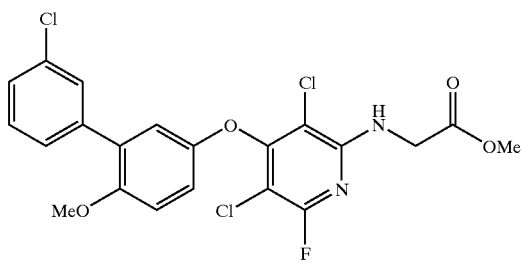

3,5-Dichloro-2-fluoro-4-[3-(3-chlorophenyl-4-methoxy-phenoxy)-6-(2-methoxycarbonylethylamino)pyridine By use of 3-chlorophenylboronic acid in place of 3-ethylphenylboronic acid in the procedure as described for example 15.

(M–H)$^-$=484.7; MW=485.73.

EXAMPLE 20

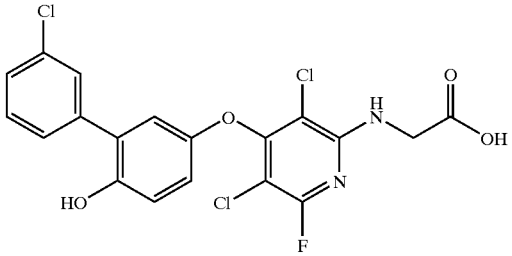

3,5-dichloro-2-fluoro-4-[3-(3-chlorophenyl)-4-hydroxy-phenoxy]-6-(hydroxycarbonylmethylamino)pyridine By direct deprotection of example 19 using the procedure as described for example 16.

(M–H)$^-$=455; MW=457.7.

EXAMPLE 21

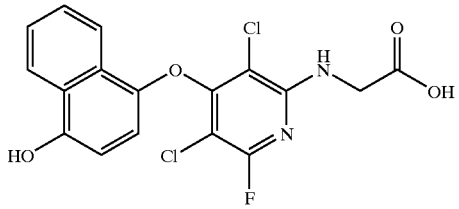

3,5-Dichloro-2-fluoro-4-(4-hydroxynaphthoxy)-6-hydroxycarbonylmethylanino-pyridine By use of 4-methoxynaphthol in place of 4-methoxyphenol using the procedure as described to prepare compound 14b followed by deprotection as described for example 2.

(M–H)$^-$=395; MW=397.19.

EXAMPLE 22

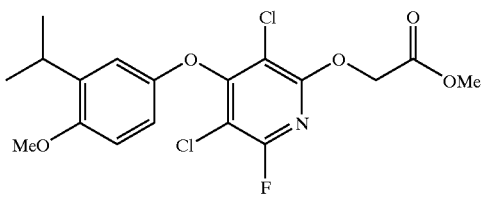

3,5-Dichloro-2-fluoro-4-(3-isopropyl-4-methoxyphenoxy)-6-methoxycarbonylmethoxypyridine To a solution of 3,5-dichloro-2,6-difluoro-4-(3-isopropyl-4-methoxyphenoxy)pyridine (100 mg) and methyl glycolate (neat, 25 µl) in THF (2.0 mL) was added a 60% oil dispersion of sodium hydride (10 mg) in one portion. The resulting mixture was stirred at ambient temperature for 30 min. The reaction mixture was diluted with brine, neutralized with 1 N HCl, extracted with $CH_2Cl_2$ (50 mL×2), dried ($Na_2SO_4$) and concentrated in vacuo to afford the title compound as a colorless oil (120 mg).

$^1$H NMR (500 MHz, $CDCl_3$, δ) 6.87 (d, 1H, J=2.7 Hz), 6.71 (d, 1H, J=8.8 Hz), 6.52 (dd, 1H, J=8.8 Hz, 2.7 Hz), 4 94 (s, 2H), 3.78 (s, 3H), 3.76 (s, 3H), 3.28 (septet, 1H, 7 Hz), 1.18 (d, 6H, J=7 Hz).

EXAMPLE 23

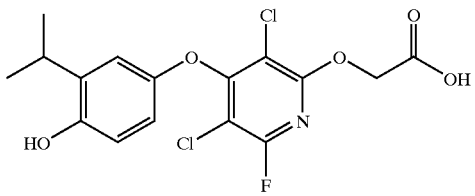

3,5-Dichloro-2-fluoro-4-(3-isopropyl-4-hydroxyphenoxy)-6-hydroxycarbonylmethoxypyridine To a solution of 3,5-dichloro-2-fluoro-4-(3-isopropyl-4-methoxyphenoxy)-6-methoxycarbonylmethoxy-pyridine (120 mg) in $CH_2Cl_2$ (3.0 mL) was added a solution of $BBr_3$ in $CH_2Cl_2$ (1 mL, 1.0 M) at ambient temperature. The resulting mixture was stirred for 2 h, poured to stirring water (50 mL), extracted with $CH_2Cl_2$ (20 mL×3) from water, dried ($Na_2SO_4$) and concentrated to dryness under reduced pressure. The residue was dissolved in THF:MeOH:$H_2O$= 3:1:1 (5 mL), treated with a solution of LiOH in water (1 mL, 1.0 M) and stirred at ambient temperature for 30 min. The reaction mixture was diluted with a 1.0 M solution of HCl (50 mL), extracted with ethyl acetate(50 mL×3), dried ($Na_2SO_4$) and concentrated under reduced pressure. Purification by HPLC afforded the title compound as a colorless oil (80 mg).

$^1$H NMR (500 MHz, $CDCl_3$, δ) 6.86 (d, 1H, J=2.7 Hz), 6.66 (d, 1H, J=8.8 Hz), 6.47 (dd, 1H, J=8.8 Hz, 2.7 Hz), 6.13 (br. s, 2H), 5.01 (s, 2H), 3.17 (septet, 1H, 7 Hz), 1.23 (d, 6H, J=7.2 Hz).

Examples 24–27 were prepared by a similar procedure as described in Example 22, but with the following variations.

EXAMPLE 24

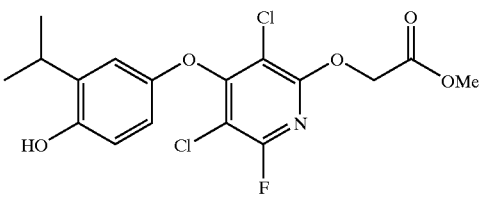

3,5-Dichloro-2-fluoro-4-(3-isopropyl-4-hydroxyphenoxy)-6-methoxycarbonylmethoxypyridine Obtained via purification of the intermediate before treatment with LiOH in the procedure for preparation of example 23.

(M–H)$^-$=401.8; MW=409.23.

EXAMPLE 25

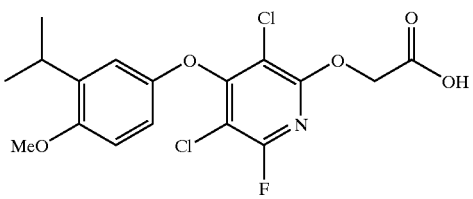

3,5-Dichloro-2-fluoro-4-(3-isopropyl-4-methoxyphonoxy)-6-hydroxycarbonylmethoxypyridine The title compound was obtained by LiOH hydrolysis of example 22.

(M–H)$^-$=401.8; MW=404.23.

EXAMPLE 26

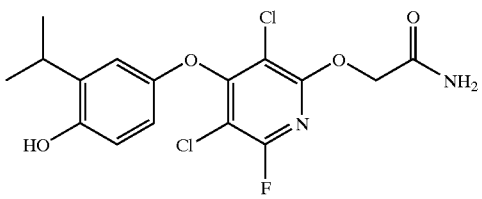

3,5-Dichloro-2-fluoro-4-(3-isopropyl-4-hydroxyphenoxy)-6-anlinocarbonylmethoxypyridine Prepared by use of glycolamide in place of methyl glycolate in the procedure for example 22, followed by $BBr_3$ deprotection, as described for example 23.

(M–H)$^-$=386.9; MW=389.21.

EXAMPLE 27

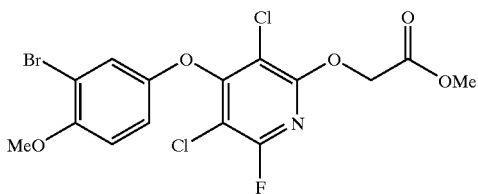

3,5-Dichloro-2-fluoro-4-(3-bromo-4-methoxyphenoxy)-6-methoxycarbonylmethoxypyridine Prepared by use of 4-(3-bromo-4-methoxyphenoxy)-3,5-dichloro-2,6-difluoropyridine in place of 3,5-dichloro-2,6-difluoro-4-(3-isopropyl-4-methoxyphenoxy)pyridine in the procedure described for example 22.

(M+H)$^+$=455.7; MW=455.07.

EXAMPLE 28

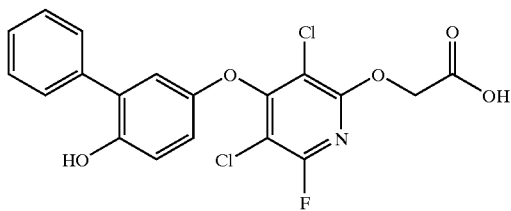

3,5-Dichloro-2-fluoro-4-(3-phenyl-4-hydroxyphenoxy)-6-hydroxycarbonylmethoxypyridine Prepared by use of 3,5-dichloro-2,6-difluoro-4-(3-bromo-4-methoxyphenoxy)-6-methoxycarbonylmethoxypyridine in place of 3,5-dichloro-2,6-difluoro-4-(3-bromo-4-methoxyphenoxy)-6-methoxycarbonyl-methylaminopyridine in the procedure described for example 17.

(M−H)$^-$=421.9; MW=.

EXAMPLE 29

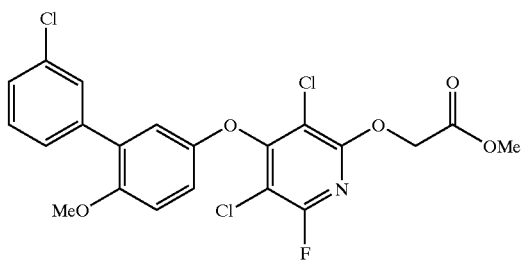

3,5-Dichloro-2-fluoro-4-[3-(3-chlorophenyl)-4-methoxy-phenoxy]-6-methoxycarbonylmethoxypyridine Prepared by use of 3,5-dichloro-2,6-difluoro-4-(3-bromo-4-methoxyphenoxy)-6-methoxycarbonylmethoxypyridine in place of 3,5-dichloro-2,6-difluoro-4-(3-bromo-4-methoxyphenoxy)-6-methoxycarbonyl-methylaminopyridine in the procedure described for example 19.

(M−H)$^-$=484.8; MW=486.71.

EXAMPLE 30

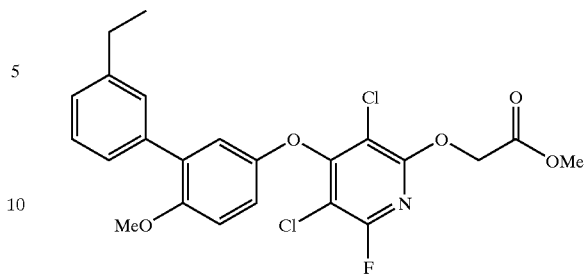

3,5-Dichloro-2-fluoro-4-[3-(3-ethylphenyl)-4-methoxy-phenoxy]-6-methoxycarbonylmethoxypyridine Prepared by use of 3,5-dichloro-2,6-difluoro-4-(3-bromo-4-methoxyphenoxy)-6-methoxycarbonylmethoxypyridine in place of 3,5-dichloro-2,6-difluoro-4-(3-bromo-4-methoxyphenoxy)-6-methoxycarbonyl-methylaminopyridine in the procedure described for example 15.

MW=480.32.

EXAMPLE 31

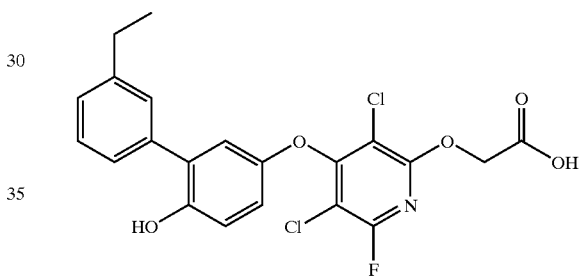

3,5-Dichloro-2-fluoro-4-[3-(3-ethylphenyl)-4-hydroxy-phenoxy]-6-hydroxycarbonylmethoxypyridine Prepared by deprotection of example 30 using the procedure described for example 16.

(M−H)$^-$=449.8; MW=452.27.

EXAMPLE 32

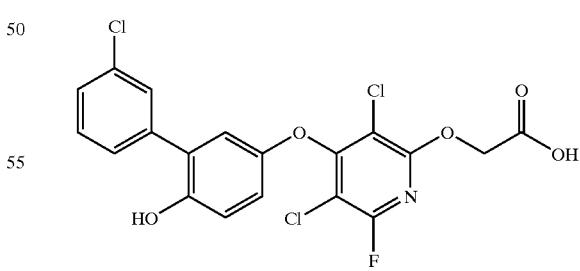

3,5-Dichloro-2-fluoro-4-[3-(3-chlorophenyl)-4-hydroxy-phenoxy]-6-hydroxycarbonylmethoxypyridine Prepared by deprotection of example 29 using the procedure described for example 20.

(M−H)$^-$=457.5; MW=458.66.

EXAMPLE 33

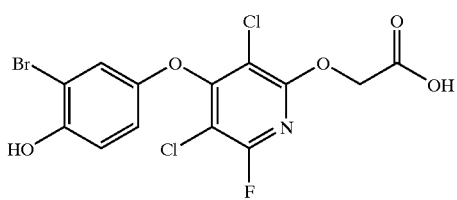

3,5-Dichloro-2-fluoro-4-[3-bromo-4-hydroxyphenoxy]-6-hydroxycarbonylmethoxypyridine Prepared by deprotection of example 27 using the procedure described for example 16.

(M−H)⁻=425.72; MW=427.01.

EXAMPLE 34

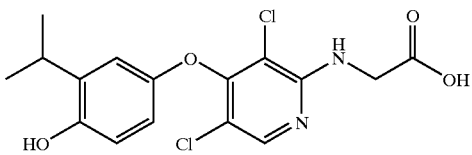

3,5-dichloro-4-(3-isopropyl-4-hydroxyphenoxy)-6-hydroxycarbonylmethylamninopyridine Compound 34a: 3,5-Dichloro-2-ethylthio-4-(3-isopropyl-4-methoxyphenoxy)-6-methoxycarbonylmethylaminopyridine

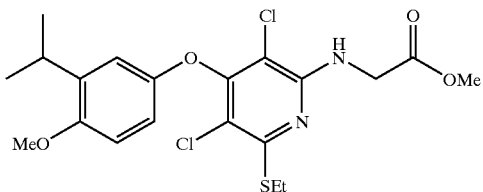

To a solution of 3,5-dichloro-2-fluoro-4-(3-isopropyl-4-methoxyphenoxy)-6-methoxycarbonylmethyl-aminopyridine (200 mg) in DMF was added ethylthiol (0.1 mL, neat) and potassium carbonate powder (100 mg) at ambient temperature. The resulting mixture was stirred for 4 h at ambient temperature and 4 h at 70° C. Cooled reaction mixture was diluted with brine (100 mL) and extracted with ethyl acetate (50 mL×3). Combined organic layers were washed with brine (50 mL×3), dried (Na₂SO₄) and concentrated under reduced pressure. Chromatography with ethyl acetate-hexanes (0–25% gradient elution) afforded compound 34a (130 mg).

¹H NMR (500 MHz, CDCl₃, δ) 6.90 (d, 1H, J=2.7 Hz), 6.69 (d, 1H, J=8.8 Hz), 6.49 (dd, 1H, J=8.8 Hz, 2.7 Hz), 5.53 (br. t, 1H, J=5 Hz), 4 24 (d, 2H, J=5 Hz), 3.79 (s, 3H), 3.78 (s, 3H), 3.28 (septet, 1H, 7 Hz), 3.11 (q, 2H, J=7 Hz), 1.38 (t, 3H, J=7 Hz), 1.19 (d, 6H, J=7 Hz).

Compound 34b: 3,5-Dichloro-4-(3-isopropyl-4-hydroxyphenoxy)-6-hydroxycarbonylmethylaminopyridine

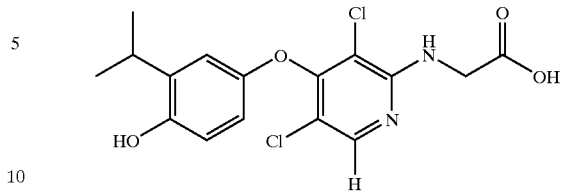

To a suspension of Raney-Nickel (ca. 0.3 g) in ethanol (2 mL) was added a solution of 3,5-dichloro-2-ethylthio-4-(3-isopropyl-4-methoxyphenoxy)-6-methoxy-carbonyl-methylaminopyridine (122 mg) in ethanol (3 mL) at ambient temperature. The resulting mixture was stirred at reflux for 3 hours. Cooled reaction mixture was filtered through celite. Filtrate was extracted with ethyl acetate (50 mL×3) from brine, dried (Na₂SO₄) and concentrated to dryness under reduced pressure. The residue was dissolved in CH₂Cl₂ (3 mL), treated with a solution of BBr₃ in CH₂Cl₂ (1 mL, 1.0 M), stirred at ambient temperature for 30 min. The reaction mixture was diluted with brine (50 mL), extracted with CH₂Cl₂ (50 mL×3), dried (Na₂SO₄) and concentrated under reduced pressure. Purification by HPLC afforded the title compound (24 mg).

¹H NMR (500 MHz, CD₃OD, δ) 8.02 (s, 1H), 6.71 (d, 1H, J=2.7 Hz), 6.64 (d, 1H, J 8.8 Hz), 6.41 (dd, 1H, J=8.8 Hz, 2.7 Hz), 4 15 (s, 2H), 3.23 (septet, 1H, 7 Hz), 1.17 (d, 6H, J=7 Hz).

EXAMPLE 35

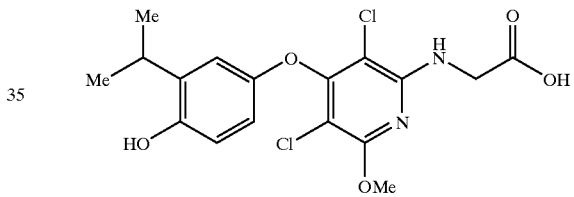

3,5-Dichloro-2-methoxy-4-(3-isopropyl-4-hydroxyphenoxy)-6-hydroxycarbonylmethylaminopyridine To a solution of 3,5-dichloro-2-fluoro-4-(3-isopropyl-4-methoxyphenoxy)-6-methoxycarbonylmethylamino-pyridine (161 mg) in methanol (3.0 mL) was added a solution of sodium methoxide in methanol (0.5 M, 1.0 mL). The resulting mixture was stirred at ambient temperature for 18 hours, followed by stirring at 80° C. for 5 hours. Cooled reaction mixture was then diluted with 1 N HCl (50 mL) and extracted with ethyl acetate (50 mL×2). The combined organic layers were dried (Na₂SO₄) and concentrated. The dried crude product was dissolved in CH₂Cl₂ (3.0 mL) and treated with a solution of BBr₃ in CH₂Cl₂ (1 mL, 1.0 M) at ambient temperature. The resulting mixture was stirred for 1 hour, poured to stirring water (50 mL), extracted with CH₂C₂ (20 mL×3) from water, dried (Na₂SO₄) and concentrated to dryness under reduced pressure. The residue was dissolved in THF:MeOH:H₂)=3:1:1 (3 mL), treated with LiOH in one portion (50 mg) and stirred at ambient temperature for 1 hour. The reaction mixture was diluted with a 1.0 M solution of HCl (50 mL), extracted with ethyl acetate (50 mL×3), dried (Na₂SO₄) and concentrated under reduced pressure. Purification by HPLC afforded the title compound as a white solid (30 mg).

¹H NMR (500 MHz, CD₃OD, δ) 6.70 (d, 1H, J=3.3 Hz), 6.62 (d, 1H, J=8.8 Hz), 6.40 (dd, 1H, J=8,.8 Hz, 3.3 Hz), 4.11 (s, 2H), 3.91 (s, 3H), 3.22 (septet, 1H, 7.2 Hz), 1.16 (d, 6H, J 7.2 Hz).

EXAMPLE 36

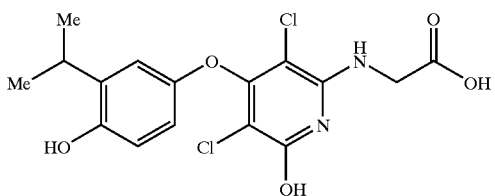

3,5-Dichloro-2-hydroxy-4-(3-isopropyl-4-hydroxyphenoxy)-6-hydroxycarbonylmethylaminopyridine Compound 36a: 2-Benzyloxy-3,5-dichloro-6-fluoro-4-(3-isopropyl-4-methoxyphenoxy)pyridine:

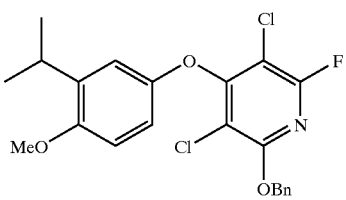

To a solution of 3,5-dichloro-2,6-difluoro-4-(3-isopropyl-4-methoxyphenoxy)pyridine (267 mg) and benzyl alcohol (neat, 100 μL) in THF (2.0 mL) was added a 60% oil dispersion of sodium hydride (50 mg) in one portion. The resulting mixture was stirred at ambient temperature for 30 min. The reaction mixture was diluted with brine, neutralized with 1 N HCl (50 mL), extracted with CH$_2$Cl$_2$ (50 mL×2), dried (Na$_2$SO$_4$) and concentrated. Chromatography with ethyl acetate-hexanes (0–25% gradient elution) afforded compound 36a as a colorless oil (240 mg).

$^1$H NMR (500 MHz, CDCl$_3$, δ) 7.49 (d, 2H, J=7.0 Hz), 7.39 (t, 2H, J=7.0 Hz), 7.35 (t, 1H, J=7.0 Hz), 6.88 (d, 1H, J=2.7 Hz), 6.72 (d, 1H, J=8.8 Hz), 6.53 (dd, 1H, J=8.8 Hz, 2.7 Hz), 5.44 (s, 2H), 3.79 (s, 3H), 3.29 (septet, 1H, 7 Hz), 1.18 (d, 6H, J=7 Hz).

Compound 36b: 2-Benzyloxy-3,5-dichloro-4-(3-isopropyl-4-methoxyphenoxy)-6-methoxycarbonylaminopyridine

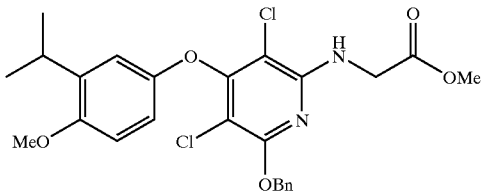

To a solution of 2 benzyloxy-3,5-dichloro-6-fluoro-4-(3-isopropyl-4-methoxyphenoxy)pyridine (98 mg) in DMSO was added glycine methyl ester hydrochloric acid salt (108 mg) and potassium carbonate (200 mg). The mixture was stirred at 100° C. for 2 hours. Cooled reaction mixture was diluted with 1 N HCl (50 mL), extracted with ethyl acetate (50 mL×2). Combined extracts were washed with 1 N HCl (50 mL), dried (Na$_2$SO$_4$) and concentrated. Chromatography with ethyl acetate-hexanes (0–100% gradient elution) afforded compound 36b as a colorless oil (60 mg).

$^1$H NMR (500 MHz, CDCl$_3$, δ) 7.44 (d, 2H, J=7.0 Hz), 7.37 (t, 2H, J=7.0 Hz), 7.32 (t, 1H, J=7.0 Hz), 6.90 (d, 1H, J=2.7 Hz), 6.70 (d, 1H, J=8.8 Hz), 6.53 (dd, 1H, J=8.8 Hz, 2.7 Hz), 5.46 (t, 1H, J=5.0 Hz.), 5.40 (s, 2H), 4.19 (d, 2H, J=5.0 Hz), 3.78 (s, 3H), 3.77 (s, 3H), 3.29 (septet, 1H, 7 Hz), 1.19 (d, 6H, J=7 Hz).

Compound 36c: 3,5-Dichloro-2-hydroxy-6-hydroxycarbonyl-amino-4-(3-isopropyl-4-hydroxyphenoxy)pyridine

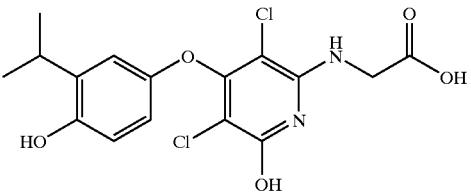

To a solution of 2 benzyloxy-3,5-dichloro-4-(3-isopropyl-4-methoxyphenoxy)-6-methoxycarbonylamino-pyridine (60 mg) in CH$_2$Cl$_2$ (5.0 mL) was added a solution of BBr$_3$ in CH$_2$Cl$_2$ (2 mL, 1.0 M) at ambient temperature. The resulting mixture was stirred for 1.5 hours, poured to stirring water (50 mL), extracted with CH$_2$Cl$_2$ (20 mL×3) from 1 N HCl (50 mL, major solubility problem), dried (Na$_2$SO$_4$) and concentrated to dryness under reduced pressure. The residue was dissolved in THF (3 mL), treated with a solution of LiOH in water (1 mL, 1.0 M) and stirred at ambient temperature for 3 hours. The reaction mixture was diluted with a 1.0 M solution of HCl (50 mL), extracted with ethyl acetate (50 mL×3), dried (Na$_2$SO$_4$) and concentrated under reduced pressure. Purification by HPLC afforded the title compound as a white solid (5 mg).

$^1$H NMR (500 MHz, CD3OD, δ) 6.71 (d, 1H, J=2.7 Hz), 6.62 (d, 1H, J=8.8 Hz), 6.41 (dd, 1H, J=8.8 Hz, 2.7 Hz), 4.13 (s, 2H), 3.23 (septet, 1H, 7 Hz), 1.16 (d, 6H, J=7.2 Hz).

EXAMPLE 37

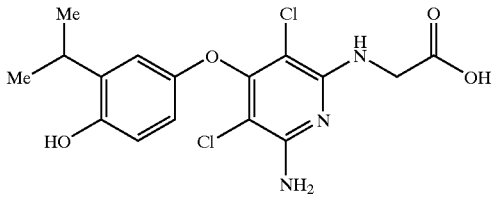

2-Amino-3,5-dichloro-6-hydroxycarbonylmethylamino-4-(3-isopropyl-4-hydroxyphenoxy)pyridine Compound 37a: 2-Amino-6-benzylaminocarbonyl-methylamino-3,5-dichloro-4-(3-isopropyl-4-hydroxyphenoxy)pyridine.

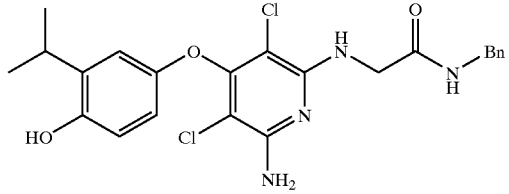

To a solution of 3,5-dichloro-2-fluoro-4-(3-isopropyl-4-methoxyphenoxy)-6-methoxycarbonylmethylamino-pyridine (80 mg) and benzyl amine (neat, 100 μL) in methanol (2.0 mL) was added potassium carbonate (200 mg) in one portion. The resulting mixture was stirred at 80° C. for 20 hours. Cooled reaction mixture was diluted with brine, extracted with ethyl acetate (50 mL×2), dried (Na$_2$SO$_4$), and concentrated. The residue was dissolved in CH$_2$Cl$_2$ (5.0 mL) and treated with a solution of BBr$_3$ in CH$_2$Cl$_2$ (2 mL, 1.0 M) at ambient temperature. The resulting mixture was stirred for 2 hours, poured to stirring 1 N HCl (50 mL), extracted with ethyl acetate (20 mL×3) from 1 N HCl (50 mL, major solubility problem, dried (Na₂SO₄) and concentrated to dryness under reduced pressure. Purification by HPLC afforded compound 37a (35 mg).

¹H NMR (500 MHz, CD₃OD, δ) 7.25 (m, 5H), 6.70 (d, 1H, J=2.7 Hz), 6.59 (d, 1H, J=8.8 Hz), 6.38 (dd, 1H, J=8.8 Hz, 2.7 Hz), 4.41 (s, 2H), 4.03 (s, 2H), 3.20 (septet, 1H, 7 Hz), 1.14 (d, 6H, J=7.2 Hz).

Compound 37b: 2-Amino-3,5-dichloro-4-(3-isopropyl-4-hydroxy-phenoxy)-6-hydroxycarbonylaminopyridine

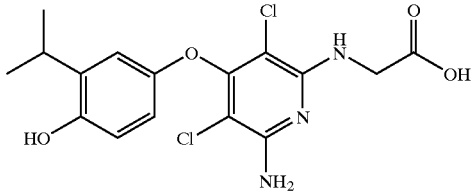

To a solution of 2-amino-6-benzylaminocarbonyl-methylamino-3,5-dichloro-4-(3-isopropyl-4-hydroxy-phenoxy)pyridine (35 mg) in methanol (5 mL) was added concentrated sulfuric acid (0.3 mL). The resulting mixture was stirred at reflux for 18 hours. Cooled reaction mixture was diluted with water (50 mL) and extracted with ethyl acetate (50 mL×2). Combined extracts were dried (Na₂SO₄) and concentrated under reduced pressure to afford the methyl ester as a light yellow oil (25 mg). This intermediate was dissolved in methanol (3.0 mL), treated with a solution of LiOH in water (1.0 M, 1.0 mL), stirred at ambient temperature for 1 h, diluted with 1N HCl (50 mL), extracted with EtOAc (50 mL×2), dried (Na₂SO₄) and concentrated. Preparative, HPLC purification afforded the title compound as a white solid (23 mg).

¹H NMR (500 MHz CD₃OD, δ) 6.71 (d, 1H, J=2.7 Hz), 6.62 (d, 1H, J=8.8 Hz), 6.41 (dd, 1H, J=8.8 Hz, 2.7 Hz), 4.13 (s, 2H), 3.23 (septet, 1H, 7 Hz), 1.15 (d, 6H, J=7.2 Hz).

EXAMPLE 38

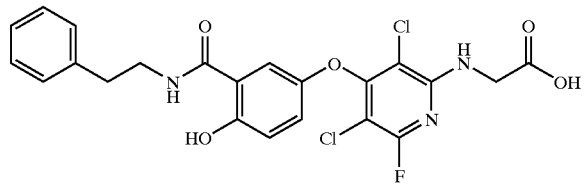

3,5-Dichloro-2-fluoro-4-[3-(phenethylaminocarbonyl)-4-hydroxyphenoxy]-6-hydroxycarbonylmethylaminopyridine Compound 38a: 3,5-dichloro-2,6-difluoro-4-[3-formyl-4-methoxyphenoxy]pyridine

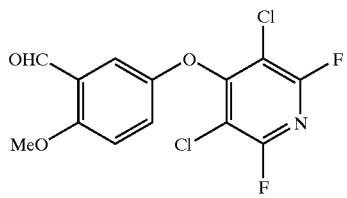

3,5-dichloro-2,6-difluoro-4-(4-methoxyphenoxy)-pyridine (0.31 g, 1 mmol) was dissolved in 7 mL of methylenechloride and cooled to −58° C. under argon. Dichloromethyl methyl ether (0.18 mL, 2 mmol) was added, followed by dropwise addition of an 1.0 M tin chloride solution in methylenechloride (6 mL). The reaction mixture was stirred for 5 hrs at 0° C. then quenched by the addition of 3 mL of 1N HCl. After stirring for 30 minutes, product was extracted 2× with 50 mL portions of methylene chloride. The product was purified by silica gel chromatography using 10% ethyl acetate in hexanes. The appropriate fractions were combined and concentrated to yield 0.26 g (77%) of compound 38a. M.P. 111–112° C.

¹H NMR (CDCl₃) δ 7.25–7.20 (2H, m), 7.02 (1H, d, J 8.78 Hz), 3.94 (3H, s), 10.41 (1H, s).

Compound 38b: 3,5-Dichloro-2,6-difluoro-4-[3-(hydroxycarbonyl)-4methoxyphenoxy]pyridine

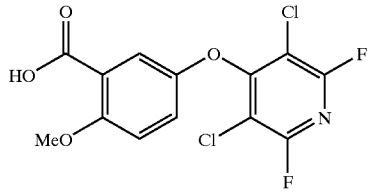

Sulfamic acid (0.74 mL, of 1M solution) was added to a 1 mL THF solution of compound 38a (0.1308 g, 0.392 mmol). This was cooled to 5° C. and sodium chlorite (71 mg, 57.6 mg) in 0.4 mL of water was added dropwise. After addition, the reaction was stirred at room temperature for 1 hr, diluted of with 100 mL of CHCl₂ and 4 mL of water. The organic layer was separated, washed with water, brine, dried (Na₂SO₄), and concentrated in vacuo to yield 0.133 g of compound 38b as a white solid. M.P. 141–149° C.

¹H NMR (CDCl₃) 7.57 (1H, d J 3.30 Hz), 7.25 (1H, dd J 9.35, 3.30 Hz), 7.09 (1H, J 8.80 Hz), 4.09 (3H, s).

Compound 38c: 3,5-Dichloro-2,6-difluoro-4-[3-(phenethylaminocarbonyl)-4-methoxyphenoxy]pyridine

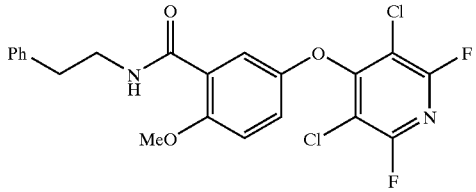

Compound 38b (50 mg, 0.143 mmol), phenethylamine (23.2 mg, 0.185 mmol), hydroxybenzotriazole (21.6 mg, 0.16 mmol) and 1-(3-dimethylaminopropyl)-3-ethylcarbodiimide. HCl were stirred in 2 mL of methylene chloride and 0.2 mL of DMF for 1 hr. The reaction mixture was diluted with 20 mL of methylenechloride and the organic solution was washed with water (2×), brine, dried (Na₂SO₄), filtered and concentrated to yield 62.5 mg (96%) of compound 38c as a foam.

¹H NMR(CDCl₃) δ 7.90 (1H, br s), 7.58 (1H, d, J 4.30 Hz), 7.28–7.25 (2H. m), 7.19–7.17 (3H, m), 7.01 (1H, dd, J 3.30, 9.35 Hz), 6.85 (1H, d 8.80 Hz), 3.68–3.65 (5H, m), 2.83 (2H, t, 7.15 Hz).

Compound 38d: 3,5-Dichloro-2-fluoro-4-[3-(phenethylamino-carbonyl)-4-methoxyphenoxy]-6-methoxycarbonylmethylamino pyridine

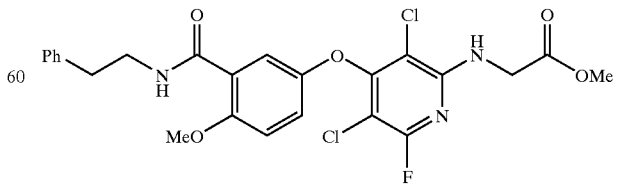

3,5-Dichloro-2,6-difluoro-4-[3-(phenethylaminocarbonyl)-4-methoxyphenoxy]pyridine (64.7 mg), glycine methyl ester HCl (35.2 mg) and potassium carbonate (58 mg) were stirred at room temperature for 2 hrs then at 50° C. for 30 minutes. The reaction was diluted with 50 mL of ethylacetate, washed with water, brine, dried with Na$_2$SO$_4$, filtered and concentrated to yield 62.5 mg of compound 38d. Compound 38e: 3,5-dichloro-2-fluoro-4-[3-(phenethylamino-carbonyl)-4-hydroxyphenoxy]-6-hydroxycarbonyl methylamino pyridine

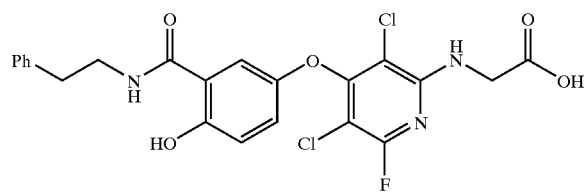

Compound 38d (62.5 mg) was dissolved in 1 mL of CH$_2$Cl$_2$ under argon and cooled to −50° C. Boron tribromide (0.1 mL) was added and the reaction mixture was stirred at ambient temperature for 4 hrs. The reaction mixture was diluted with 10 mL of methylene chloride, then quenched by the addition of 2 g of cracked ice. MeOH was added and the reaction mixture was concentrated in vacuo. The crude reaction mixture was purified by preparative HPLC. The appropriate fractions were concentrated in vacuo to yield 22 mg the title compound as a white solid.

$^1$H NMR(CD$_3$OD) δ 7.27–7.21 (6H, m)), 7.05 (1H, dd, J3.30, 9.35 Hz), 3.56 (2H, t, J 7.15 Hz), 2.87 (2H, J7.70 Hz) [M+H]$^+$ 494.

EXAMPLE 39

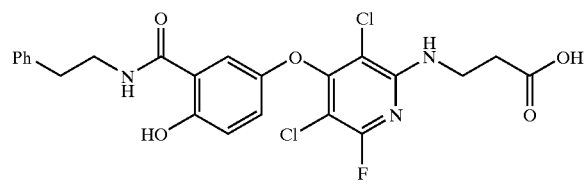

3,5-Dichloro-2-fluoro-4-[3-(phenethylamino-carbonyl)-4-hydroxyphenoxy]-6-hydroxycarbonylethylarino Pyridine The title compound was prepared in the same manner as in Example 38. However, during the preparation of Compound 38d, β-alanine methyl ester HCl was substituted for glycine methyl ester HCl.

$^1$H NMR(CD$_3$OD) δ 7.27–7.18 (6H, m), 7.02 (1H, dd, J 2.63, 8.78 Hz), 2.87 (2H, t, J 7.03 Hz), 2.64 (2H, t, J 6.59 Hz). [M+H]$^+$ 509.

EXAMPLE 40

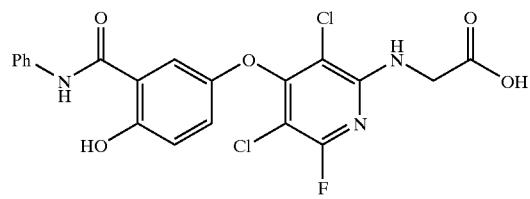

3,5-Dichloro-2-fluoro-4-[3-(phenylamino-carbonyl)-4-hydroxyphenoxy]-6-hydroxycarbonylmethylamino Pyridine The title compound was prepared in the same manner as described in Example 38. However, during the preparation of Compound 38c, aniline was substituted for phenethylamine.

$^1$H NMR(CD$_3$OD) δ 7.61 (2H, d, J 8.35 Hz), 7.53 (1H, d, J 3.07 Hz), 7.35 (2H, t, J 7.47), 7.15 (1H, t, 7.25), 7.09–7.06 (1H, m), 7.00–6.96 (1H, m). [M–H]$^-$ 464.

EXAMPLE 41

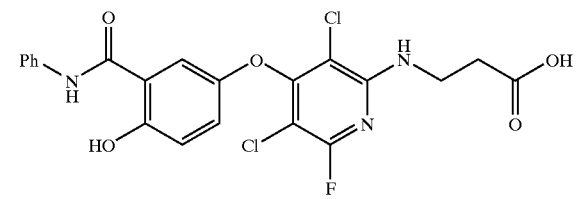

3,5-Dichloro-2-fluoro-4-[3-(phenylamino-carbonyl)-4-hydroxyphenoxy]-6-hydroxycarbonylethyladino Pyridine The title compound was prepared in the same manner as described in Example 38. However, during the preparation of Compound 38c and 38d, phenethylamine and glycine methyl ester were replaced by aniline and β-alanine methyl ester HCl respectively.

$^1$H NMR(CD$_3$OD) δ 7.61 (2H, d, J 8.25 Hz), 7.52 (1H, d, J 2.76 Hz), 7.35 (2H, t, 8.24 Hz), 7.15 (1H, 7.22 Hz), 7.06 (1H, dd, J 3.29, 9.35 Hz), 6.96 (1H, d, J 8.80 Hz) [M+H]$^+$ 480.

EXAMPLE 42

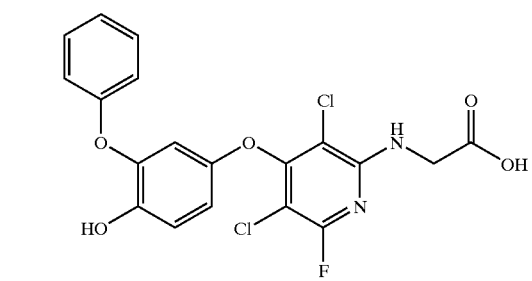

3,5-Dichloro-2-fluoro-4-[3-(phenox)-4-hydroxyphenoxy]-6-hydroxycarbonylmethylaminopyridine Compound 42a: 3,5-Dichloro-2.6-difluoro-4-(3-hydroxy-4-methoxyphenoxy)pyridine A solution of 3,5-Dichloro-2,6-difluoro-4-(3-formyl-4-methoxyphenoxy)pyridine (0.67 g, 2 mmol) and 70% MCPBA (0.64 g, 2.6 mmol) in 8 ml of chloroform was stirred at room temperature overnight. The reaction mixture was diluted with 200 ml of ethyl acetate and washed with 5% aqueous sodiumhydrosulfite (4x), brine, dried (Na$_2$SO$_4$), filtered and concentrated. The crude formate was dissolved in 20 ml of ethanol and 20 ml of 4N HCl in dioxane and stirred at room temperature for 2 hrs. The crude reaction mixture was concentrated, dissolved in methylene chloride (200 ml) and washed with saturated aqueous NaHCO$_3$ (3x), brine, dried (Na$_2$SO$_4$) and concentrated to provide compound 42a in 90% yield.

$^d$H(CDCl$_3$) 6.77 (1H, d J 8.80 Hz), 6.56 (1H, d J 2.75), 6.35 (1H, dd J 3.30 7.25), 3.88 (3H, s 3.88).

Compound 42b: 3,5-Dichloro-2,6-difluoro-4-(3-phenoxy-4-methoxyphenoxy)pyridine 3,5-Dichloro-2,6-difluoro-4-(3-hydroxy-4-methoxyphenoxy) pyridine (540mg, 1.7 mmol), phenylboronic acid (513 mg, 4.2 mmol), copper acetate (310 mg, 1.7 mmol), pyridine (0.65 ml), triethyl amine (0.98 ml) and dried powdered molecular sieves (2 g) were stirred as a slurry in 30 ml of methylene chloride overnight. The reaction mixture was filtered and the filtrate was concentrated to about 4 ml. Product was purified by silica gel chromotography using 7% ethyl acetate in hexanes. The appropriate fractions were combined and concentrated to give 440 mg (64%) of compound 42b. M.P. 90–94C.

$^d$H (CDCl$_3$) 7.33 (2H, app t 8.2 Hz), 7.10 (1H, t 7.4 Hz), 6.97 (2H, d 7.7 Hz), 6.92 (1H, d 8.80), 6.64 (1H, d 2.75Hx), 6.57 (1H, dd 3.30 9.08 Hz), 3.83 (3H s).

Compound 42c: 3,5-Dichloro-2-fluoro-4-(3-phenoxy-4-methoxyphenoxy)-6-methoxycarbonylmethylamino pyridine Compound 42c was prepared in the same manner as described for compound 38d, except that 3,5-dichloro-2,6-difluoro-4-(3-phenoxy-4-methoxyphenoxy)pyridine was substituted for 3,5-dichloro-2,6-difluoro-4-[3-(phenethylaminocarbonyl)-4-methoxyphenoxy pyridine.

Compound 42c was obtained in 85% yield and was carried to the next step without further purification.

Compound 42d: 3,5-Dichloro-2-fluoro-4-(3-phenoxy-4-hydroxy-phenoxy)-6-hydroxycarbonylmethylaminopyridine Compound 42d was prepared in the same manner as described for compound 38e.

$^d$H (CD$_3$OD) 7.31 (2H, app t 8.25 Hz), 7.05 (1H, t 7.70 Hz), 6.93 (2H, app d 7.70 Hz), 6.89 (1H, d 6.87 Hz), 6.55 (1H, dd 2.75 8.80 Hz), 6.48 (1H, d 2.75 Hz), 4.09 (2H, s).

EXAMPLE 43

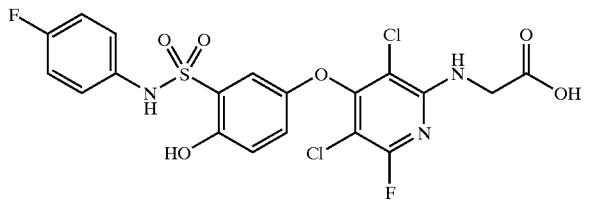

3,5-Dichloro-2-fluoro-4-[3-(parafluorophenantinosulfonyl)-4-hydroxyphenoxy]-6-hydroxycarbonylmethylaminopyridine.

Compound 43a: 3,5-Dichloro-2,6-difluoro-4[3-(hydroxysulfonyl)-4-methoxyphenoxy]pyridine 3,5-Dichloro-2,6-difluoro-4-(4-methoxyphenoxy)pyridine (1.5 g, 4.9 mmol) and chlorosulfonic acid (0.39 ml, 5.8 mmol) were stirred in 5 ml of methylene chloride overnight. The resulting solid-was filtered and washed with cold CH$_2$Cl$_2$. Compound 43a was obtained as solid in 70% yield.

$^d$H (DMSO-d6) 7.36 (1H, d 3.51 Hz), 7.01–6.95 (2H, m), 3.75 (3H, s)

Compound 43b: 3,5-Dichloro-2,6-difluoro-4[3-(p-fluorophenyl-aminosulfonyl)-4-methoxyphenoxy]pyridine Oxalyl chloride (2M in CH$_2$Cl$_2$, 0.2 ml) was added to compound 43a (74.4 mg, 0.2 mmol, in 3 ml of CH$_2$Cl$_2$ followed by the addition of catalytic DMF. The reaction was stirred at ambient temperature for 2 hrs. N-Methylmorpholine (0.088 ml, 0.8 mmol) was then added followed by the addition of 4-fluoroaniline (0.076 ml, 0.8 mmol). The reaction mixture was stirred overnight, diluted with methylene chloride, and washed with saturated aqueous NaHCO$_3$. The organic layer was dried with Na$_2$SO$_4$, filtered and concentrated. Compound 43b was purified by reverse phase preparative HPLC (42% yield).

Compound 43c: 3,5-Dichloro-2-fluoro-4-[3-(p-fluorophenyl-aminosulfonyl)-4-methoxyphenoxy]-6-methoxycarbonylmethyl-aminopyridine 3,5-Dichloro-2,6-difluoro-4[3-(p-fluorophenylaminosulfonyl)-4-methoxyphenoxy]pyridine (27.5 mg), glycine methylester HCl (14.5 mg) and pottasium carbonate (24 mg) were stirred at room temperature overnight. The reaction was diluted with 25 ml of methylene chloride, washed with water, brine, dried with NaSO$_4$, filtered and concentrated to yield 26.9 mg (85%) of compound 43c.

Compound 43d: 3,5-Dichloro-2fluoro-4[3-(p-fluorophenyl-aminosulfonyl)4-hydroxyphenoxy]-6-methoxycarbonyl-methylamino-pyridine 3,5-Dichloro-2fluoro-4-[3-(p-fluorophenylamino-sulfonyl)-4-methoxyphenoxy]pyridine (26.9 mg) was dissolved in 1 ml of methylene chloride and cooled to about –50° C. under argon. Boron tribromide (0.05 ml) was added and the reaction was stirred at 0° C. for 2 hrs. The reaction was diluted with 10 ml of CH$_2$Cl$_2$, then quenched by the addition of about 1 g of cracked ice. MeOH (5 ml) was added and the reaction was concentrated in vacuo. The concentration from methanol was repeated 2× more.

Compound 43e: 3,5-Dichloro-2-fluoro-4-[3-(p-fluorophenyl-aminosulfonyl)-4-hydroxyphenoxy]-6-hydroxycarbonylamino-methylpyridine 3,5-Dichloro-2-fluoro-4[3-(p-fluorophenyl-aminosulfonyl)-4-hydroxyphenoxy]6-methoxycarbonyl methyl-aminopyridine was stirred for 2 hours at room temperature in 2 ml of THF and 0.5 ml of 1N LiOH, The reaction was acidified to pH 2 with dilute aqueous TFA. The reaction was concentrated to remove THF then purified by reverse phase preparative HPLC. The appropriate fractions were combined and concentrated to yield 18.8 mg (73% from compound 43c) of compound 43e for 2 steps.

$^d$H (CD$_3$OD) 7.90–6.90 (7H, m), 4.12 (2H, s) [M–H]$^-$ 518.

EXAMPLE 44

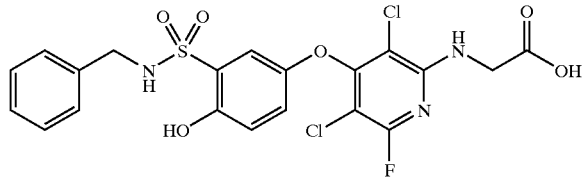

3,5-Dichloro-2-fluoro-4-[3-(benzylaminosulfonyl)-4-hydroxyphenoxy]-6-hydroxycarbonylmethylaminopyridine.

The title compound was prepared according to the methodology described for example 43 except that benzyl amine was used in place of 4-fluoroaniline in the step for compound 43b.

$^d$H (CD$_3$OD) 721–7.17 (6H, m), 7.01 (1H, dd 2.75 Hz, 9.07 Hz), 6.86 (1H, d 9.34 Hz), 4.12 (1H, s), 4.09 (1 Hs) [M–H]$^-$ 514.

EXAMPLE 45

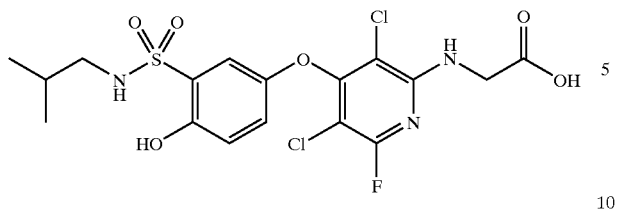

3,5-Dichloro-2-fluoro-4-[3-(isobutylaminosulfonyl)-4-hydroxyphenoxy]-6-hydroxycarbonylmethylaminopyridine.

The title compound was prepared according to the methodology described for example 43 except that isobutyl amine was used in place of 4-fluoroaniline in the step for compound 43b.

$^d$H (CD$_3$OD) 7.18 (1H, d 3.30 Hz), 7.09 (1H, dd 3.30 Hz, 8.80 Hz), 6.97 (1H, d 9.34 Hz), 4.12 (2H, s), 2.66 (2H, d 6.60 Hz), 1.69–1.65 (1H, m), 0.85 (6H, d 6.60 Hz) [M–H]$^-$ 480.

EXAMPLE 46

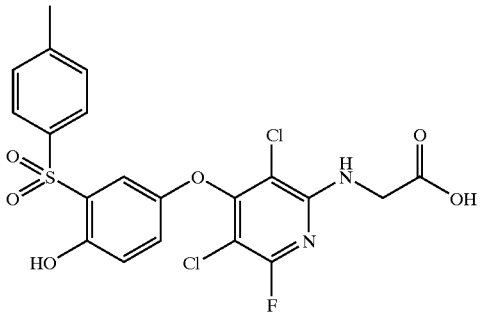

3,5-Dichloro-2-fluoro-4-[3-(p-tolylsulfonyl)-4-hydroxyphenoxy]-6-hydroxycarbonylmethylamninopyridine.

Compound 46a: 3,5-Dichloro-2,6-difluoro-4[3-(p-tolyl-sulfonyl)-4-hydroxyphenoxy]pyridine 3,5-Dichloro-2,6-difluoro-4-(4-methoxyphenoxy)pyridine (0.3 g, 1 mmol), tosylchloride (0.2 g, 1 mmol) and aluminum chloride (0.29 g, 2.1 mmol) were heated at 70° C. for 14 hrs in 15 ml of dichloroethane. The reaction mixture was diluted with 50 ml additional dichloroethane, cooled to 0° C. and quenched by the addition of 1 ml of water. After stirring for 5 minutes, the organic layer was separated, washed with brine, dried (Na$_2$SO$_4$) and concentrated. The crude material was purified by silica chromotography to give a 47% yield of compound 46a.

$^d$H (CDCl) 8.90 (1H, s), 7.72 (2H, d 8.14 Hz), 7.27 (2H, d 8.24 Hz), 7.09 (1H, d 3.29 Hz), 6.98–6.91 (2H, m), 2.36 (3H, s).

Compound 46b: 3,5-Dichloro-2-fluoro-4-[3-(p-tolylsulfonyl)-4-hydroxyphenoxy]-6-methoxycarbonylaminomethylpyridine Compound 46b was prepared according to the method described for compound 43c.

Compound 46c: 3.5 Dichloro-2-fluoro-4-[3-(p-tolylsulfonyl)-4-hydroxyphenoxy]-6-hydroxycarbonylaminomethylpyridine Compound 46c was prepared according to the methodology described for compound 43e.

$^d$H (CD$_3$OD) 7.81 (2H, d 7.91 Hz), 7.41 (1H, d 3.08 Hz), 7.35 (2H, d 7.91 Hz), 7.07 (1H, dd 3.08, 8.29) 4.12 (21, s), 2.41 (3H, s).

EXAMPLE 47

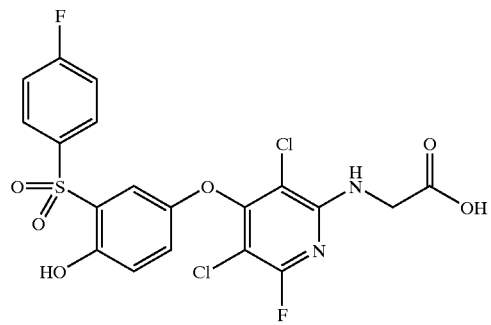

3,5-Dichloro-2-fluoro-4-[3-(p-fluorobenzenesulfonyl)-4-hydroxyphenoxy]-6-hydroxycarbonylmethylaminopyridine.

Compound 47a: 2-(4-Fluorobenzenesulfonyl)-benzene-1,4-diol

To a solution (50 ml THF) of 4-Fluorobenzenesulfonyl chloride (2 g) was added sodiumborohydride (1.9 g) and the reaction was stirred for 1 hour. The reaction was quenched with 5 ml of water and after stirring for 1 hour was concentrated. Ten ml of 6N HCl was added dropwise and 4-fluorobenzenesulfinic acid was extracted with ethyl acetate. The ethyl acetate solution was dried with Na$_2$SO$_4$, filtered and concentrated. The resulting residue was dissolved in 5 ml of water and was added dropwise to a methylene chloride solution of 1,4-benzoquinone. The reaction mixture was stirred over night. Compound 47a was filtered and dried to yeild 1.8 g (72%).

Compound 47b: 3,5 Dichloro-2,6-difluoro-4-[3-(p-fluoro-sulfonyl)-4-hydroxyphenoxy]pyridine 2,4,6-trifluoro-3,5-dichloropyridine (20.1 mg), 2-(4-fluorobenzenesulfonyl)-benzene-1,4-diol (26.8 mg) and tri-ethylamine (5 µl) were stirred in 1 ml of dimethylformarmide overnight. The reaction mixture was concentrated and the crude product purified on a preparative silica gel plate to yield 14 mg of compound 47b.

Compound 47c: 3,5 Dichloro-2,6-difluoro-4-[3-(p-fluoro-sulfonyl)-4-hydroxyphenoxy]-6-methoxycarbonylaminomethyl pyridine Compound 47c was prepared according to the procedure described for compound 43c.

Compound 47d: 3,5-Dichloro-2-fluoro-4-[3-(p-fluorobenzene-sulfonyl)-4-hydroxyphenoxy]-6-hydroxycarbonylaminomethyl pyridine Compound 47d was prepared according to the procedure described for compound 43e.

$^d$H (CD$_3$OD) 8.04–8.00 (2H, m), 7.47 (1H, d 3.30 Hz), 7.32–7.27 (2H, m), 7.09 (1H, dd 3.30 Hz, 9.07 Hz), 6.86 (1H, d 8.80 Hz), 4.13 (2H, s) (M–H)$^-$ 503.

EXAMPLE 48

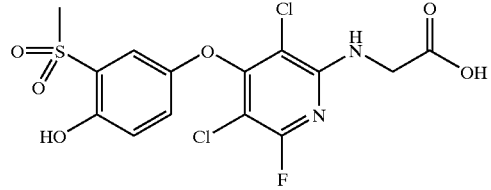

3,5-Dichloro-2-fluoro-4-(3-methanesulfonyl-4-hydroxy-phenoxy)-6-hydroxycarbonylmethylaminopyridine The title compound was prepared according to the procedures described for example 47 except that 2-methylsulfonyl-benzene-1,4-diol was prepared from Na methanesulfinate and 1,4-benzoquinone.

$^d$H (CD$_3$OD) 7.30 (1H, d 3.30 Hz), 7.13 (1H, dd 3.30 Hz, 8.80 Hz), 7.00 (1H, d 9.35 Hz), 4.09 (2H, s), 3.25 (3H, s).

EXAMPLE 49

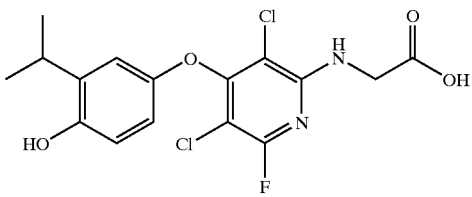

3,5-Dichloro-2-fluoro-4-(3-isopropyl-4-hydroxyphenylamino)-6-hydroxycarbonylmethylaminopyridine
Compound 49a: 3-Isopropyl-4-methoxyaniline

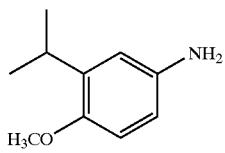

To a solution of 2-isopropylanisole (0.4 g, 2.66 mmol) in $CH_2Cl_2$ (13 mL) was added bis-(2,2,2-trichloroethyl)azodicarboxylate (2.3 g, 6.04 mmol) and zinc chloride (3 mL, 1.0 M solution in $Et_2O$, 3.0 mmol). The mixture was left to stir overnight (ca. 18 h) at ambient room temperature under IS $N_2$. A 25% aqueous ammonium acetate solution (15 mL) was added to quench the reaction. The product was extracted with EtOAc (50 mL). The EtOAc extract was washed with brine (50 mL), dried ($Na_2SO_4$), filtered and concentrated in vacuo. The thick yellow oil crude product was purified by chromatography using the ISCO Combiflash SQ16x system (0 to 50% EtOAc in hexane, 15 min gradient, 35 g Redisep silica gel column) to afford 1.75 g of material which was a mixture of two products. The mixture was dissolved in glacial acetic acid (10 mL). Zinc dust (1 g) was added and the reaction mixture was left to stir overnight (ca. 15 h) under $N_2$ at ambient room temperature. The reaction was quenched by adding 3 N HCl to dissolve the remaining zinc dust. Water (50 mL) and 50% aqueous NaOH was added to make the mixture basic (ca. pH 10). The product was extracted with EtOAc (100 mL). The EtOAc extract was washed with brine (50 mL), dried ($Na_2SO_4$), filtered and concentrated in vacuo. The crude product was purified by chromatography using the ISCO Combiflash SQ16x system (0 to 50% EtOAc in hexane, 15 min gradient, 35 g Redisep silica gel column) to afford 0.343 g (78%, 2 steps) of compound 49a as a purified orange oil.

$^1$H NMR (500 MHz, $CDCl_3$, δ) 6.68 (d, 1H, J=8.8 Hz), 6.595 (d, 1H, J=2.8 Hz), 6.495 (dd, 1H, J=8.2, 2.7 Hz), 3.75 (s, 3H), 3.29 (broad s, 2H), 3.25 (m, 1H), 1.17 (d, 6H, J=7.2 Hz) MS-ESI $[M+H]^+$=166.2.

Compound 49b: 3,5-dichloro-2,6-difluoro-4-(3-isopropyl-4-methoxyphenylamino)pyridine

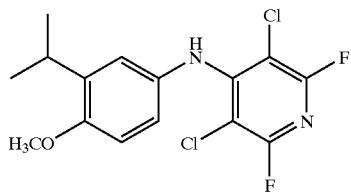

To a stirring slurry of 4-amino-2-isopropylanisole (0.150 g, 0.908 mmol) and $K_2CO_3$ (0.150 g, 1.085 mmol) in DMF (3 mL) was added a solution of 3,5 dichloro-2,4,6-trifluoropyridine (0.185 g, 0.916 mmol) in DMF (1.5 mL). The mixture was stirred at ambient room temperature for 2 h. The mixture was partitioned between EtOAc (50 mL) and $H_2O$ (25 mL). The EtOAc extract was washed with brine (25 mL), dried ($Na_2SO_4$), filtered and concentrated in vacuo. The crude product was purified by chromatography using the ISCO Combiflash SQ16x system (0 to 15% EtOAc in hexane, 15 min gradient, 35 g Redisep silica gel column) to afford 0.279 g (88%) of compound 49b as a purified white solid.

$^1$H NMR (500 MHz, $CDCl_3$, δ) 6.92 (d, 1H, J 2.2 Hz), 6.875 (dd, 1H, J=8.2, 2.7 Hz), 6.80 (broad s, 1H), 6.78 (d, 1H, J=8.8 Hz), 3.84 (s, 3H), 3.31 (m, 1H), 1.175 (d, 6H, J=7.1 Hz); MS-ESI $[M-H]^-$=345.1, 347.1, 348.1 (100:64:10).

Compound 49c: 3,5-dichloro-2-fluoro-4-(3-isopropyl-4-methoxyphenylamino)-6-methoxycarbonylmethylaminopyridine

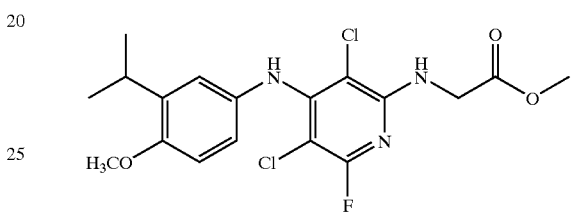

To a solution of compound 49b (0.150 g, 0.432 mmol) and glycine methyl ester hydrochloride (0.160 g, 1.274 mmol) in DMF (4 mL) was added N,N-diisopropylethylamine (0.35 mL, 0.26 g, 2.012 mmol). The mixture was heated to 70° C. and maintained at this temperature overnight (ca. 15 h) under $N_2$. The mixture was cooled down to room temperature and then taken up in EtOAc (50 mL) and $H_2O$ (25 mL). The EtOAc extract was washed with brine (25 mL), dried ($Na_2SO_4$), filtered and concentrated in vacuo. The crude product was purified by chromatography using the ISCO Combiflash SQ16x system (0 to 50% EtOAc in hexane, 15 min gradient, 35 g Redisep silica gel column) to afford 0.065 g of compound 49c (48036-110B) as a white solid.

$^1$H NMR (500 MHz, $CDCl_3$, δ) 6.865 (d, 1H, J=2.2 Hz), 6.785 (dd, 1H, J=8.8, 2.2 Hz), 1H), 6.75 (d, 1H, J=8.8 Hz), 6.36 (broad s, 1H), 5.49 (t, 1H, J=5 Hz), 4.19 (d, 2H, J=5.5 Hz), 3.82 (s, 3H), 3.78 (s, 3H), 3.29 (m, 1H), 1.175 (d, 6H, J=7.2 Hz); MS-ESI $[M-H]^-$=414.2, 416.2, 418.2 (100:64:10).

Compound 49d: 3,5-dichloro-2-fluoro-4-(3-isopropyl-4-hydroxyphenylamino)-6-hydroxycarbonylmethylaminopyridine

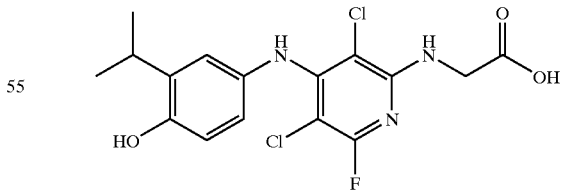

To a solution of compound 49c (55 mg, 0.132 mmol) in $CH_2Cl_2$ (3 mL) cooled with an ice-$H_2O$ bath was added boron tribromide (1.3 mL, 1.0 M solution in $CH_2Cl_2$, 1.3 mmol). The temperature was allowed to warm up to room temperature. After 2 h, the mixture was poured into a flask containing ice-water (25 ml) and stirred for 10 min. The product was extracted with EtOAc (25 mL). The EtOAc extract was washed with brine (25 mL), dried (Na₂SO₄), filtered and concentrated in vacuo. The crude product was purified by prep HPLC to afford 37.6 mg (73%) of title compound as an orange solid.

¹H NMR (500 MHz, CD₃OD, δ) 6.80 (d, 1H, J=2.2 Hz), 6.64 (s, 1H), 6.635 (d, 1H, J=2.2 Hz), 2.06 (s, 2H), 3.24 (m, 1H), 1.17 (d, 6H, J=6.6 Hz); MS–ESI [M–H]⁻=386.1, 388.1, 390.1 (100:64:10).

EXAMPLE 50

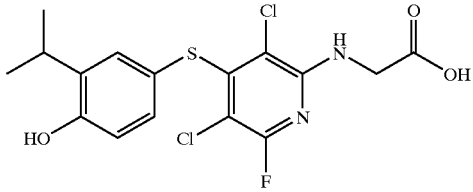

3,5-Dichloro-2-fluoro-4-(3-isopropyl-4-hydroxyphenylthio)-6-hydroxycarbonylmethylaminopyridine Compound 50a: 4-chlorosulfonyl-2-isopropylanisole

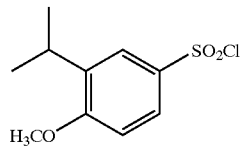

To a solution of 2-isopropylanisole (0.40 g, 2.66 mmol) in CH₂Cl₂ (9 mL) cooled with an ice water bath was added slowly chlorosulfonic acid (4 mL). After 1.5 h of cooling, the mixture was poured into a flask containing ice (25 g). The product was extracted with CH₂Cl₂ (50 mL). The organic extract was washed with brine (25 mL), dried (Na₂SO₄), filtered and concentrated in vacuo to afford 0.62 g of grayish oil as crude product. The crude product was purified by chromatography using the ISCO Combiflash SQ16x system (0 to 20% EtOAc in hexane, 20 min gradient, 35 g Redisep silica gel column) to give 0.56 g (84%) of compound 50a as a clear oil.

¹H NMR (500 MHz, CDCl₃, δ) 7.87 (dd, 1H, J=8.8 Hz, 2.2 Hz), 7.82 (d, 1H, J=2.8 Hz), 6.96 (d, 1H, J=8.8 Hz), 3.94 (s, 3H), 3.33 (m, 1H), 1.235 (d, 6H, J=6.6 Hz); MS–DCI⁺ [M–Cl]⁺=212.8 (100%).

Compound 50b: 4-thio-2-isopropylanisole

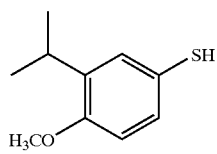

A mixture of 4-chlorosulfonyl-2-isopropylanisole (0.30 g, 1.21 mmol), zinc dust (0.5 g) in 25% H₂SO₄ (15 ml) was heated to 110° C. and maintained at this temperature for 4 h. The mixture was cooled down to RT and the product was extracted with EtOAc (50 mL). The EtOAc extract was washed with brine (25 mL), dried (Na₂SO₄), filtered and concentrated and dried in vacuo to give 0.18 g (82%) of compound 50b.

¹H NMR (500 MHz, CDCl₃, δ) 7.165 (d, 1H, J=2.2 Hz), 7.135 (dd, 1H, J=8.2 Hz, 2.2 Hz), 6.72 (d, 1H, J=8.8 Hz), 3.79 (s, 3H), 3.25 (m, 1H), 1.17 5 (d, 6H, J=6.6 Hz).

Compound 50c: 3,5-dichloro-2,6-difluoro-4-(3-isopropyl-4-methoxyphenylthio) pyridine

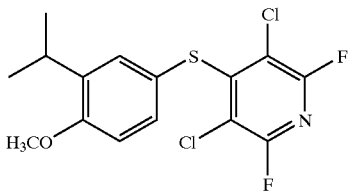

To the crude 4-thio-2-isopropylanisole (0.14 g, 0.77 mmol) in DMF (3 mL) was added potassium carbonate (0.17 g, 1.23 mmol) and a solution of 3,5-dichloro-2,4,6-trifluoropyridine (0.14 g, 0.69 mmol) in DMF (1 mL). After 2 h, the mixture was partitioned between EtOAc (50 mL) and H2O (25 mL). The EtOAc extract was washed with brine (25 mL), dried (Na₂SO₄), filtered and concentrated in vacuo. The crude product was purified by chromatography (50 g silica gel, 2% EtOAc in hexane) to afford 0.18 g (64%) of compound 50c.

¹H NMR (500 MHz, CDCl₃, δ) 7.29 (d, 1H, J=2.2 Hz), 7.135 (dd, 1H, J=8.5 Hz, 2.2 Hz), 6.76 (d, 1H, J=8.8 Hz), 3.82 (s, 3H), 3.26 (m, 1H), 1.16 (d, 6H, J=6.6 Hz).

Compound 50d: 3,5-dichloro-2-fluoro-4-(3-isopropyl-4-methoxyphenylthio)-6-methoxycarbonylmethylaminopyridine

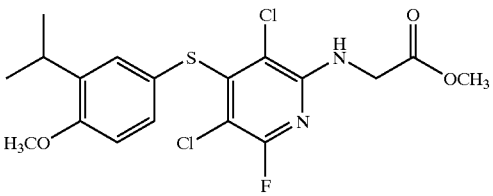

To a solution of compound 50c (0.17 g, 0.47 mmol) and glycine methyl ester hydrochloride (0.12 g, 0.95 mmol) in N,N-dimethylacetamide (5 mL) was added N,N-diisopropylethyl-amine (0.35 mL, 0.26 g, 2.01 mmol⁻). The mixture was heated to 70° C. and maintained at this temperature for 3 h. The mixture was cooled to RT and partitioned between EtOAc (50 ml) and H₂O (25 mL). The EtOAc extract was washed with 1N HCl (25 mL) and brine (25 mL) and then dried (Na₂SO₄), filtered and concentrated in vacuo. The crude product was purified by chromatography (50 g silica gel, 15% EtoAc in hexane) to afford 0.15 g (72%) of compound 50d as a white solid.

¹H NMR (400 MHz, CDCl₃, δ) 7.29 (d, 1H, J=2.6 Hz), 7.15 (dd, 1H, J=8.6 Hz, 2.4 Hz), 6.73 (d, 1H, J=8.4 Hz), 5.71 (t, 1H, J=4.8 Hz), 4.17 (d, 2H, J=5.3 Hz), 3.79 (s, 3H), 3.78 (s, 3H), 3.24 (m, 1H), 1.16 (d, 6H, J=7.1 Hz); MS–ESI⁻ [M–H]⁻=431, 433, 435 (100:64:10).

Compound 50e: 3,5-dichloro-2-fluoro-4-(3-isopropyl-4-hydroxyphenylthio)-6-hydroxycarbonylmethylaminopyridine

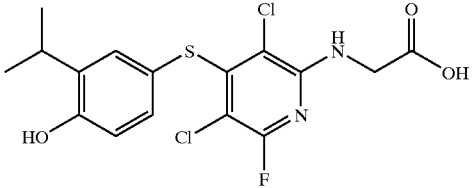

To a solution of 48036–163 (65 mg, 0.15 mmol) in CH₂Cl₂ (3 mL) cooled with an ice water bath was added boron tribromide (1.0 mL, 1.0 M solution in CH₂Cl₂, 1.0 mmol). The temperature was allowed to warm up to room temperature. After 2 h, the mixture was poured into a flask containing ice-water (25 mL) and stirred for 10 min. The product was extracted with EtOAc (50 mL). The EtOAc extract was washed with brine (25 mL), dried (Na$_2$SO$_4$), filtered and concentrated in vacuo. The crude product was purified by prep HPLC to afford 29 mg (48%) of the title compound as a white solid.

$^1$H NMR (400 MHz, CD$_3$OD, δ) 7.20 (d, 1H, J=2.7 Hz), 6.995 (dd, 1H, J=8.4. Hz, 2.7 Hz), 6.68 (d, 1H, J=8.4 Hz), 4.07 (s, 2H), 3.21 (m, 1H), 1.155 (d, 6H, J=7.0 Hz); MS-ESI$^-$[M-H]$^-$=403, 405, 407 (100:64:10).

EXAMPLE 51

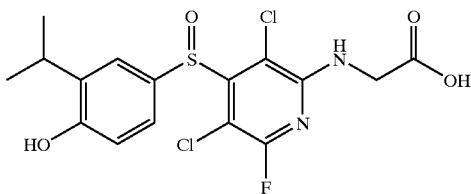

[3,5-Dichloro-6-fluoro-4-(4-hydroxy-3-isopropyl-benzene-sulfinyl)pyridin-2-ylamino]-acetic Acid To a solution of 3,5-dichloro-2-fluoro-4-(3-isopropyl-4-hydroxyphenylthio)-6-hydroxycarbonylmethylaminopyridine (25 mg, 0.06 mmol) in CH$_2$Cl$_2$ (1.5 mL) was added 3-chloroperoxy-benzoic acid (11 mg). The mixture was left to stir overnight (ca. 15 h) at ambient room temperature. The product was extracted with EtOAc (25 mL). The organic extract was washed with brine (25 mL), dried (Na$_2$SO$_4$), filtered and concentrated in vacuo. The isolated crude product was purified by preparative HPLC (from 50% B to 100% B for 10 min, Solvent A=90% H$_2$O–10% MeOH-0.1% TFA Solvent B=10% MeOH-90% H$_2$O–0.1% TFA, at 20 mL/min using column YMC ODS S5 20×100 mm) to afford 16.5 mg (64%) of title compound as a white solid.

$^1$H NMR (400 MHz, CD$_3$OD, δ) 7.70 (d, 1H, J=2.2 Hz), 7.435 (dd, 1H, J=8.8 Hz, 2.2 Hz), 6.89 (d, 1H, J=8.4 Hz), 4.08 (s, 2H), 3.71 (s, 3H), 3.32–3.37 (m, 1H), 1.21,1,20 (2d, 6H, J=7.0 Hz); MS-ESI$^-$[M-H]$^-$=419, 421, 423 (100:64:10).

EXAMPLE 52

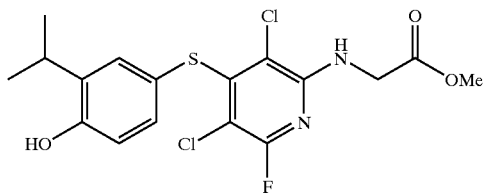

[3,5-Dichloro-6-fluoro-4-(4-hydroxy-3-isopropyl-benzene-sulfanyl)pyridin-2-ylamino]acetic Acid Methyl Ester To a solution of [3,5-dichloro-6-fluoro-4-(3 isopropyl-4-methoxy-phenylsulfanyl)-pyridin-2-ylamino]-acetic acid methyl ester (600 mg, 1.38 mmol) in CH$_2$Cl$_2$ (14 mL) cooled with an ice water bath was added boron tribromide (0.65 mL, 1.72 g, 6.87 mmol). The temperature was allowed to warm up to RT. After 2 h, the mixture was slowly poured into a flask containing EtOAc (100 mL) and saturated aqueous NaHCO$_3$ solution (75 mL). The EtOAc extract was washed with brine (50 mL), dried (Na$_2$SO$_4$), filtered and concentrated in vacuo. The crude product was refluxed in methanolic HCl (30 mL) for 2 h. The temperature was cooled to room temperature and then concentrated in vacuo. The crude product was purified by chromatography using the ISCO Combiflash SQ16X system (35 g Redisep silica gel column, 0 to 50% EtOAc in hexane for 30 min at 30 mL/min) to afford 517.4 mg (89%) of the title compound as a yellowish thick oil.

$^1$H NMR (500 MHz, CDCl$_3$, δ) 7.30 (d, 1H, J=2.2 Hz), 7.045 (dd, 1H, J=8.2 Hz, 2.2 Hz), 6.65 (d, 1H, J=8.8 Hz), 5.71 (t, 1H, J=5.0 Hz), 4.86 (s, 1H), 4.175 (d, 2H, J=5.0 Hz), 3.78 (s, 3H), 3.18–3.11 (m, 1H), 1.21 (d, 6H, J=7.2 Hz); MS-ESI$^-$[M-H]$^-$=417, 419, 421 (100:64:10).

EXAMPLE 53

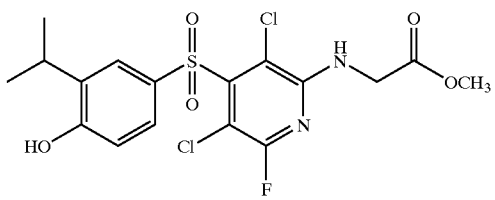

[3,5-Dichloro-6-fluoro-4-(4-hydroxy-3-isopropyl-benzene-sulfonyl)pyridin-2-ylamino]acetic Acid Methyl Ester To a solution of [3,5-dichloro-6-fluoro-4-(4-hydroxy-3-isopropyl-benzen-sulfanyl)pyridin-2-ylamino]acetic acid methyl ester (title compound of example 52) (175 mg, 0.42 mmol) in CH$_2$Cl$_2$ (8 mL) was added 3-chloroperoxybenzoic acid (300 mg). The mixture was left to stir overnight (ca. 15 h) at ambient room temperature. The mixture was poured into a flask containing saturated aqueous NaHCO$_3$ (50 mL). The product was extracted with CH$_2$Cl$_2$ (100 mL). The organic extract was washed with brine (50 mL), dried (Na$_2$SO$_4$), filtered and concentrated in vacuo. The crude product was purified by chromatography using the ISCO Combiflash SQ16X system (35 g Redisep silica gel column, 0 to 75% EtOAc in hexane for 20 min at 30 mL/min) to afford 167.3 mg (89%) of desired product as a white solid which was 92% pure by analytical HPLC. The product isolated was further purified by preparative HPLC (from 50% B to 100% B for 10 min, Solvent A=90% H$_2$O–10% MeOH-0.1% TFA Solvent B=10% MeOH-90% H$_2$O–0.1% TFA, at 20 mL/min using column YMC ODS S5 20×100 mm) to afford 90 mg of the title compound as a white solid.

$^1$H NMR (500 MHz, CD$_3$OD, δ) 7.88 (d, 1H, J=2.8 Hz), 7.73 (dd, 1H, J=8.8 Hz, 2.2 Hz), 6.65 (d, 1H, J=8.8 Hz), 4.11 (s, 2H), 3.71 (s, 3H), 3.33–3.28 (m, 1H), 1.22 (d, 6H, J=7.1 Hz); MS-ESI$^-$[M-H]$^-$=449, 451, 453 (100:64:10).

EXAMPLE 54

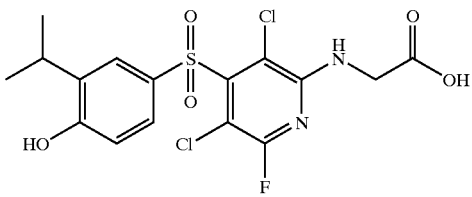

[3,5-Dichloro-6-fluoro-4-(4-hydroxy-3-isopropyl-benzene-sulfonyl)pyridin-2-ylamino]acetic Acid To a solution of the title compound of example 53 (90 mg, 0.20 mmol) in THF (2 mL) was added 1N LiOH aqueous solution (0.6 mL). After an hour, the mixture was acidified with 1N HCl and the product was extracted with EtOAc (50 mL). The organic extract was washed with brine (20 mL), dried ($Na_2SO_4$), filtered and concentrated and dried in vacuo to afford 77.4 mg (89%) of the title compound as a white solid.

$^1$H NMR (500 MHz, $CD_3OD$, δ) 7.88 (d, 1H, J=2.2 Hz), 7.73 (dd, 1H, J=8.8 Hz, 2.2 Hz), 6.91 (d, 1H, J=8.2 Hz), 4.07 (s, 2H), 3.71 (s, 3H), 3.32–3.27 (m, 1H), 1.22 (d, 6H, J=7.1 Hz); MS–ESI$^-$[M–H]$^-$=435, 437, 439 (100:64:10).

EXAMPLE 55

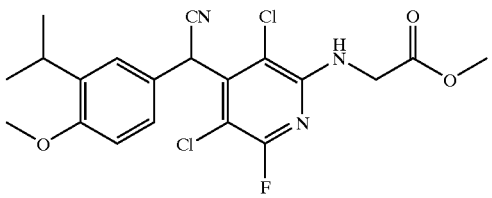

{3,5,dichloro-4-[cyano-(3-isopropyl-4-methoxy-phenyl)-methyl]-6-fluoro-pyridin-2-ylamino}-acetic Acid Methyl Ester Compound 55a: (3-Isopropyl-4-methoxyphenyl)methanol

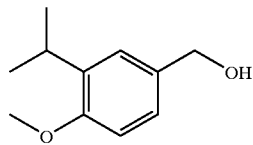

To a solution of 3-isopropyl-4-methoxy-benzaldehyde (1.5 g, 8.42 mmol) in anhydrous THF (17 mL) cooled to -78° C. with a dry ice-acetone bath was added diisobutylaluminum hydride (34 mL, 1.0 M solution in THF, 34 mmol). After 1.5 h of cooling, 1N HCl (30 mL) was slowly added to the mixture. After the addition, the cooling bath was removed and the mixture left to stir at RT (ca. 15 min). The product was extracted with EtOAc (100 mL). The EtOAc extract was washed with brine (50 mL), dried ($Na_2SO_4$), filtered, and concentrated in vacuo to give 1.405 g of colorless oil as crude product. The crude product was purified by chromatography using the ISCO Combiflash SQ16X system (35 g Redisep silica gel column, 0 to 40% EtOAc in hexane for 30 min at 30 mL/min) to afford 1.272 g (84%) of compound 55 as a colorless oil.

$^1$H NMR (500 MHz, $CDCl_3$, δ) 7.21 (d, 1H, J=2.2 Hz), 7.16 (dd, 1H, J=8.3, 2.2 Hz), 6.825 (d, 1H, J.=8.3 Hz), 4.61 (d, 2H, J=6.1 Hz), 3.82 (s, 3H), 3.31 (heptet, 1H, 6.6 Hz), 1.50 (t, 1H, J=5.8 Hz), 1.205 (d, 6H, J=7.1 Hz).

Compound 55b: 4-Bromomethyl-2-isopropyl-1-methoxybenzene

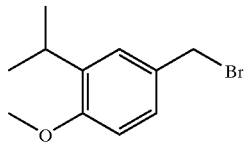

To a solution of (3-isopropyl-4-methoxy-phenyl)-methanol (0.400 g, 2.219 mmol) in $CH_2Cl_2$ (4.5 ml,) was added phosphorus tribromide (2.3 mL, 1.0 M solution in $CH_2Cl_2$, 2.300 mmol). After 2 h, $H_2O$ (25 mL) was added to quench the mixture. The product was extracted with $CH_2Cl_2$ (50 mL). The organic extract was washed succesively with saturated $NaHCO_3$ solution (2×25 mL) and brine (25 mL). The organic extract was dried ($Na_2SO_4$), filtered, concentrated and dried in vacuo to afford 0.5294 mg (98% crude yield) of compound 55b as a colorless oil.

$^1$H NMR (500 MHz, $CDCl_3$, δ) 7.215 (d, 1H, J=2.2 Hz), 7.195 (dd, 1H, J.=8.2, 2.2 Hz), 6.785 (d, 1H, J=8.3 Hz), 4.51 (s, 2H), 3.82 (s, 3H), 3.28 (heptet, 1H, 7.1 Hz), 1.20 (d, 6H, J=6.6 Hz).

Compound 55c: (3-Isopropyl-4-methoxyphenyl)acetonitrile:

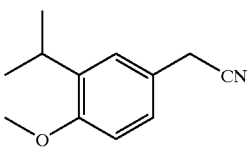

Sodium cyanide (0.500 g, 10.202 mmol) in DMSO (4 mL) was heated to 100° C. After a few minutes of heating, most of the sodium cyanide was dissolved. A solution of the crude 4-bromoethyl-2-isoppropyl-1-methoxy-benzene (0.500 g, 2.065 mmol) in DMSO (1.5 mL) was added to the sodium cyanide solution. After an hour of heating, the mixture was cooled to RT and the product partitioned between EtOAc (100 mL) and $H_2O$ (50 mL). The EtOAc extract was washed with brine, dried ($Na_2SO_4$), filtered and concentrated in vacuo. The crude product was purified by chromatography using the ISCO Combiflash SQ16X system (35 g Redisep silica gel column, 0 to 20% EtOAc in hexane for 20 min at 30 mL/min) to afford 0.326 g (84%) of compound 55c as a colorless oil.

$^1$H NMR (500 MHz, $CDCl_3$, δ) 7.11 (dd, 1H, J=6.5, 2.7 Hz), 7.10 (s, 1H), 6.815 (dd, 1H, J=6.6, 2.8 Hz), 3.82 (s, 3H), 3.67 (s, 2H), 3.29 (heptet, 1H, 6.6 Hz), 1.195 (d, 6H, J=6.6 Hz); MS–DCI: [M–H]$^-$ 188.2.

Compound 55d: (3,5-dichloro-2,6-difluoro-pyridin-4-yl)-(3-isopropyl-4-methoxyphenyl)acetonitrile

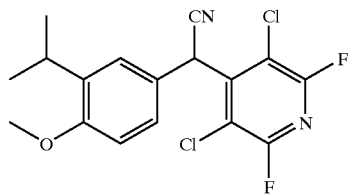

To a stirring slurry of sodium hydride (30 mg, 60% dispersion, 0.75 mmol) in DMF (1 mL) was added a solution of (3-isopropyl-4-methoxy-phenyl)-acetonitrile (70 mg, 0.37 mmol) in DMF (1 mL). The mixture was stirred for ca. 10 min, then a solution of 3,5-dichloro-2,4,6-trifluoropyridine in DMF (1.5 mL) was added. After 2 h, the mixture was quenched with H$_2$O (10 mL) and the product was extracted with EtOAc. (50 mL). The EtOAc extract was washed with brine, dried (Na$_2$SO$_4$), filtered, and concentrated in vacuo. The crude product was purified by preparative HPLC (from 50% B to 100% B for 10 min, Solvent A=90% H$_2$O–10% MeOH-0.1% TFA Solvent B=10% MeOH-90% H$_2$O–0.1% TFA, at 20 mL/min using column YMC ODS S5 20×100 mm) to afford 59.3 mg (43%) of compound 55d as a white solid.

$^1$H NMR (500 MHz, CDCl$_3$, δ) 7.25 (d, 1H, J=2.7 Hz), 7.095 (dd, 1H, J=7.7 2.8 Hz), 6.80 (d, 1H, J=8.8 Hz), 6.11 (s, 1H), 3.81 (s, 3H), 3.27 (heptet, 1H, 7.1 Hz), 1.185, 1.16 (2d, 6H, J=6.6H, 7.2 Hz); MS–ESI: [M–H]$^-$ 369, 371, 373 (100:64:10).

Compound 55e: {3,5, dichloro-4-[cyano-(3-isopropyl-4-methoxy-phenyl)-methyl]-6-fluoropyridin-2-ylamino}acetic acid methyl ester

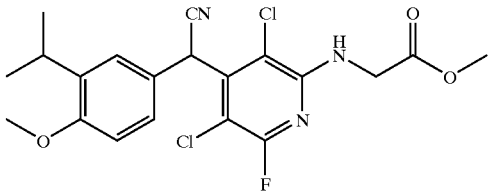

A mixture of (3,5-dichloro-2,6-difluoro-pyridin-4-yl)-(3-isopropyl-4-methoxy-phenyl)-acetonitrile (55 mg, 0.148 mmol), glycine methyl ester hydrochloride (40 mg, 0.19 mmol) and N,N-disopropylethylamine (89 mg, 0.12 mL, 0.689 mmol) in N,N-dimethylacetamide (3 mL) was heated to 70° C. and maintained at this temperature for an hour. The mixture was cooled to room temperature and diluted with EtOAc (75 mL). Subsequently, the mixture was washed successively with 1N HCl (2×50 mL) and brine (50 mL), then dried (Na$_2$SO$_4$), filtered and concentrated in vacuo. The crude product was purified by chromatography using the ISCO Combiflash SQ16X system (35 g Redisep silica gel column, 0 to 60% EtOAc in hexane for 30 min at 30 mL/min) to afford 56.2 mg (86%) of compound 55e as a white solid.

$^1$H NMR (500 MHz, CDCl$_3$, δ) 7.265 (d, 1H, J=2.7 Hz), 7.095 (dd, 1H, J=7.7, 2.7 Hz), 6.78 (d, 1H, J=8.2 Hz), 6.02 (s, 1H), 5.79 (t, 1H, J=5.0 Hz), 4.185 (d, 2H, J=5.5 Hz), 3.80 (s, 3H), 3.79 (s, 3H), 3.27 (heptet, 1H, 6.6 Hz), 1.19, 1.165 (2d, 6H, J=6.6, 6.6 Hz). MS ESI$^-$[M–H]$^-$: 438, 440, 442 (100:64:10).

EXAMPLE 56

(3,5,dichloro-4-E[cyano-(4-hydroxy-3-sopropylphenyl)-methyl]-6-fluoropyridin-2-ylamino) acetic Acid

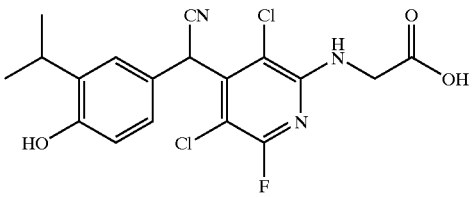

To a solution of {3,5, dichloro-4-[cyano-(3-isopropyl-4-methoxy-phenyl)-methyl]-6-fluoro-pyridin-2-ylamino}-acetic acid methyl ester (35 mg, 0.08 mmol) in CH$_2$Cl$_2$ (2 mL) cooled with an ice-water bath was added boron tribromide (1.0 ml, 1.0 M solution in CH$_2$Cl$_2$, 1.0 mmol). The temperature was allowed to warm up to RT. After 2 h, the mixture was poured into a flask containing ice water (25 mL). The product was extracted with EtOAc (50 mL). The organic extract was washed with brine (25 mL), dried (Na$_2$SO4), filtered and concentrated in vacuo. The crude product isolated was purified by preparative HPLC (from 50% B to 100% B for 10 min, Solvent A=90% H$_2$O–10% MeOH-0.1% TFA Solvent B=10% MeOH-90% H$_2$O–0.1% TFA, at 20 mL/min using column YMC ODS S5 20×100 mm) to afford 24.2 mg (74%) of the title compound as a white solid.

$^1$H NMR (400 MHz, CD$_3$OD, δ) 7.205 (d, 1H, J=2.2 Hz), 6.925 (dd, 1H, J=8.8 Hz, 2.2 Hz), 6.72 (d, 1H, J=8.2 Hz), 6.19 (s, 1H), 4.10 (s, 2H), 3.25 (heptet, 1H, J=6.6 Hz), 1.185,1.165 (2d, 6H, J=7.2, 6.6 Hz); MS–ESI$^-$ [M–H]$^-$= 410, 412, 414 (100:64:10).

EXAMPLE 57

[3,5-Dichloro-6-fluoro-4-(4-hydroxy-3-isopropyl-benzoyl)-pyridin-2-ylamino]-acetic Acid

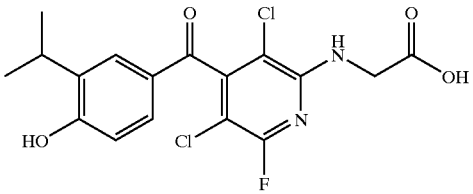

To a solution of crude {3,5, dichloro-4-[cyano-(4-hydroxy-3-isopropyl-phenyl)-methyl]-6-fluoro-pyridin-2-ylamino}-acetic acid (24 mg, 0.058 mmol) in DMSO (2 mL) was added K$_2$CO$_3$ (28 mg, 0.202 mmol) in H$_2$O (2 mL). The mixture was left to stir overnight at ambient room temperature in an open flask. The mixture was acidified with 1N HCl and the product was partitioned between EtOAc (50 mL) and H$_2$O (25 mL). The organic extract was washed with brine (25 mL), dried (Na$_2$SO$_4$), filtered and concentrated in vacuo. The crude product was purified by preparative HPLC (from 50% B to 100% B for 10 min, Solvent A=90% H$_2$O–10% MeOH-0.1% TFA Solvent B=10% MeOH-90%

H₂O–0.1% TFA, at 20 mL/min using column YMC ODS S5 20×100 mm) to afford 7.95 mg (34% for 2 steps) of the title compound.

¹H NMR (400 MHz, CD₃OD, δ) 7.77 (d, 1H, J=1.1 Hz), 7.435 (dd, 1H, J=8.8 Hz, 2.2 Hz), 6.82 (d, 1H, J=8.3 Hz), 4.14 (s, 1H), 4.12 (s, 1H). 3.30–3.27 (m, 1H), 1.225 (d, 6H, J=6.6 Hz)); MS–ESI⁻[M–H]⁻=399, 401, 403 (100:64:10).

The following examples were prepared using the procedures or a variation thereof, as described in the aforementioned examples and schemes.

| Example # | Structure | molecular weight | [M + H]⁺ | [M – H]⁻ |
|---|---|---|---|---|
| 58 | 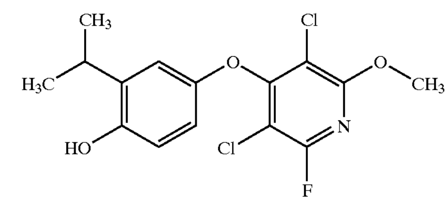 | 346.19 | | 343.88 |
| 59 | 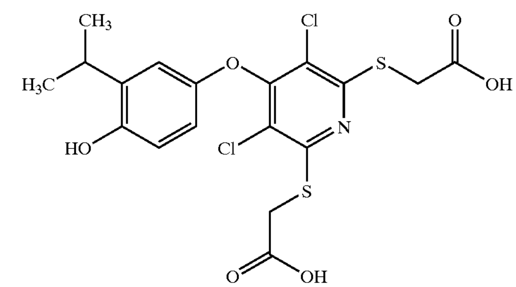 | 478.37 | | 475.74 |
| 60 | 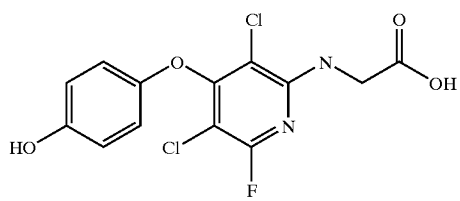 | 347.13 | | 344.85 |
| 61 | 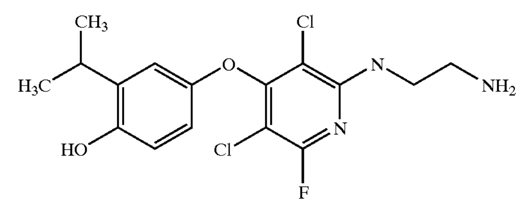 | 374.25 | 374 | 372 |
| 62 | 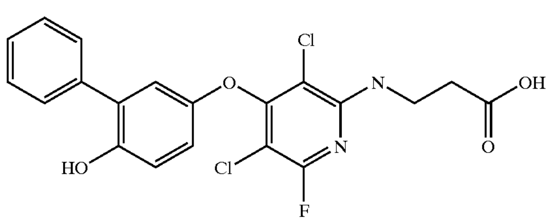 | 437.26 | | 435 |
| 63 | 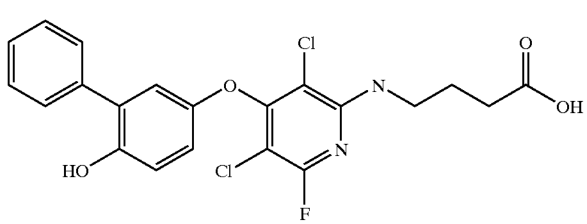 | 451.29 | | 449 |

-continued

| Example # | Structure | molecular weight | [M + H]+ | [M − H]− |
|---|---|---|---|---|
| 64 | 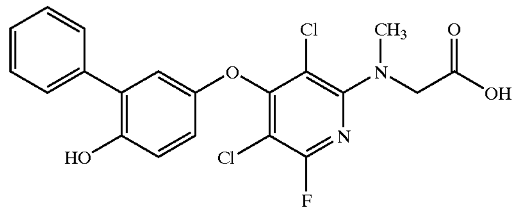 | 437.26 | | 435 |
| 65 | 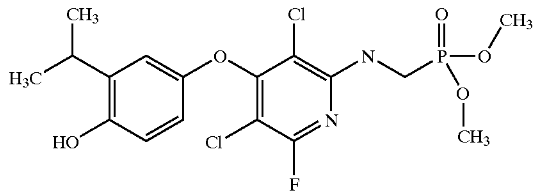 | 453.24 | 455 | |
| 66 | 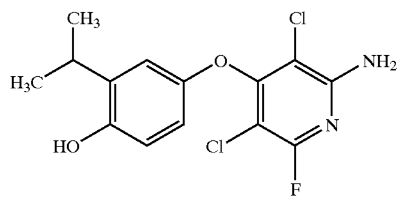 | 331.18 | | 328.9 |
| 67 | 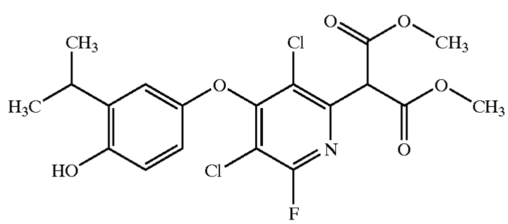 | 446.26 | | 444 |
| 68 | 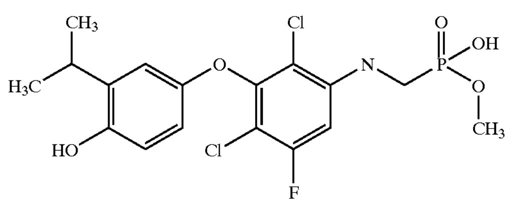 | 439.21 | | 436.9 |
| 69 | 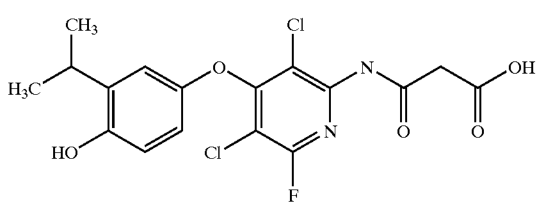 | 417.22 | | 415 |
| 70 | 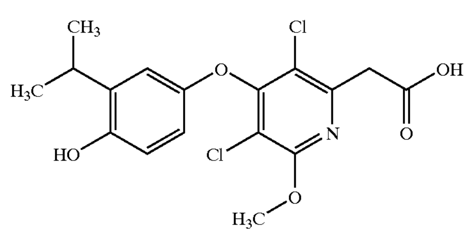 | 386.23 | 385.9 | |

-continued

| Example # | Structure | molecular weight | [M + H]+ | [M − H]− |
|---|---|---|---|---|
| 71 | 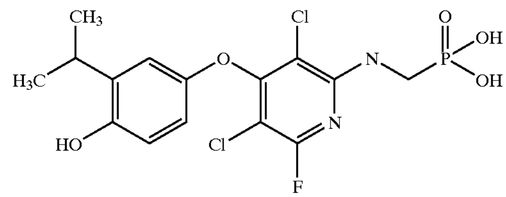 | 425.18 | | 422.8 |
| 72 | 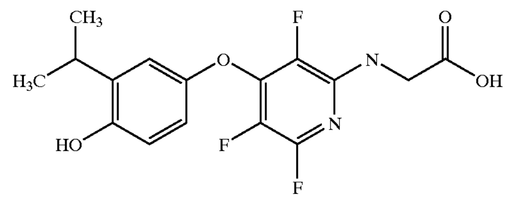 | 356.3 | | 355 |
| 73 | 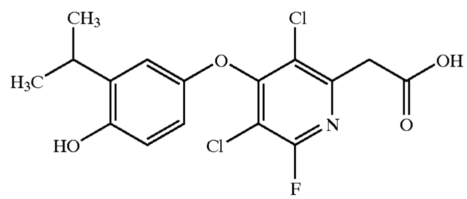 | 374.2 | | 372.1 |
| 74 | 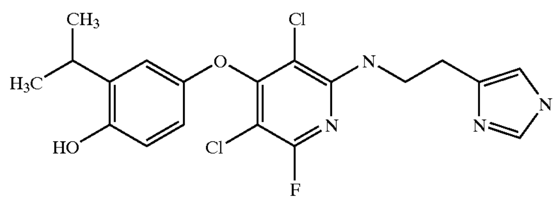 | 425.29 | 426 | 424 |
| 75 | 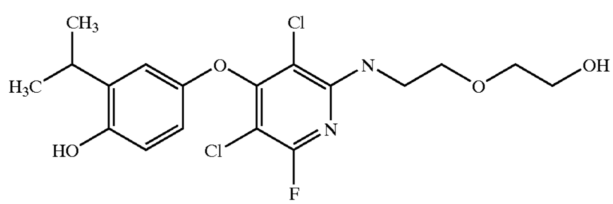 | 419.28 | 419 | 417 |
| 76 | 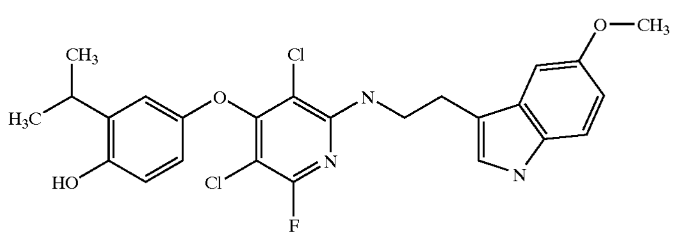 | 504.39 | 505 | 502 |
| 77 | 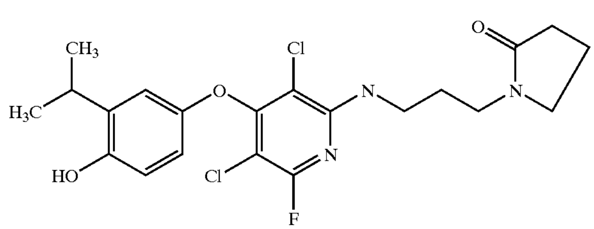 | 456.35 | 456 | |

-continued

| Example # | Structure | molecular weight | [M + H]+ | [M − H]− |
|---|---|---|---|---|
| 78 | 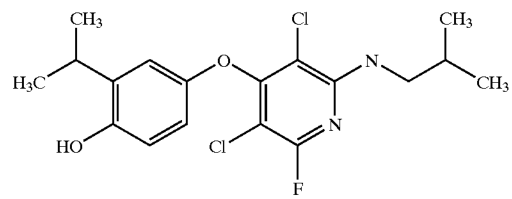 | 387.28 | | 386 |
| 79 | 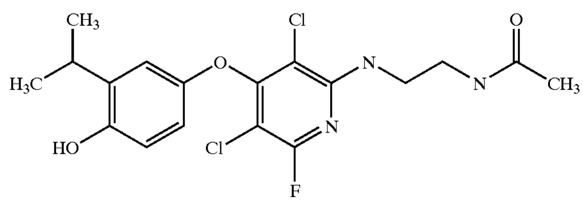 | 416.28 | 416 | 415 |
| 80 | 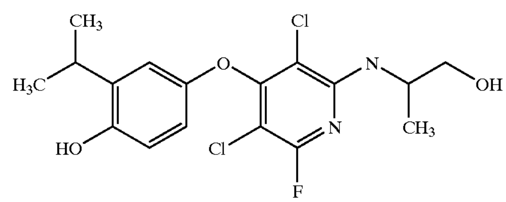 | 389.26 | 389 | 387 |
| 81 | 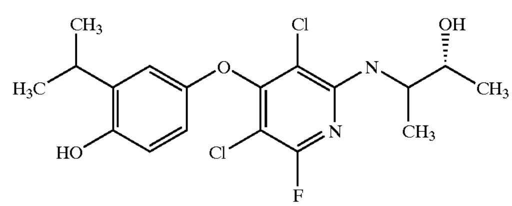 | 403.28 | 403 | 401 |
| 82 | 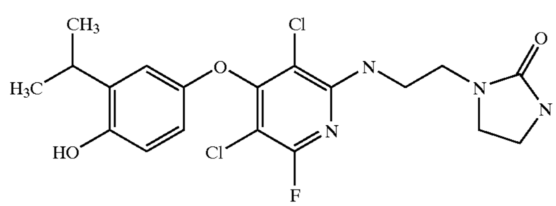 | 440.31 | 441 | |
| 83 | 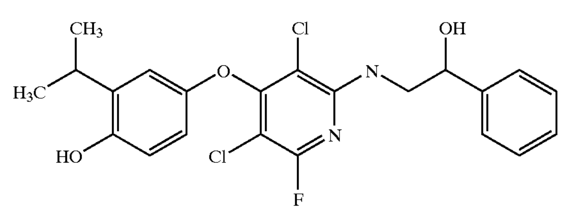 | 451.33 | 451 | 449 |
| 84 | 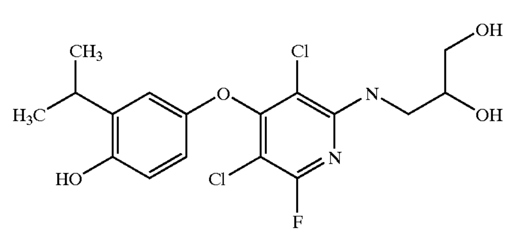 | 404.27 | 405 | 403 |

-continued

| Example # | Structure | molecular weight | [M + H]+ | [M − H]− |
|---|---|---|---|---|
| 85 | Chiral | 403.24 | 401 | |
| 86 | 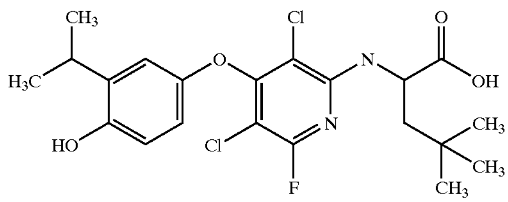 | 459.35 | | 457 |
| 87 | 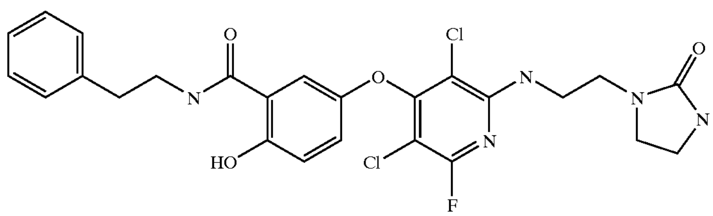 | 546.39 | 548 | |
| 88 | 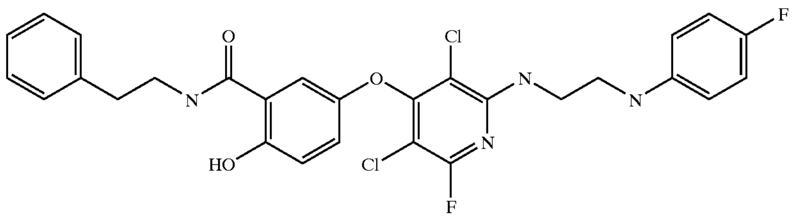 | 573.43 | | 571 |
| 89 | 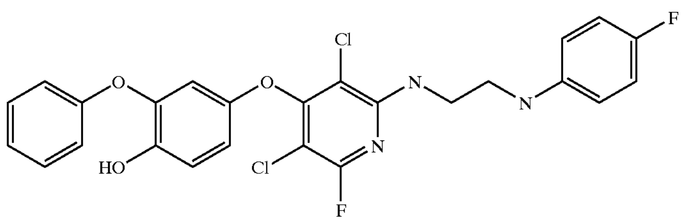 | 518.35 | 516 | |
| 90 | 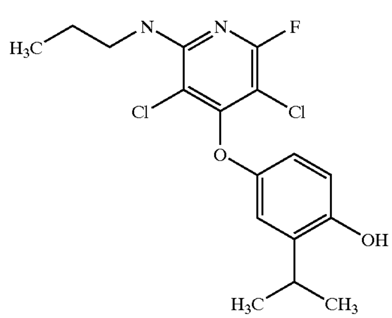 | 373.3 | 373 | |

-continued
| Example # | Structure | molecular weight | [M + H]+ | [M − H]- |
|---|---|---|---|---|
| 91 | 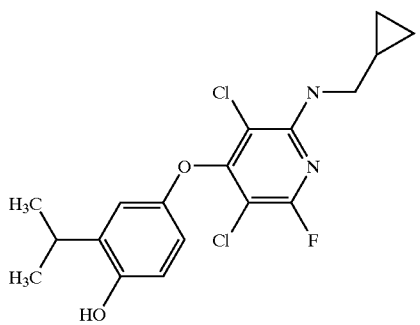 | 385.3 | 385 | 383 |
| 92 | 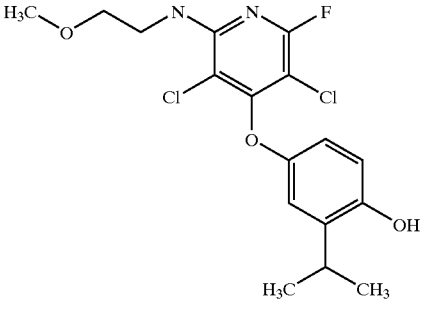 | 389.3 | | 387 |
| 93 | 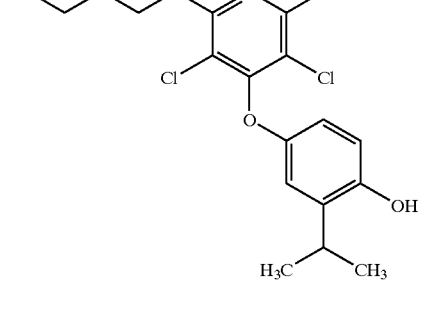 | 389.3 | | 387 |
| 94 | 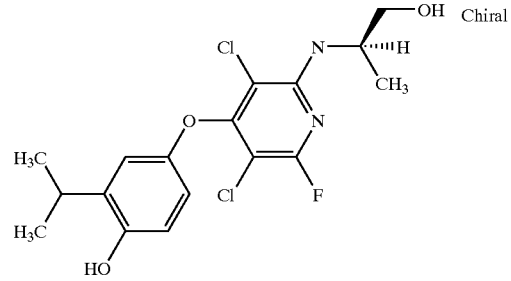 | 389.3 | 389 | 387 |

-continued

| Example # | Structure | molecular weight | [M + H]+ | [M − H]− |
|---|---|---|---|---|
| 95 | (Chiral structure) | 389.3 | 389 | 387 |
| 96 | 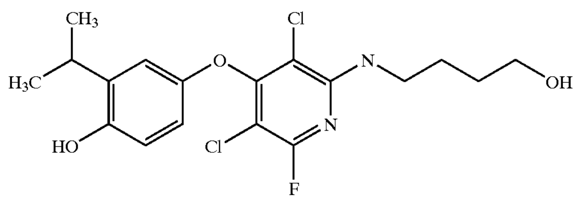 | 403.3 | 403 | 401 |
| 97 | 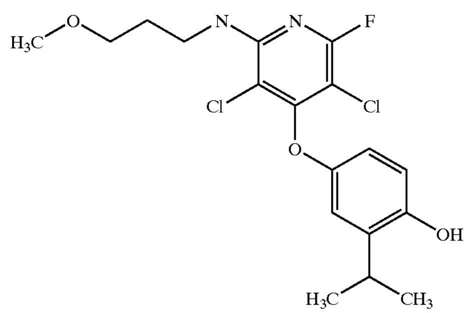 | 403.3 | 403 | 401 |
| 98 | 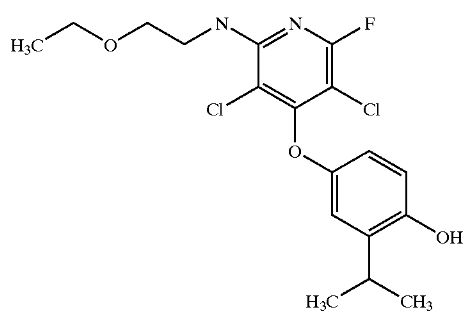 | 403.3 | 403 | 401 |
| 99 | 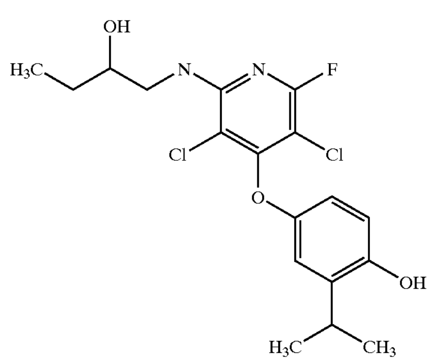 | 403.3 | 403 | 401 |

-continued

| Example # | Structure | molecular weight | [M + H]+ | [M − H]− |
|---|---|---|---|---|
| 100 | 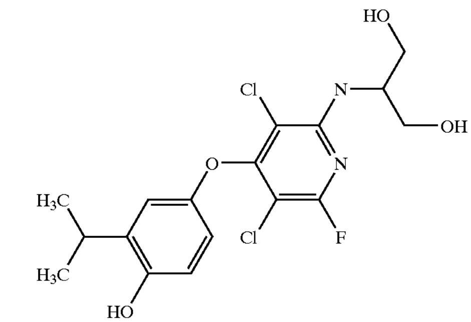 | 405.3 | 405 | 403 |
| 101 | 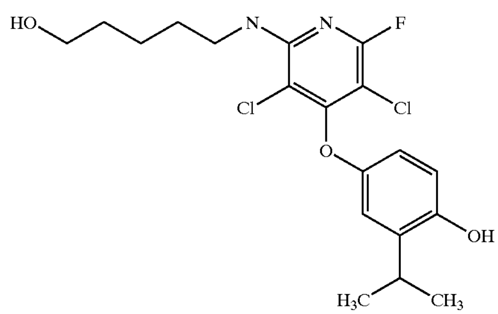 | 417.3 | 417 | 415 |
| 102 | 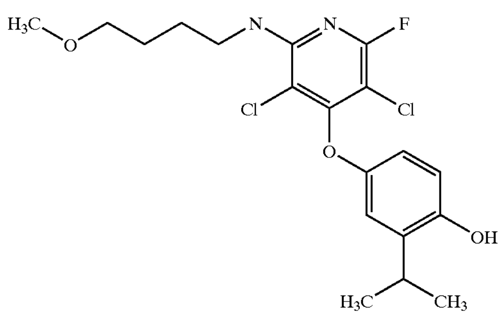 | 417.3 | 417 | 415 |
| 103 | 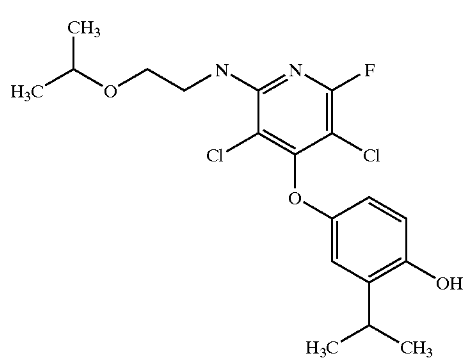 | 417.3 | 417 | 415 |

-continued
| Example # | Structure | molecular weight | [M + H]+ | [M − H]− |
|---|---|---|---|---|
| 104 | 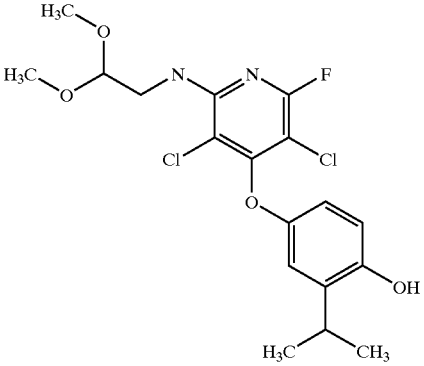 | 419.3 | | 417 |
| 105 | 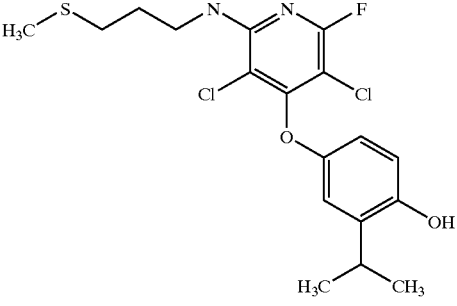 | 419.3 | 419 | 417 |
| 106 | 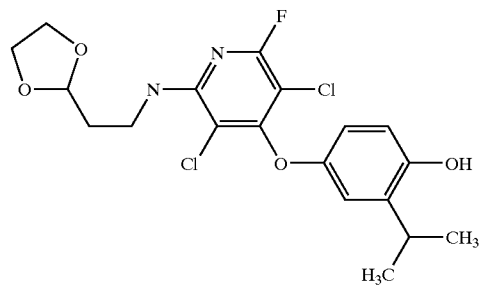 | 431.3 | 431 | |
| 107 | 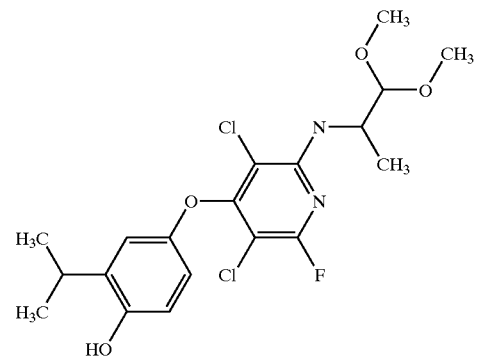 | 433.3 | | 431 |

-continued

| Example # | Structure | molecular weight | [M + H]+ | [M − H]− |
|---|---|---|---|---|
| 108 | 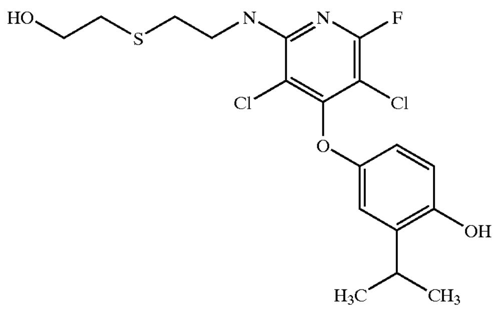 | 435.3 | 435 | 433 |
| 109 | 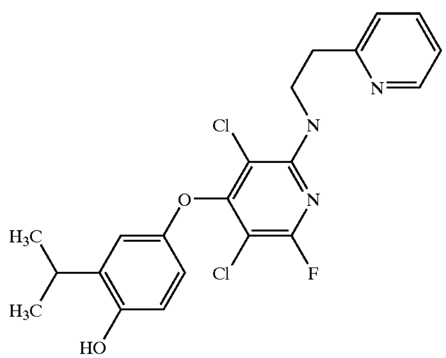 | 436.3 | 436 | 434 |
| 110 | 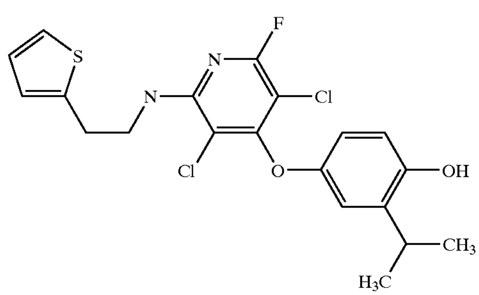 | 441.4 | 441 | |
| 111 | 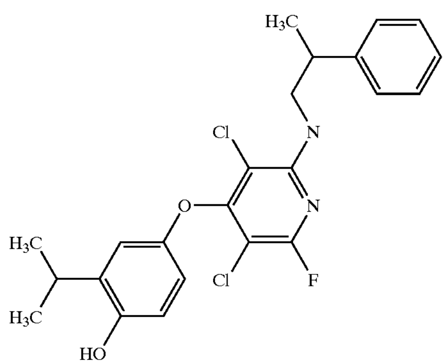 | 449.4 | 449 | 447 |

-continued
| Example # | Structure | molecular weight | [M + H]+ | [M − H]− |
|---|---|---|---|---|
| 112 | 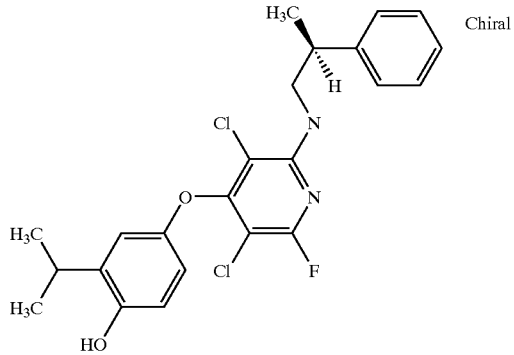 | 449.4 | 450 | |
| 113 | 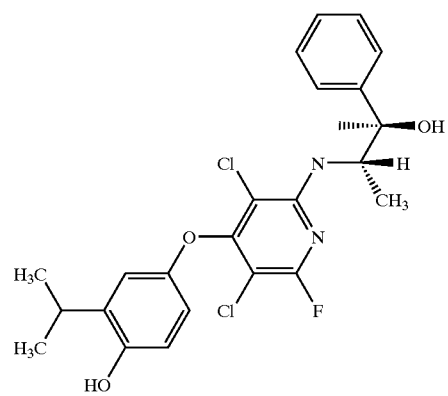 | 465.4 | 465 | |
| 114 | 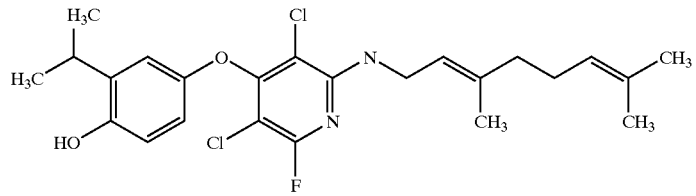 | 467.4 | | 465 |
| 115 | 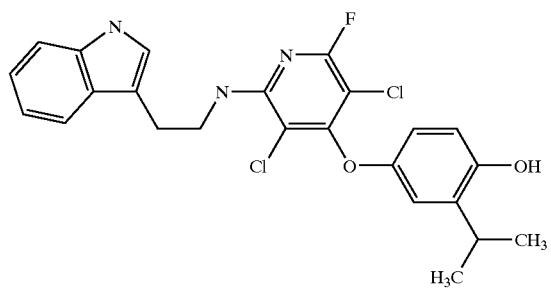 | 474.4 | 474 | 472 |
| 116 | 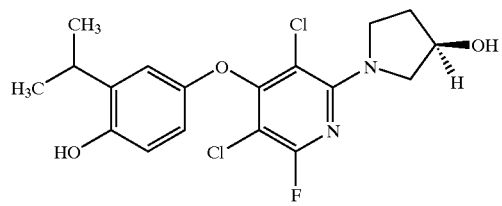 | 401.3 | 401 | 399 |

-continued

| Example # | Structure | molecular weight | [M + H]+ | [M − H]− |
|---|---|---|---|---|
| 117 | 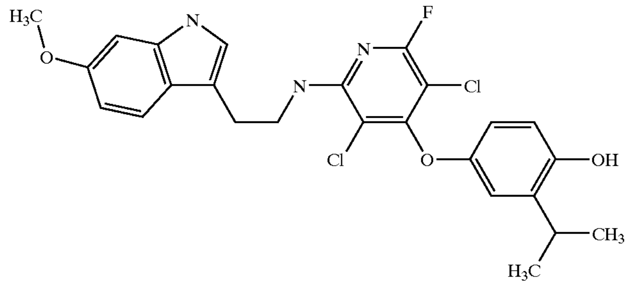 | 504.4 | 504 | 502 |
| 118 | Chiral | 526.3 | 526 | 524 |
| 119 | 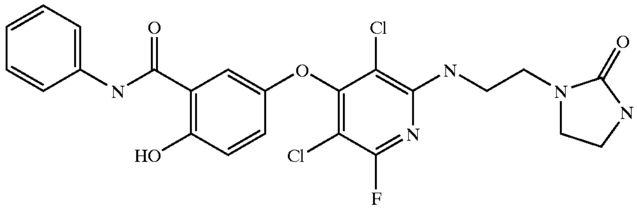 | 520.35 | | 518 |
| 120 | 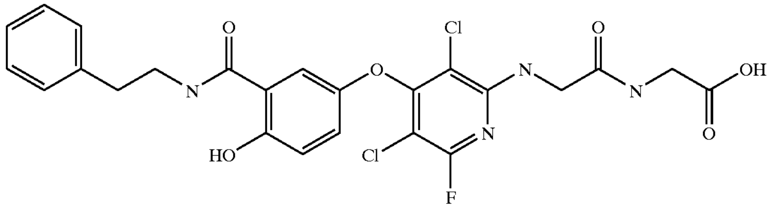 | 551.36 | | 549 |
| 121 | 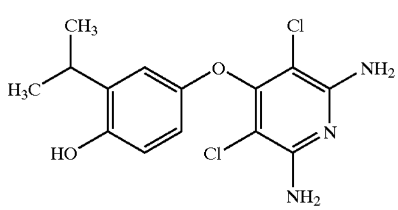 | 328.2 | | 328.05 |
| 122 | 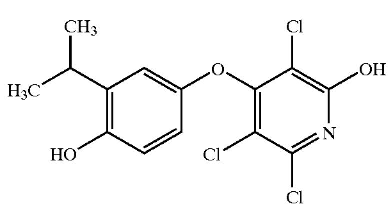 | 348.62 | | 345.9 |

-continued
| Example # | Structure | molecular weight | [M + H]+ | [M − H]- |
|---|---|---|---|---|
| 123 | 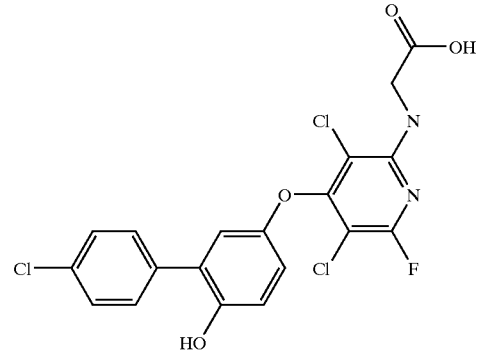 | 457.7 | | 455 |
| 124 | 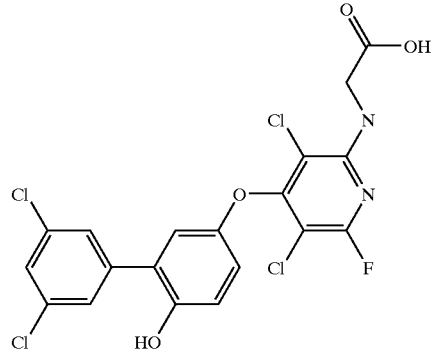 | 492.1 | | 491 |
| 125 | 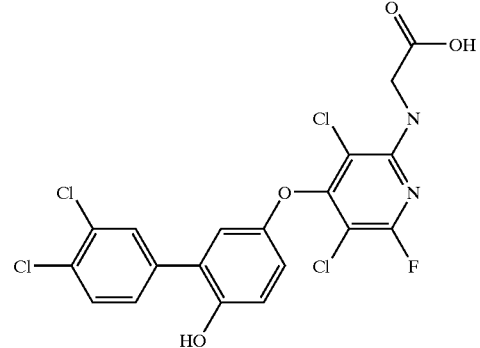 | 492.1 | | 491 |
| 126 | 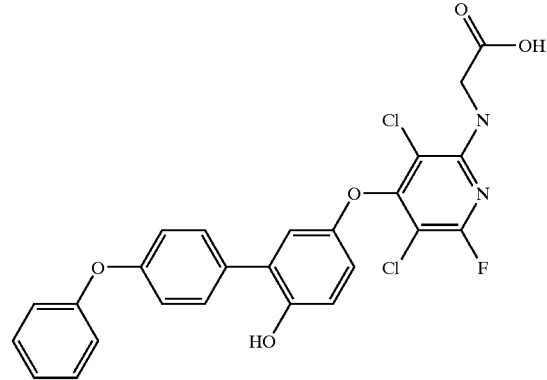 | 515.3 | | 515 |

-continued

| Example # | Structure | molecular weight | [M + H]+ | [M − H]− |
|---|---|---|---|---|
| 127 | 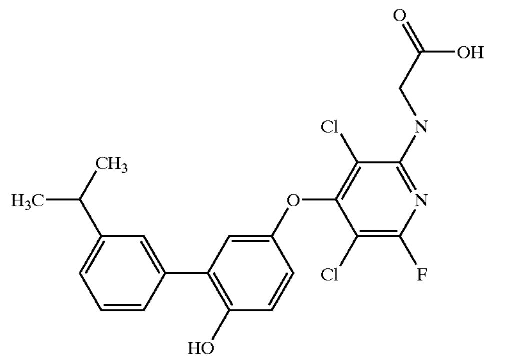 | 465.3 | | 465 |
| 128 | 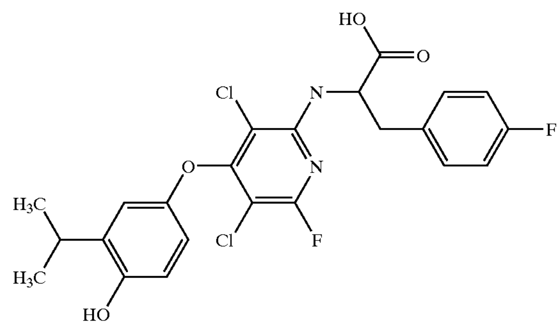 | 497.3 | | 497 |
| 129 | 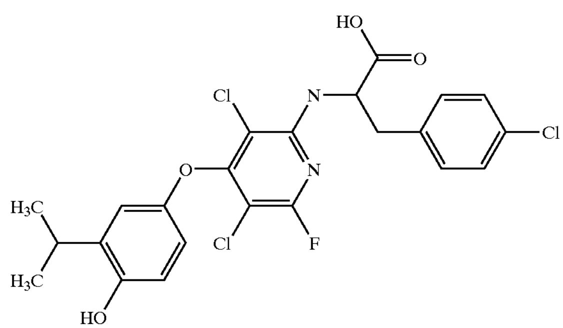 | 513.8 | | 514 |
| 130 | (Chiral) | 445.3 | | 445 |

-continued

| Example # | Structure | molecular weight | [M + H]⁺ | [M − H]⁻ |
|---|---|---|---|---|
| 131 | 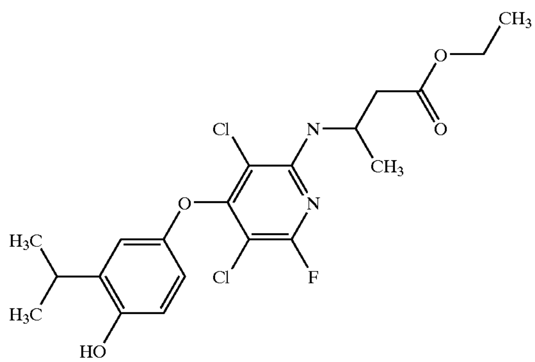 | 445.3 | | 455 |
| 132 | 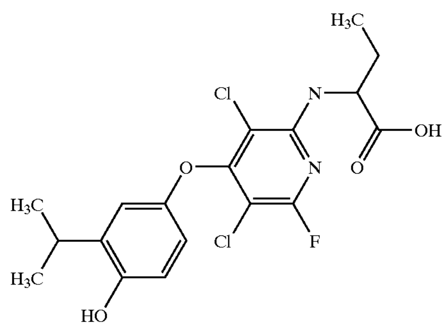 | 417.3 | | 417 |
| 133 | 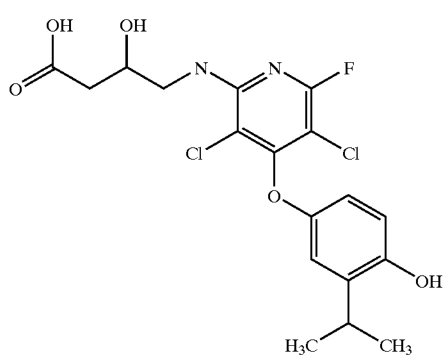 | 433.3 | | 433 |
| 134 | 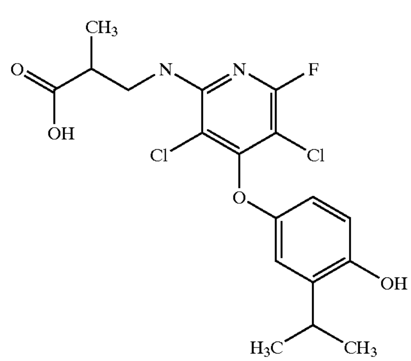 | | | 417 |

-continued

| Example # | Structure | molecular weight | [M + H]+ | [M − H]− |
|---|---|---|---|---|
| 135 | Chiral | 485.91 | | |
| 136 | 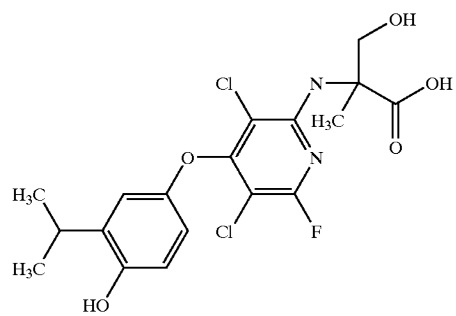 | 432.86 | | |
| 137 | 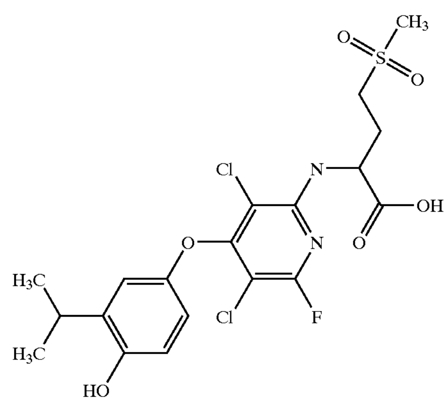 | 494.85 | | |
| 138 | Chiral | 488.88 | | |

| Example # | Structure | molecular weight | [M + H]+ | [M − H]− |
|---|---|---|---|---|
| 139 | 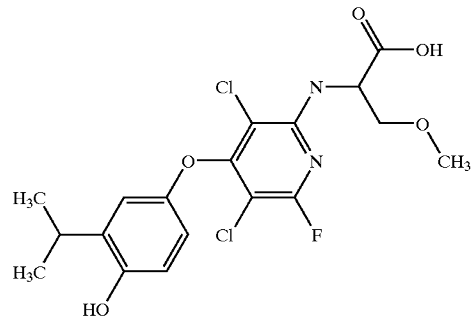 | | | 432.86 |
| 140 | Chiral | 461 | | |
| 141 | Chiral | 462.87 | | |
| 142 | Chiral | 487.88 | | |

-continued

| Example # | Structure | molecular weight | [M + H]+ | [M − H]− |
|---|---|---|---|---|
| 143 | 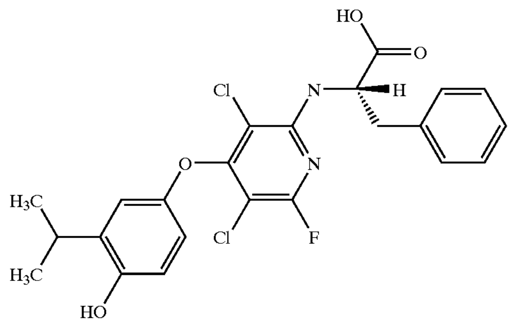 | 478.89 | | |
| 144 | 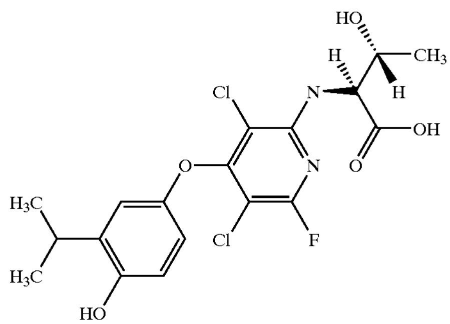 | 432.88 | | |
| 145 | 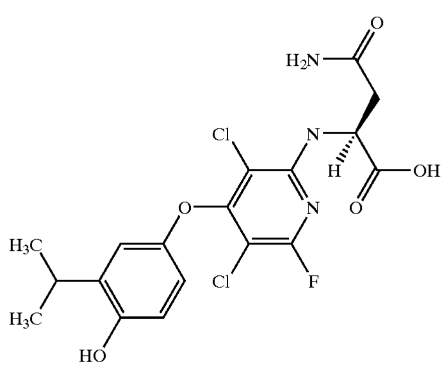 | 446.14 | | |
| 146 | 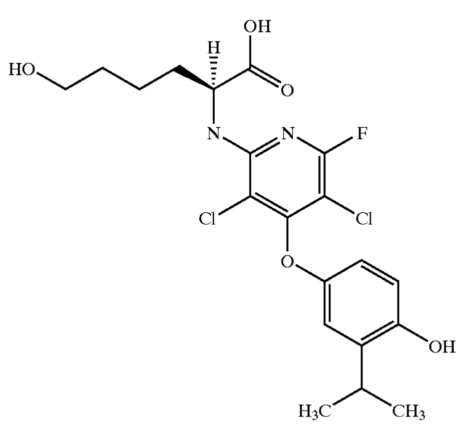 | 460.9 | | |

-continued

| Example # | Structure | molecular weight | [M + H]+ | [M − H]− |
|---|---|---|---|---|
| 147 | 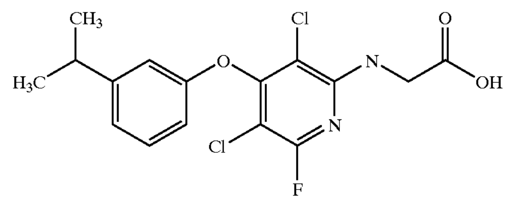 | 373.21 | | 371.1 |
| 148 | 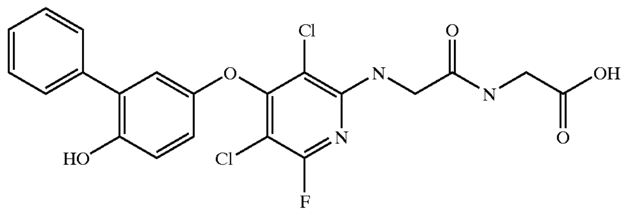 | 480.28 | | 478 |
| 149 | 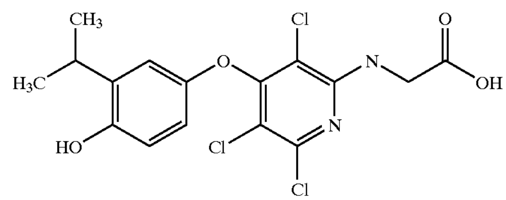 | 405.67 | | 403.1 |
| 150 | 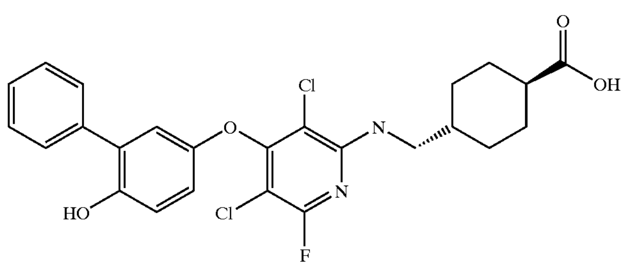 | 505.38 | | 503 |
| 151 | 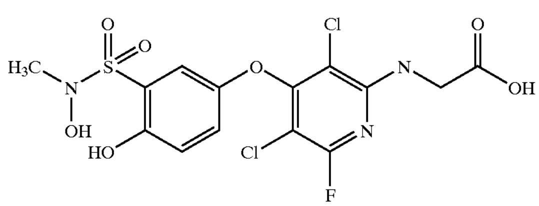 | 454.26 | | 452 |
| 152 | 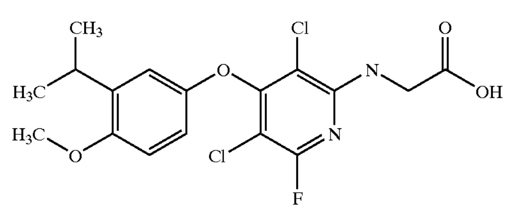 | 403.24 | | 401.3 |

| Example # | Structure | molecular weight | [M + H]+ | [M − H]− |
|---|---|---|---|---|
| 153 | 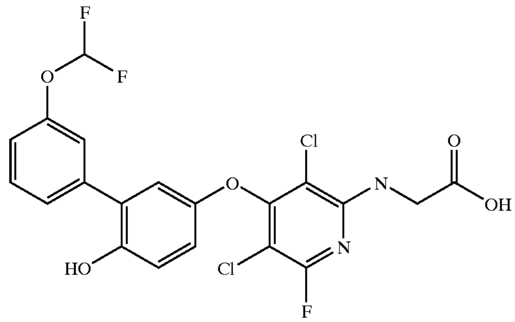 | 489.24 | | 487 |
| 154 | 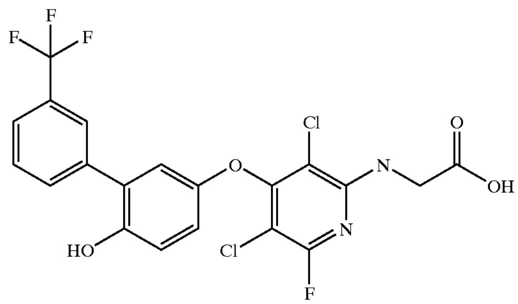 | 491.23 | | 489 |
| 155 | 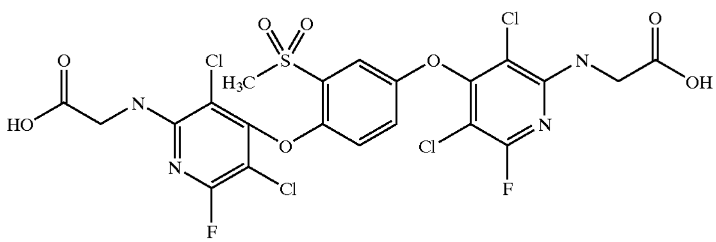 | 662.24 | | 661 |
| 156 | Chiral | 417.3 | | 417.16 |
| 157 | Chiral | 417.3 | | 417.15 |

-continued

| Example # | Structure | molecular weight | [M + H]+ | [M − H]− |
|---|---|---|---|---|
| 158 | 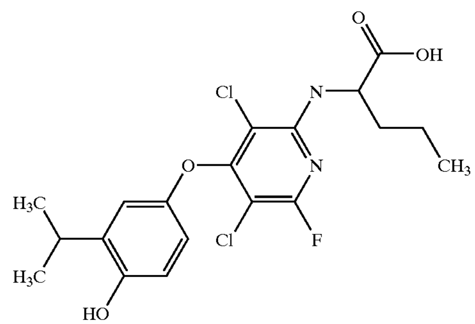 | 431.3 | 431.16 | |
| 159 | 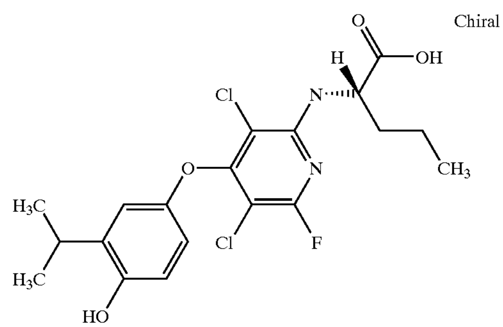 | 431.3 | 431.16 | |
| 160 | 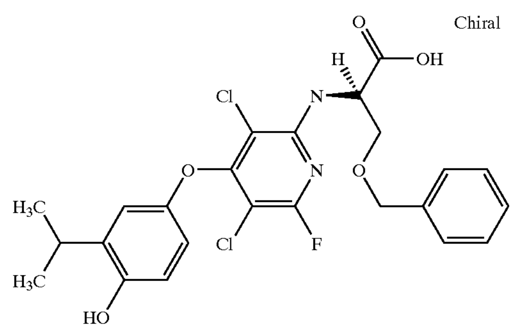 | 509.4 | 509.19 | |
| 161 | 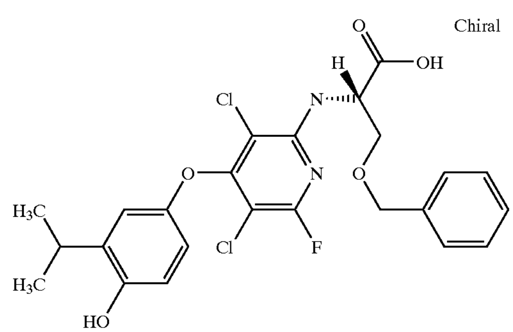 | 509.4 | 509.17 | |

| Example # | Structure | molecular weight | [M + H]+ | [M − H]− |
|---|---|---|---|---|
| 162 | (Chiral) | 495.4 | | 495.12 |
| 163 | (Chiral) | 445.3 | | 445.17 |
| 164 | (Chiral) | 445.3 | | 445.14 |
| 165 | (Chiral) | 485.4 | | 485.1 |

| Example # | Structure | | molecular weight | [M + H]+ | [M – H]- |
|---|---|---|---|---|---|
| 166 | (structure) | Chiral | 513.8 | 514 | |
| 167 | (structure) | Chiral | 513.8 | 514 | |
| 168 | (structure) | Chiral | 493.4 | 493.16 | |
| 169 | (structure) | Chiral | 433.3 | 433.15 | |

-continued

| Example # | Structure | | molecular weight | [M + H]+ | [M − H]− |
|---|---|---|---|---|---|
| 170 | 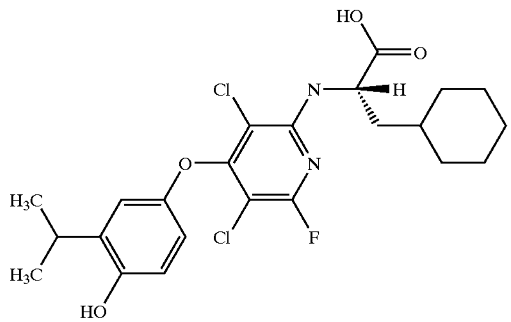 | Chiral | 485.4 | | 485.17 |
| 171 | 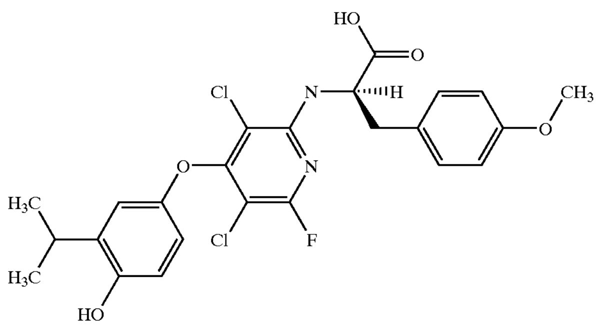 | Chiral | 509.4 | | 509.17 |
| 172 | 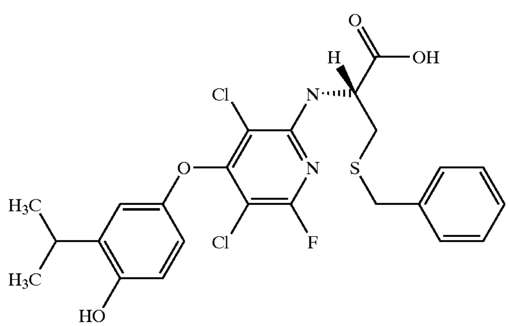 | Chiral | 525.4 | | 525.14 |
| 173 | 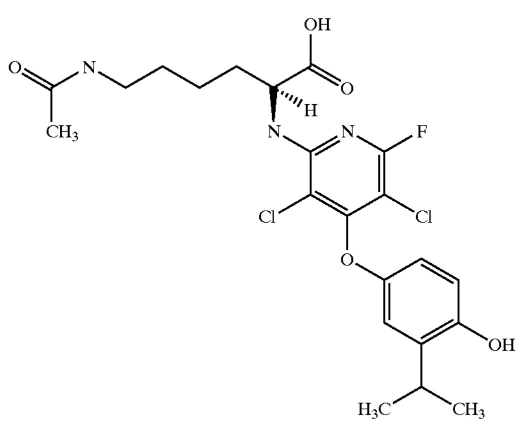 | Chiral | 502.4 | | 502.19 |

| Example # | Structure | molecular weight | [M + H]+ | [M − H]- |
|---|---|---|---|---|
| 174 | (structure, Chiral) | 419.2 | 419.15 | |
| 175 | (structure) | 446.3 | 446.12 | |
| 176 | (structure) | 419.2 | 419.13 | |
| 177 | (structure) | 431.3 | 431.3 | |
| 178 | (structure) | 402.26 | 402.1 | 400.1 |

| Example # | Structure | molecular weight | [M + H]+ | [M − H]− |
|---|---|---|---|---|
| 179 | 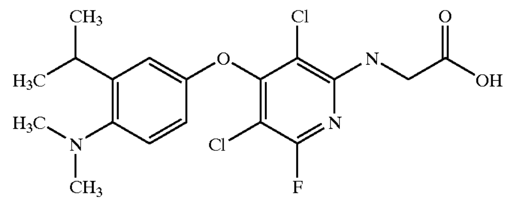 | 416.28 | 416.21 | |
| 180 | 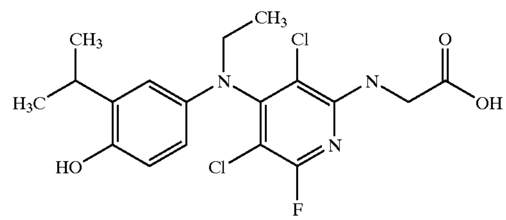 | 416.28 | | 414.23 |
| 181 | 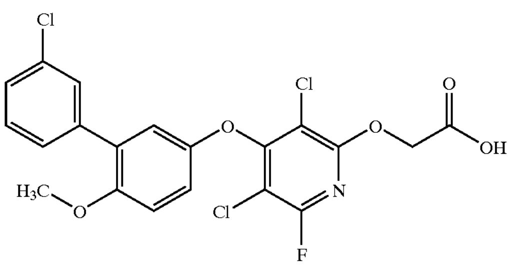 | 472.69 | | 471.6 |
| 182 | 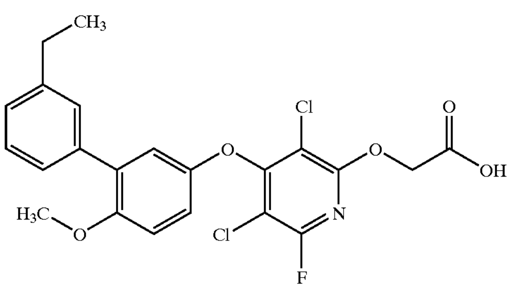 | 466.3 | | 463.7 |
| 183 | 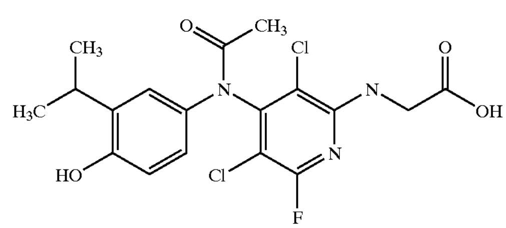 | 430.27 | 430.38 | 428.34 |
| 184 | 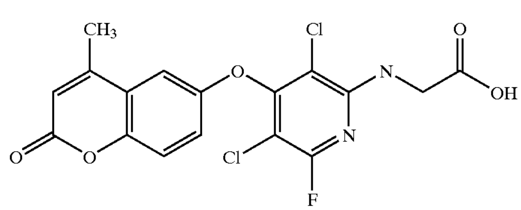 | 413.19 | | 410.6 |

-continued

| Example # | Structure | molecular weight | [M + H]+ | [M − H]− |
|---|---|---|---|---|
| 185 | 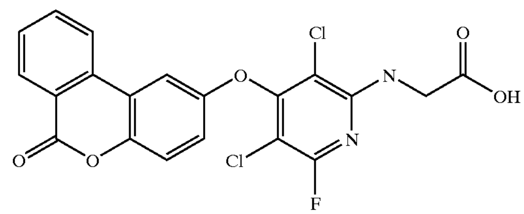 | 449.23 | | 446.6 |
| 186 | 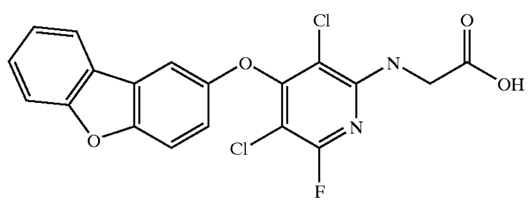 | 421.21 | | 418.7 |
| 187 | 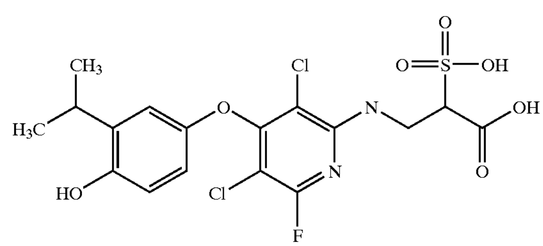 | 483.3 | | 481.28 |
| 188 | Chiral | 405.26 | | 403 |
| 189 | Chiral | 405.26 | | 403 |
| 190 | Chiral | 418.26 | 418.1 | 415.9 |

| Example # | Structure | molecular weight | [M + H]+ | [M − H]− |
|---|---|---|---|---|
| 191 | 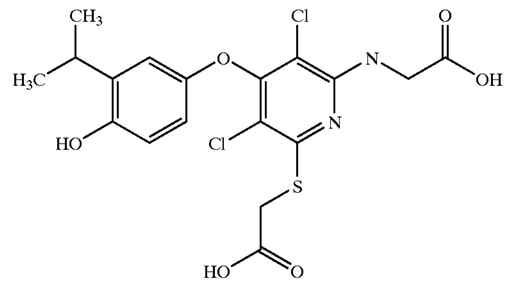 | 461.32 | | 459 |
| 192 | 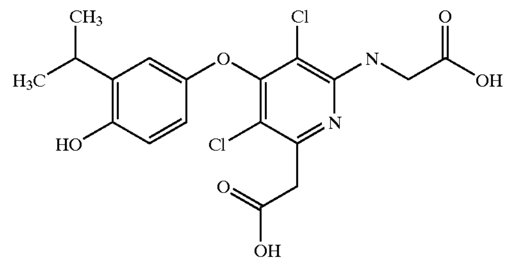 | 429.26 | 429 | |
| 193 | 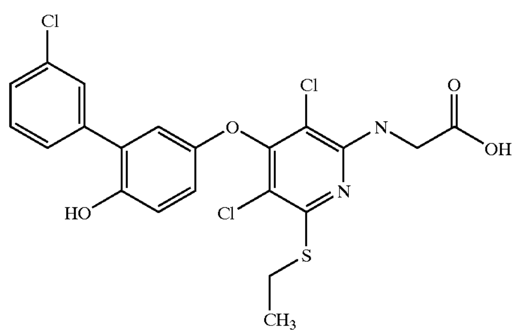 | 499.8 | 499.1 | |
| 194 | 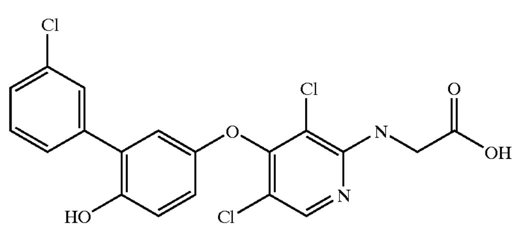 | 439.69 | | 439 |
| 195 | 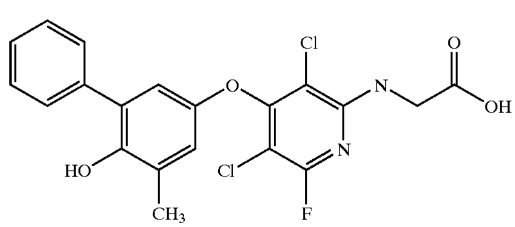 | 437.26 | 437 | 435 |
| 196 | 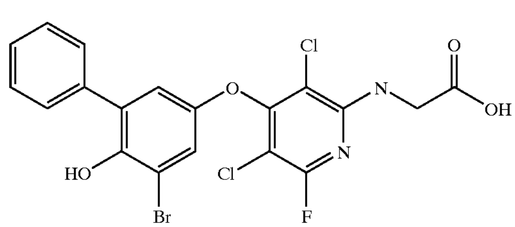 | 502.13 | 502 | |

-continued

| Example # | Structure | molecular weight | [M + H]+ | [M − H]− |
|---|---|---|---|---|
| 197 | 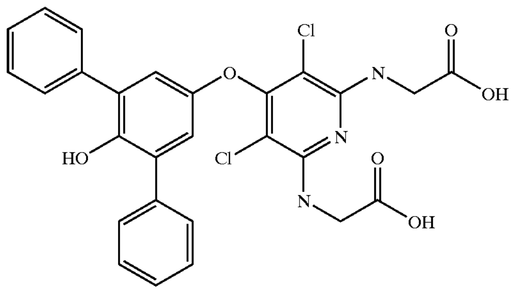 | 554.39 | 554 | |
| 198 | 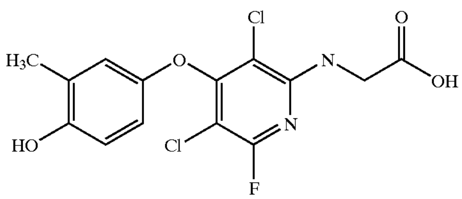 | 361.16 | | 359 |
| 199 | 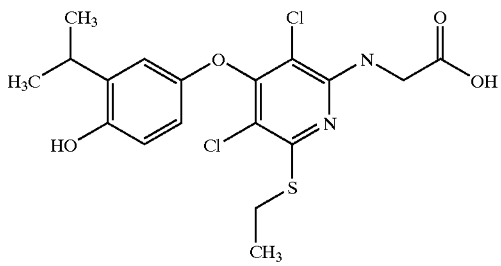 | 431.34 | | 428.8 |
| 200 | 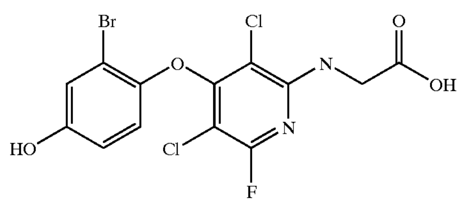 | 426.03 | | 424.9 |
| 201 | 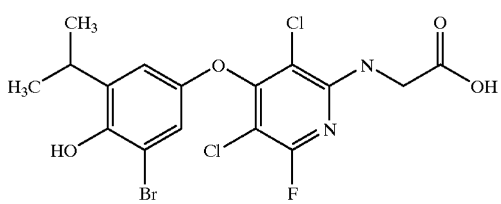 | 468.11 | | 466 |
| 202 | 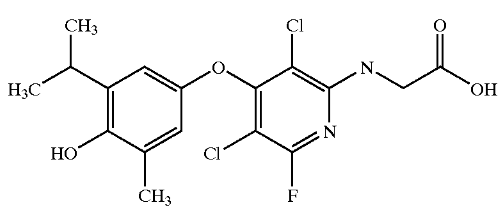 | 403.24 | | 401 |

-continued

| Example # | Structure | molecular weight | [M + H]+ | [M − H]− |
|---|---|---|---|---|
| 203 | 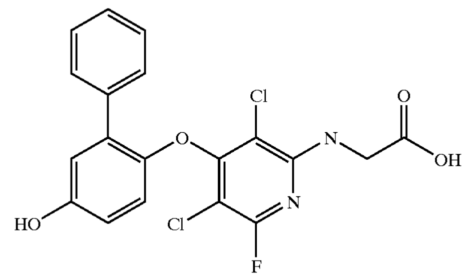 | 423.23 | | 421 |
| 204 | 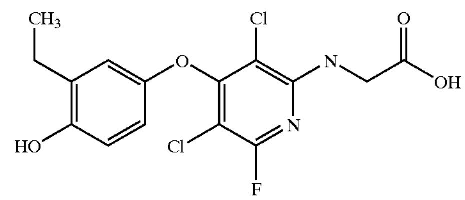 | 375.19 | | 373 |
| 205 | 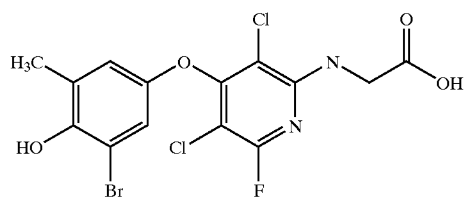 | 440.06 | | 438 |
| 206 | 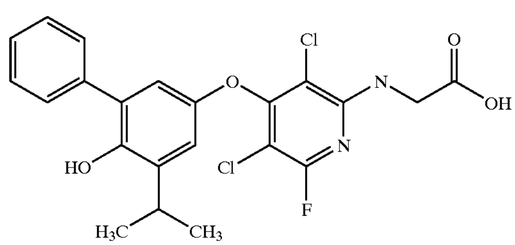 | 465.31 | | 463 |
| 207 | 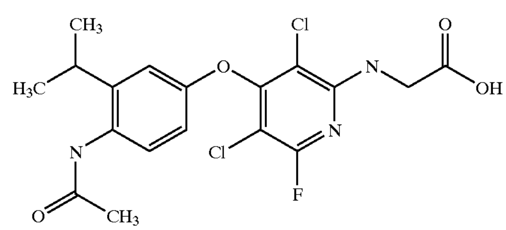 | 430.27 | 430.18 | 428.1 |
| 208 | 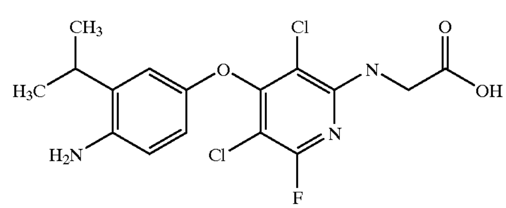 | 388.23 | 388.11 | 386 |

-continued

| Example # | Structure | molecular weight | [M + H]+ | [M − H]− |
|---|---|---|---|---|
| 209 | 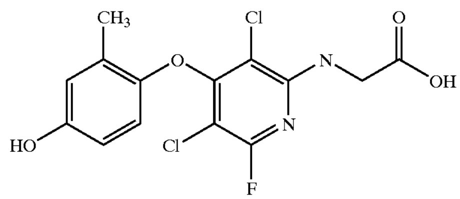 | 361.16 | | 358.9 |
| 210 | 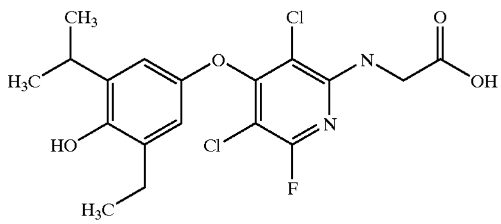 | 417.27 | | 415 |
| 211 | 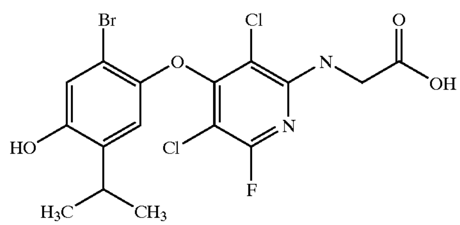 | 468.11 | | 466 |
| 212 | 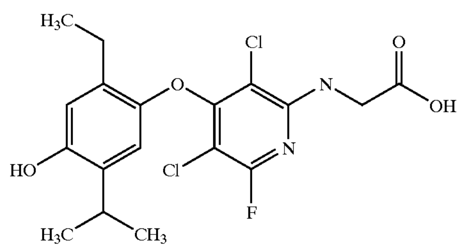 | 417.27 | | 415 |
| 213 | 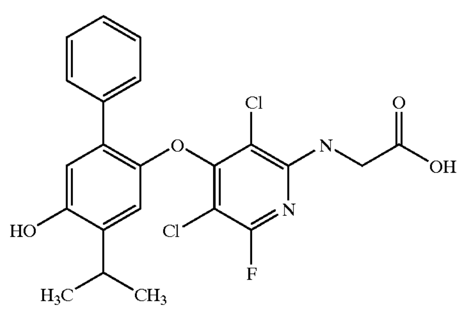 | 465.31 | | 463 |
| 214 | 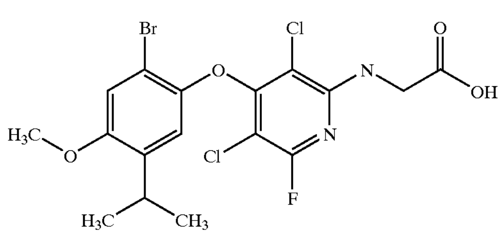 | 482.14 | | 481 |

-continued

| Example # | Structure | molecular weight | [M + H]+ | [M − H]− |
|---|---|---|---|---|
| 215 | 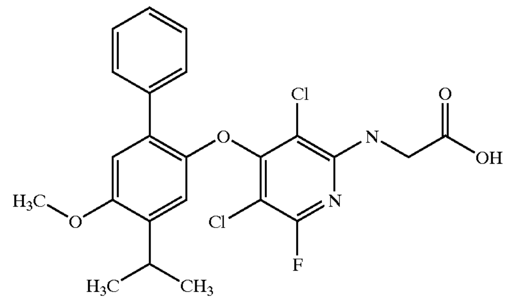 | 479.34 | | 477 |
| 216 | 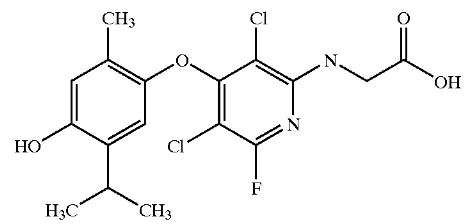 | 403.24 | | 401 |
| 217 | 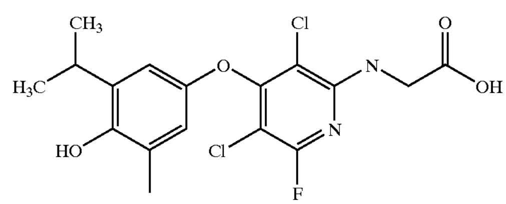 | 515.11 | | 513 |
| 218 | 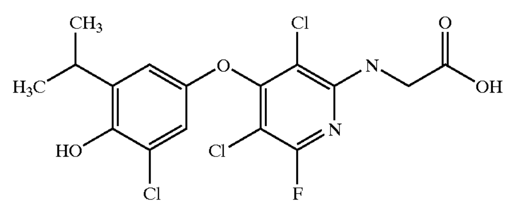 | 423.66 | | 421 |
| 219 | 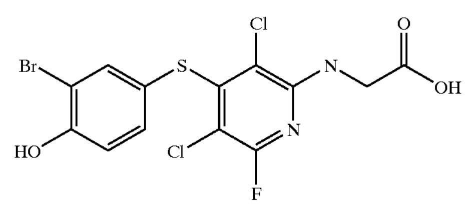 | 442.09 | | 438.88 |
| 220 | 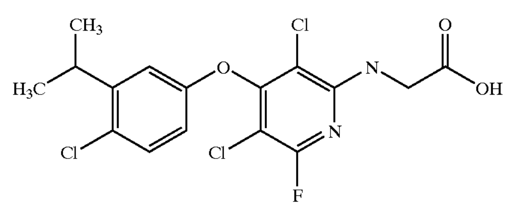 | 407.66 | | 405.02 |
| 221 | 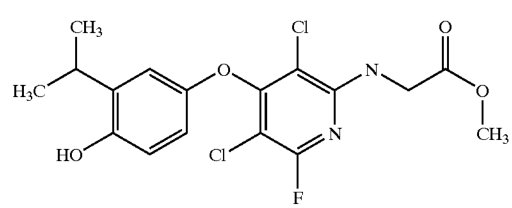 | 403.24 | | 401 |

-continued

| Example # | Structure | molecular weight | [M + H]+ | [M − H]− |
|---|---|---|---|---|
| 222 | 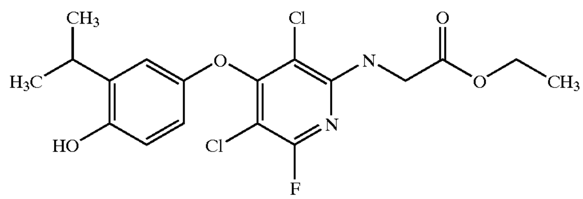 | 417.27 | | 414.9 |
| 223 | 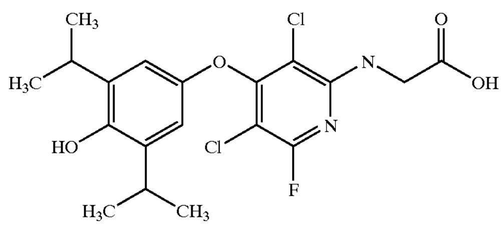 | 431.29 | | 429 |
| 224 | 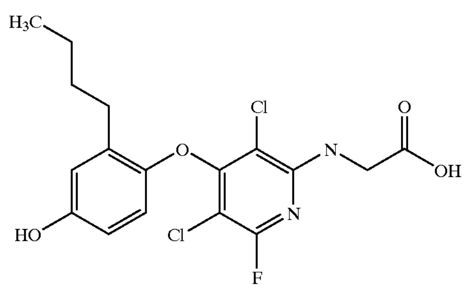 | 403.24 | | 401 |
| 225 | 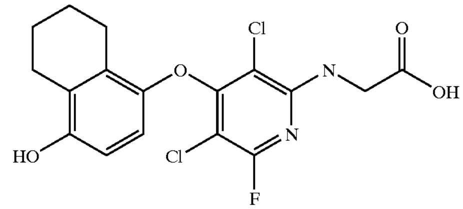 | 401.22 | | 399 |
| 226 | 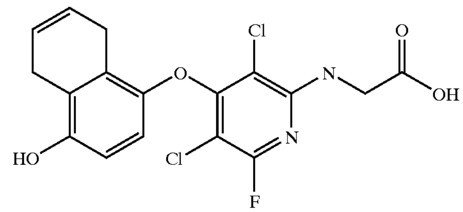 | 399.21 | | 396.9 |
| 227 | 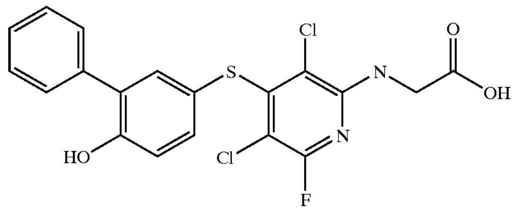 | 439.3 | | 437.11 |

-continued

| Example # | Structure | molecular weight | [M + H]+ | [M − H]− |
|---|---|---|---|---|
| 228 | 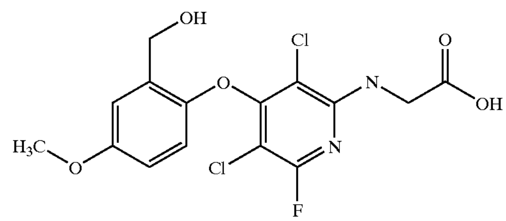 | 391.19 | | 388.9 |
| 229 | 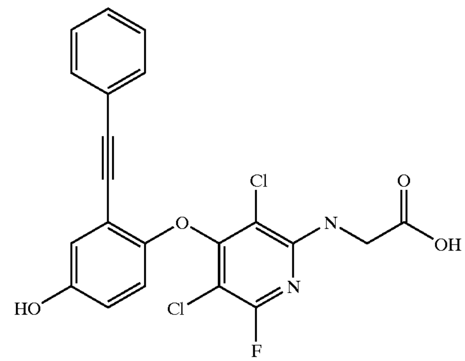 | 447.25 | | 445 |
| 230 | 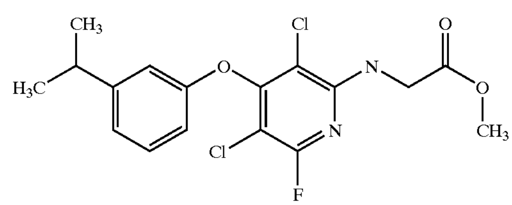 | 387.24 | | 384.8 |
| 231 | 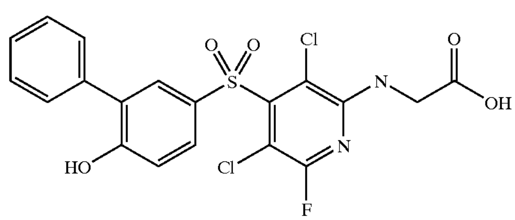 | 471.29 | | 468.98 |
| 232 | 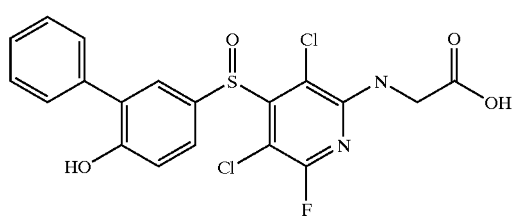 | 455.29 | | 452.98 |
| 233 | 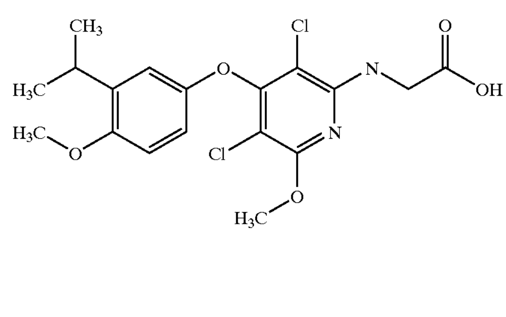 | 415.28 | | 414 |

-continued

| Example # | Structure | molecular weight | [M + H]+ | [M − H]− |
|---|---|---|---|---|
| 234 | 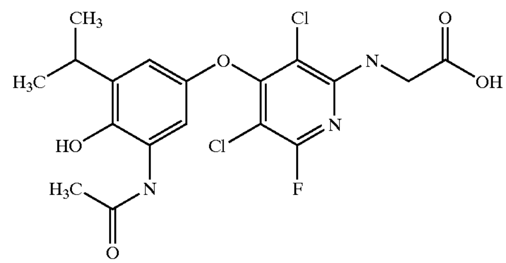 | 446.27 | | 444 |
| 235 | 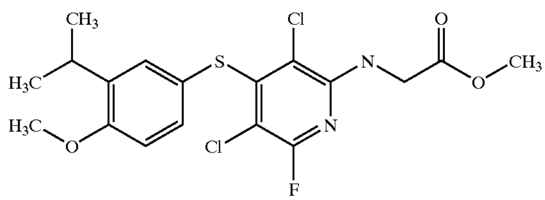 | 433.33 | 433.13 | 431.1 |
| 236 | 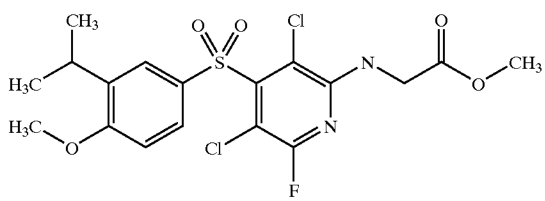 | | | 463.01 |
| 237 | 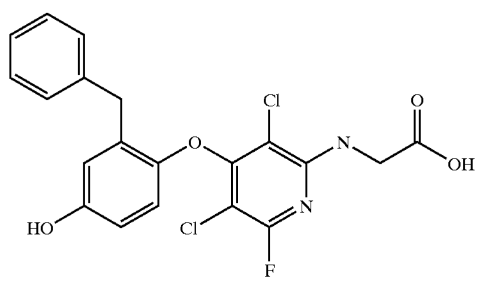 | 437.26 | | 435 |
| 238 | 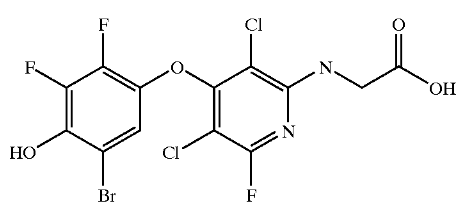 | 462.01 | | 460 |
| 239 | 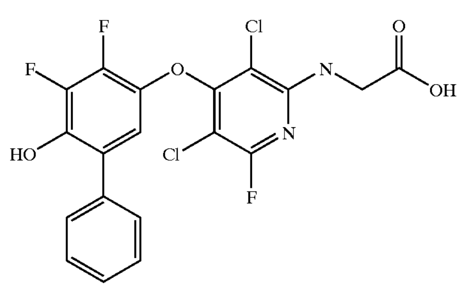 | 459.21 | | 457 |

-continued

| Example # | Structure | molecular weight | [M + H]+ | [M − H]− |
|---|---|---|---|---|
| 240 | 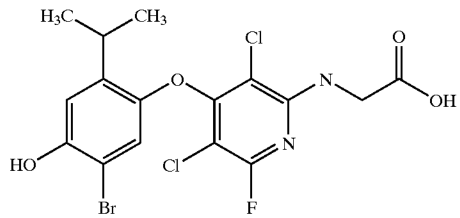 | 468.11 | | 466 |
| 241 | 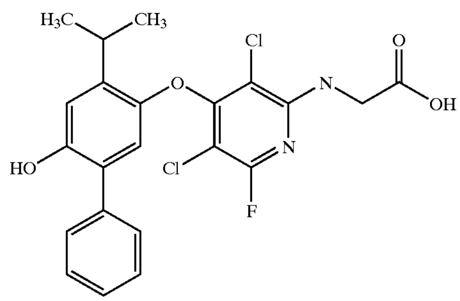 | 465.31 | | 463 |
| 242 | 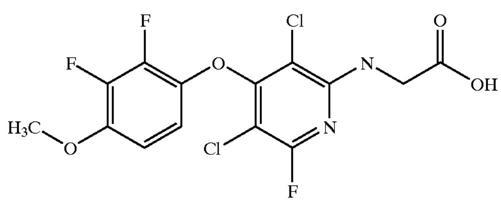 | 397.14 | | 395 |
| 243 | 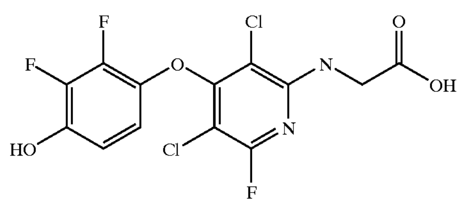 | 383.11 | | 381 |
| 244 | 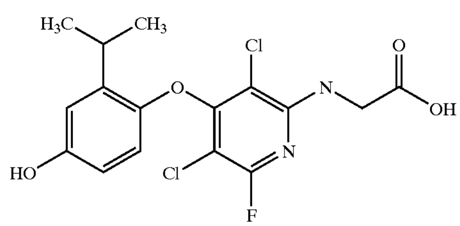 | 389.21 | | 386.9 |
| 245 | 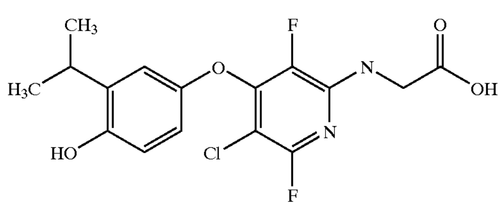 | 372.76 | | 370.8 |

| Example # | Structure | molecular weight | [M + H]+ | [M − H]− |
|---|---|---|---|---|
| 246 | 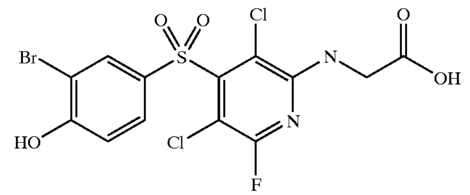 | 474.09 | | 472.7 |
| 247 | 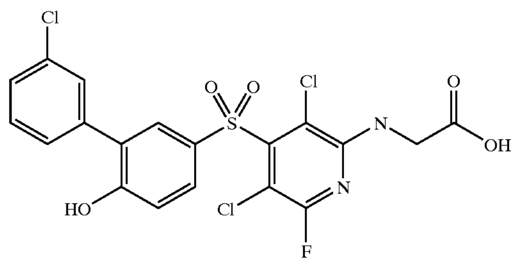 | 505.74 | | 504.8 |

What is claimed is:

1. A compound of the formula

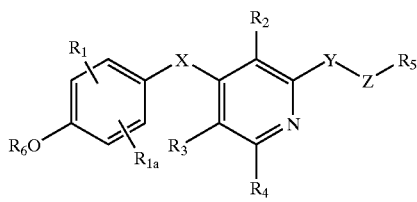

wherein
- X is selected from the group consisting of oxygen, sulfur, sulfoxide, sulfonyl, —$CR_8R_8'$— and —$NR_8$;
- Y is selected from the group consisting of —$NR_8$, oxygen, —$CH_2$— and sulfur;
- Z is a bond or substituted or unsubstituted $C_{1-4}$ alkyl;
- $R_1$ is selected from the group consisting of halogen, trifluoromethyl, substituted or unsubstituted $C_{1-6}$ alkyl, substituted or unsubstituted aryl, substituted or unsubstituted heteroaryl, aryloxy, substituted amide, sulfone, sulfonamide and $C_{3-7}$ cycloalkyl, wherein said aryl, heteroaryl or cycloalkyl ring(s) are attached or fused to the aromatic ring;
- $R_{1a}$ is selected from the group consisting of hydrogen, halogen, substituted or unsubstituted $C_{1-6}$ alkyl, substituted or unsubstituted aryl and substituted or unsubstituted heteroaryl;
- $R_2$ and $R_3$ are each independently selected from the group consisting of hydrogen, halogen, unsubstituted or substituted $C_{1-4}$ alkyl and unsubstituted or substituted $C_{3-5}$ cycloalkyl, wherein at least one of $R_2$ and $R_3$ being other than hydrogen;
- $R_4$ is selected from the group consisting of hydrogen, halogen, amino, O—$R_7$ and S—$R_7$;
- $R_5$ is selected from the group consisting of hydroxyl, carboxylic acid, sulfonic acid and phosphonic acid;
- $R_6$ is selected from the group consisting of hydrogen, alkyl, alkanoyl and aroyl;
- $R_7$ is hydrogen or $C_{1-4}$ alkyl;
- $R_8$ for each occurrence is independently selected from the group consisting of hydrogen, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy and hydroxyl; and
- $R_8'$ is selected from the group consisting of hydrogen, a bond, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy and hydroxyl, or $R_8$ and $R_8'$ together form a carbonyl, including all prodrug, stereoisomers and pharmaceutically acceptable salts thereof.

2. The compound as defined in claim 1 wherein
- X is selected from the group consisting of oxygen, sulfur, sulfoxide, sulfonyl, —$CH_2$— and —NH—;
- Y is —NH— or oxygen;
- $R_1$ is selected from the group consisting of halogen, substituted or unsubstituted $C_{1-6}$ alkyl, substituted aryl, aryloxy, substituted amide, sulfone, sulfonamide and $C_{3-7}$ cycloalkyl, wherein $R_1$ is attached ortho to the $R_6O$ group;
- $R_2$ and $R_3$ are each independently selected from the group consisting of iodo, bromo, chloro and fluoro;
- $R_4$ is selected from the group consisting of hydrogen, fluoro, chloro, amino, —$OCH_3$ and hydroxyl;
- $R_5$ is carboxylic acid; and
- $R_6$ is hydrogen.

3. The compound as defined in claim 1 wherein
- X is selected from the group consisting of carbonyl, $CHR_A$ and $NR_A$;

Y is oxygen or —NH—;

R₁ is selected from the group consisting of halogen, substituted or unsubstituted $C_{1-6}$ alkyl, substituted aryl, substituted amide, sulfone, sulfonamide and $C_{3-7}$ cycloalkyl;

R₂ and R₃ each independently are selected from the group consisting of bromo, chloro and methyl;

R₄ is selected from the group consisting of hydrogen, fluoro, chloro, hydroxyl, amino and methoxy;

R₅ is carboxylic acid; and

R₆ is hydrogen.

4. The compound as defined in claim 1 having the structure

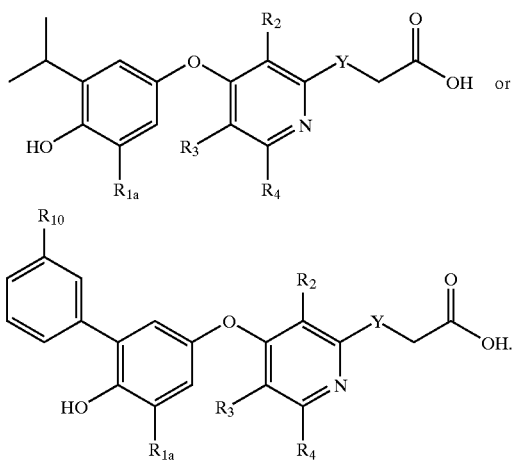

5. The compound as defined in claim 4 wherein

Y is oxygen or —NH—;

R₂ and R₃ are halogen;

R₄ is selected from the group consisting of hydrogen, halogen, amino, —OCH₃ and hydroxyl; and R₁₀ is selected from the group consisting of hydrogen, halogen and substituted and unsubstituted $C_{1-4}$ alkyl.

R₁ₐ is selected from hydrogen, methyl and ethyl.

6. The compound as defined in claim 1 having the structure

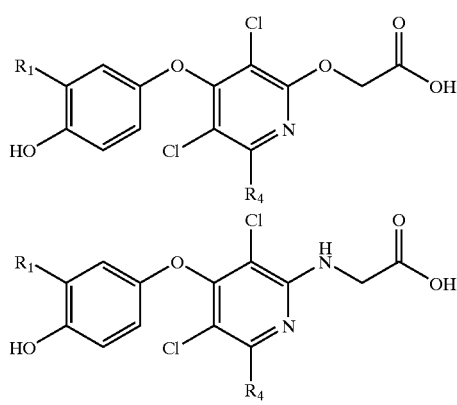

wherein R₁ is substituted or unsubstituted aryl.

7. The compound as defined in claim 1 having the structure

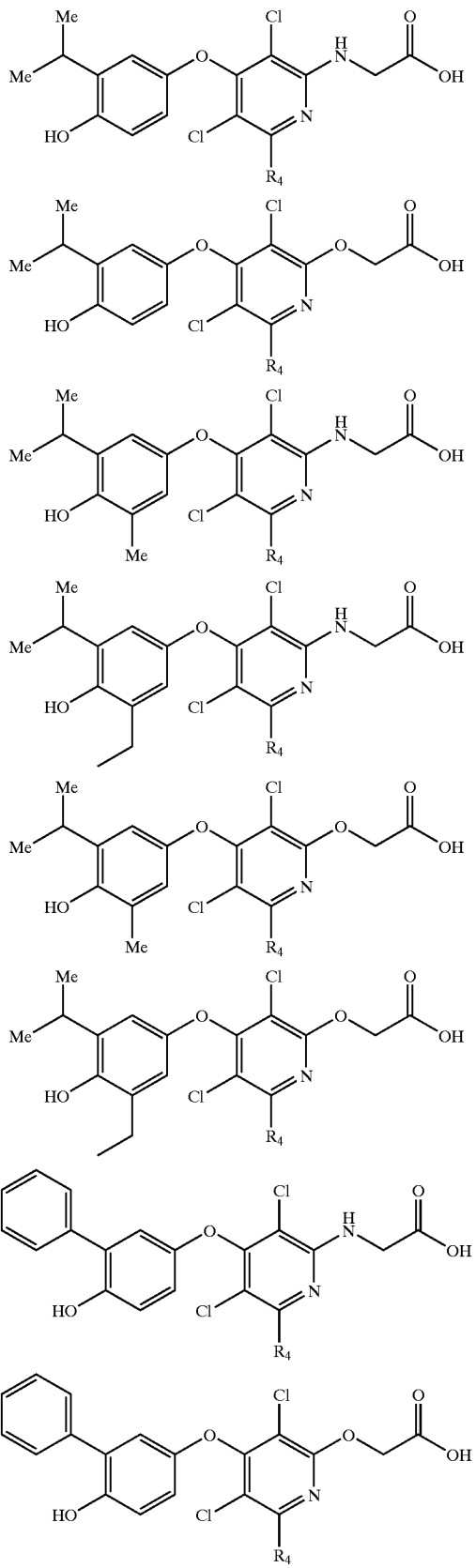

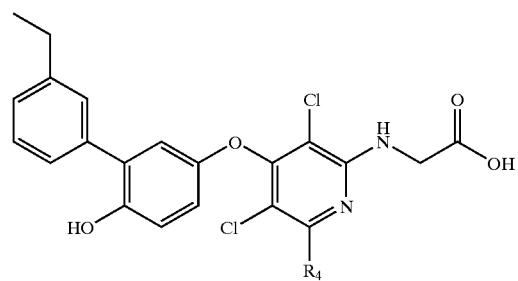
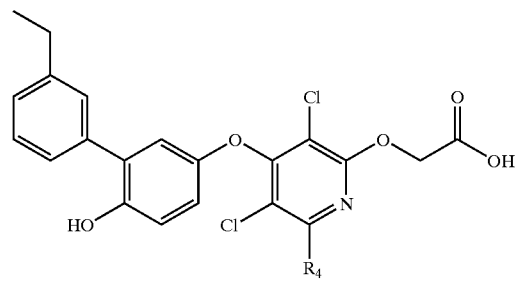
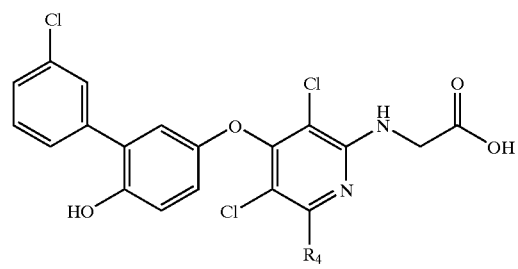
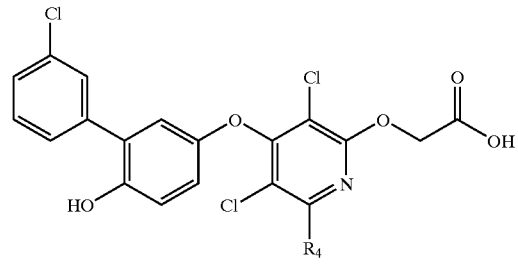
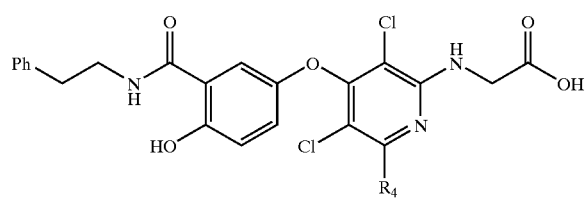
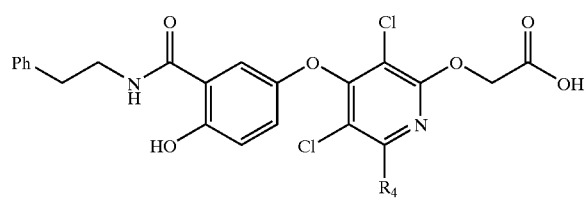
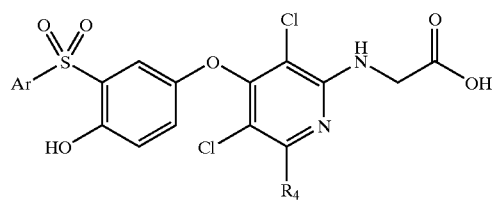
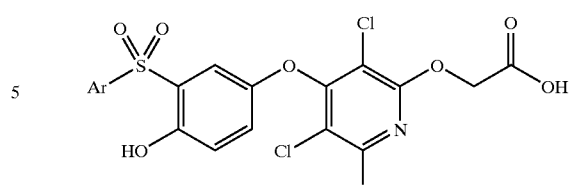
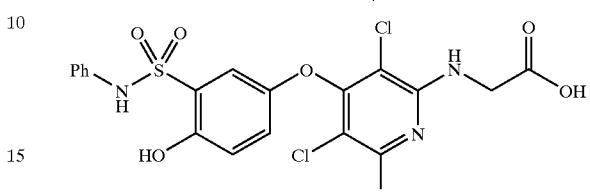
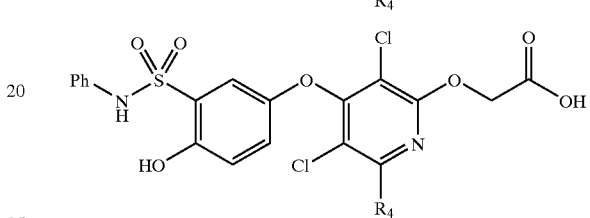
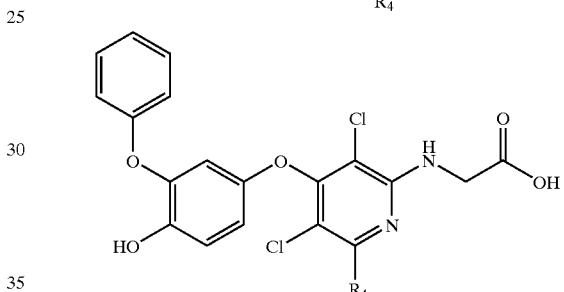
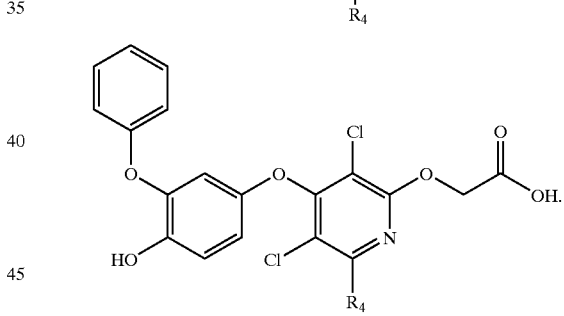
8. The compound as defined in claim 1 having the structure.
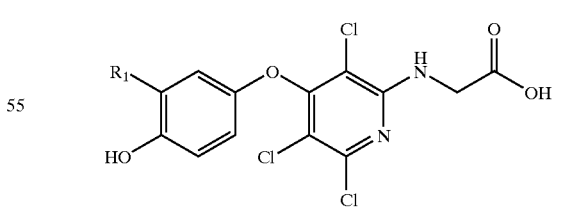
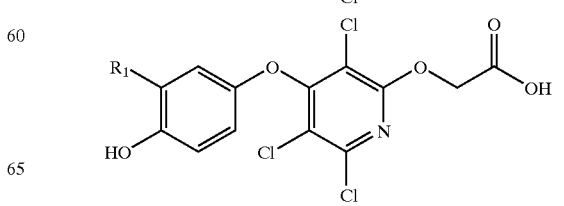

-continued
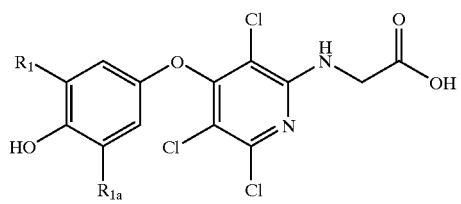
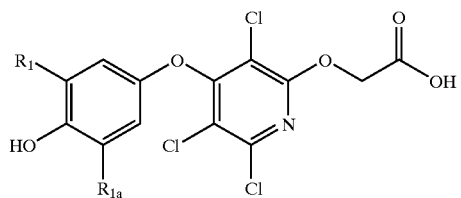
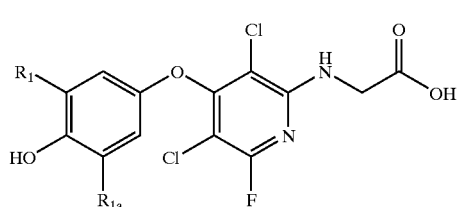
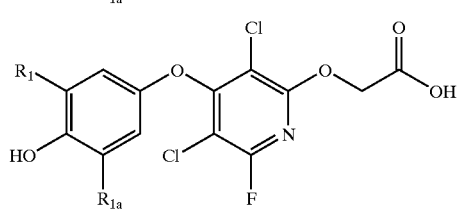
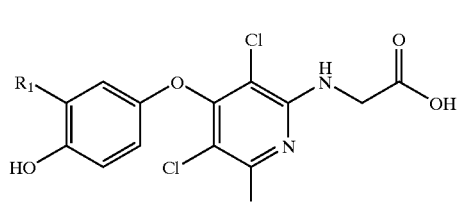
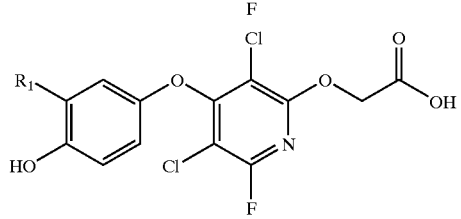
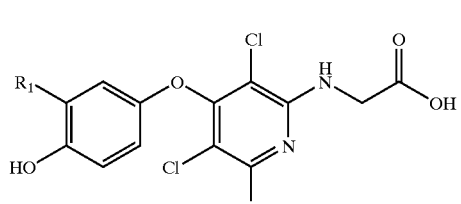
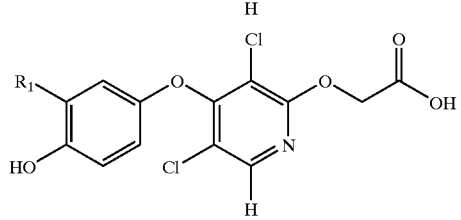
-continued
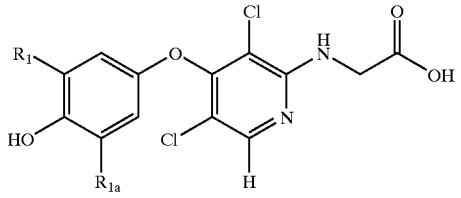
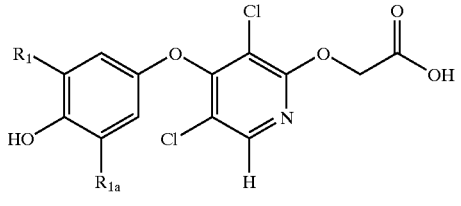
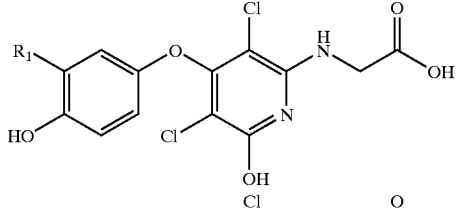
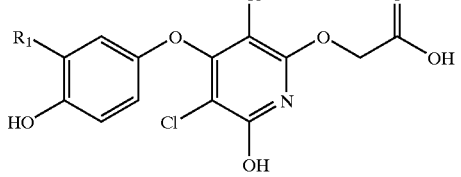
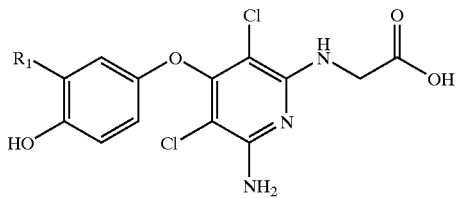
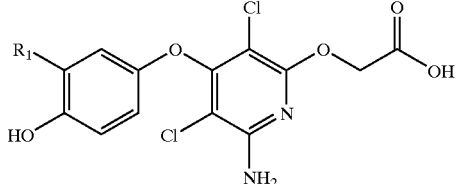
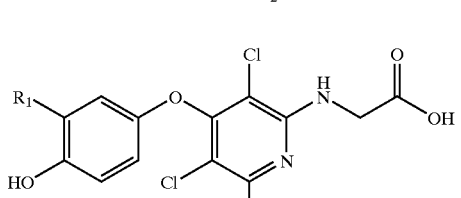
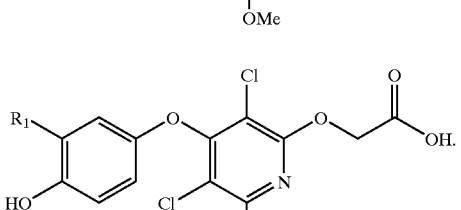
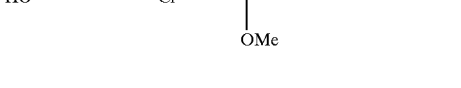

9. The compound as defined in claim 1 having the structure.

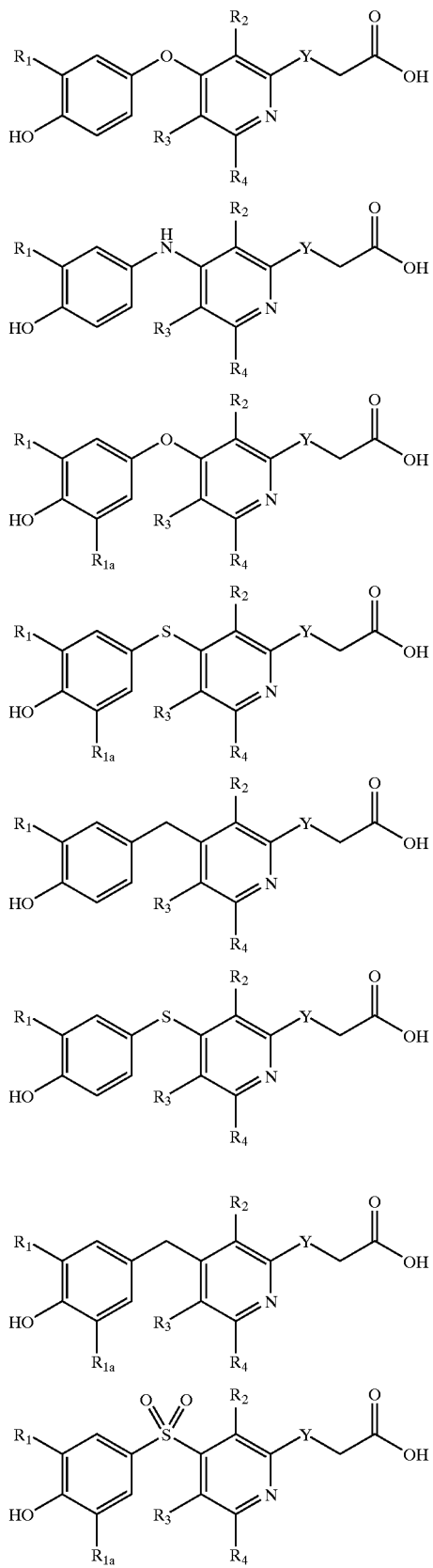
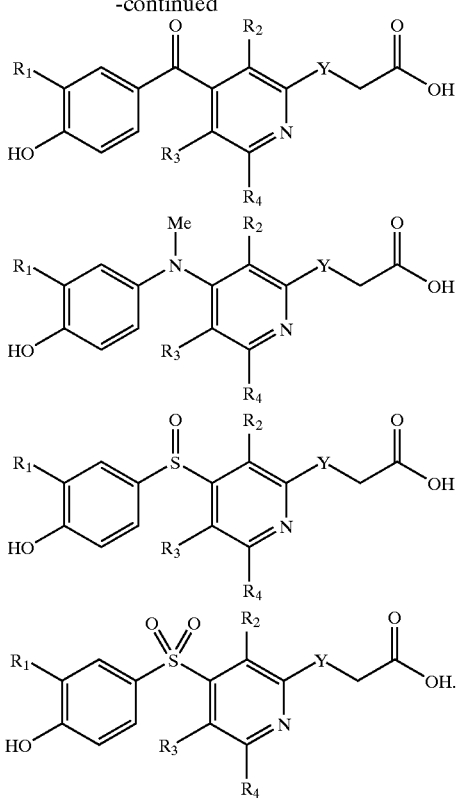

10. A pharmaceutical composition comprising a compound as defined in claim 1 and a pharmaceutically acceptable carrier therefor.

11. The pharmaceutical composition of claim 10 further comprising at least one additional therapeutic agent selected from the group consisting of other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

12. The pharmaceutical composition of claim 11 wherein said additional therapeutic agent is an antidiabetic agent selected from the group consisting of a biguanide, a glucosidase inhibitor, a meglitinide, a sulfonylurea, a thiazolidinedione, a PPAR-alpha agonist, a PPAR-gamma agonist, a PPAR alpha/gamma dual agonist, an SGLT2 inhibitor, a glycogen phosphorylase inhibitor, an aP2 inhibitor, a glucagon-like peptide-1 (GLP-1), a dipeptidyl peptidase IV inhibitor and insulin.

13. The pharmaceutical composition of claim 11 wherein said additional therapeutic agent is an antidiabetic agent selected from the group consisting of metformin, glyburide, glimepiride, glipyride, glipizide, chlorpropamide, gliclazide, acarbose, miglitol, troglitazone, pioglitazone, englitazone, darglitazone, rosiglitazone and insulin.

14. The pharmaceutical composition of claim 11 wherein said additional therapeutic agent is an anti-obesity agent is selected from the group consisting of an aP2 inhibitor, a PPAR gamma antagonist, a PPAR delta agonist, a beta 3 adrenergic agonist, a lipase inhibitor, a serotonin reuptake inhibitor and an anorectic agent.

15. The pharmaceutical composition of claim 11 wherein said additional therapeutic agent is a hypolipidemic agent selected from the group consisting of a thiazolidinedione, an MTP inhibitor, a squalene synthetase inhibitor, an HMG CoA reductase inhibitor, a fibric acid derivative, an ACAT inhibitor, a cholesterol absorption inhibitor, an ileal Na+/bile cotransporter inhibitor, a bile acid sequestrant and a nicotinic acid or a derivative thereof.

16. A method for preventing, inhibiting or treating a disease associated with metabolism dysfunction, or which is dependent on the expression of a $T_3$ regulated gene, which comprises administering to a mammalian patient in need of treatment a therapeutically effective amount of a compound as defined in claim 1.

17. A method for treating or delaying the progression or onset of obesity, hypercholesterolemia, atherosclerosis, depression, osteoporosis, hypothyroidism, subclinical hyperthyroidism, non-toxic goiter, reduced bone mass, density or growth, eating disorders, reduced cognitive function, thyroid cancer, glaucoma, cardiac arrhythmia, congestive heart failure or a skin disorder or disease, which comprises administering to mammalian patient in need of treatment a therapeutically effective amount of a compound as defined in claim 1.

18. The method according to claim 17 wherein the skin disorder or disease is dermal atrophy, keloids, stria, cellulite, roughened skin, actinic skin damage, lichen planus, ichtyosis, acne, psoriasis, Dernier's disease, eczema, atopic dermatitis, chloracne, pityriasis or skin scarring.

19. The method according to claim 17 further comprising administering, concurrently or sequentially, a therapeutically effective amount of at least one additional therapeutic agent selected from the group consisting of other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

20. A method of treating or delaying the progression or onset of a skin disorder or disease which comprises administering to a mammalian patient a therapeutically effective amount of a compound as defined in claim 1 in combination with a retinoid or a vitamin D analog.

21. A method for treating or delaying the progression or onset of obesity which comprises administering to mammalian patient in need of treatment a therapeutically effective amount of a compound as defined in claim 1.

22. A method according to claim 21 further comprising administering, concurrently or sequentially, a therapeutically effective amount of at least one additional therapeutic agent selected from the group consisting of an anti-obesity agent and an appetite suppressant.

23. A method according to claim 22 wherein said anti-obesity agent is selected from the group consisting of aP2 inhibitors, PPAR gamma antagonists, PPAR delta agonists, beta 3 adrenergic agonists, lipase inhibitors, serotonin (and dopamine) reuptake inhibitors, other thyroid receptor beta agents and anorectic agents.

24. A compound of the formula

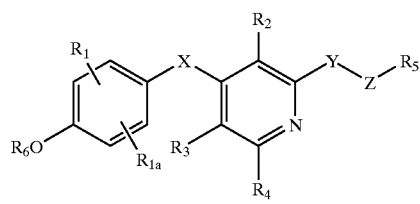

wherein
X is selected from the group consisting of oxygen, sulfur, sulfoxide, sulfonyl, —$CR_8R_8'$— and —$NR_8$;
Y is selected from the group consisting of —$NR_8$, oxygen, —$CH_2$— and sulfur;
Z is a bond or substituted or unsubstituted $C_{1-4}$ alkyl;
$R_1$ is selected from the group consisting of halogen, trifluoromethyl, substituted or unsubstituted $C_{1-6}$alkyl, substituted or unsubstituted aryl, substituted or unsubstituted heteroaryl, aryloxy, substituted amide, sulfone, sulfonamide and $C_{3-7}$ cycloalkyl;
$R_{1a}$ is selected from the group consisting of hydrogen, halogen, substituted or unsubstituted $C_{1-6}$ alkyl, substituted or unsubstituted aryl and substituted or unsubstituted heteroaryl;
$R_2$ and $R_3$ are each independently selected from the group consisting of hydrogen, halogen, unsubstituted or substituted $C_{1-4}$ alkyl and unsubstituted or substituted Cog cycloalkyl, wherein at least one of $R_2$ and $R_3$ being other than hydrogen;
$R_4$ is selected from the group consisting of hydrogen, halogen, amino, O—$R_7$, S—$R_7$ and unsubstituted or substituted $C_{1-4}$ alkyl;
$R_5$ is selected from the group consisting of hydroxyl, carboxylic acid, sulfonic acid and phosphonic acid;
$R_6$ is selected from the group consisting of hydrogen, alkyl, alkanoyl and aroyl;
$R_7$ is hydrogen or $C_{1-4}$ alkyl;
$R_8$ for each occurrence is independently selected from the group consisting of hydrogen, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy and hydroxyl; and
$R_8'$ is selected from the group consisting of hydrogen, a bond, alkyl or substituted alkyl, alkenyl or substituted alkenyl, cycloalkyl or substituted cycloalkyl, cycloalkenyl or substituted cycloalkenyl, heterocyclo or substituted heterocyclo, aryl or substituted aryl, arylalkyl or substituted arylalkyl, alkoxy and hydroxyl, or $R_8$ and $R_8'$ together form a carbonyl,
including all prodrug, stereoisomers and pharmaceutically acceptable salts thereof.

25. A pharmaceutical composition which functions as a selective agonist of the thyroid hormone receptor-beta comprising a compound as defined in claim 1.

* * * * *